(12) United States Patent
Kajaste-Rudnitski et al.

(10) Patent No.: US 11,964,027 B2
(45) Date of Patent: Apr. 23, 2024

(54) METHOD FOR IMPROVING RETROVIRAL TRANSDUCTION AND GENE EDITING IN HEMATOPOIETIC STEM CELLS USING CYCLOSPORINE H (CSH)

(71) Applicants: Ospedale San Raffaele S.R.L, Milan (IT); Fondazione Telethon, Rome (IT)

(72) Inventors: Anna Christina Kajaste-Rudnitski, Milan (IT); Carolina Petrillo, Milan (IT); Bernhard Rudolf Gentner, Milan (IT); Luigi Naldini, Milan (IT); Pietro Genovese, Milan (IT); Giulia Schiroli, Milan (IT)

(*) Notice: Subject to any disclaimer, the term of this patent is extended or adjusted under 35 U.S.C. 154(b) by 1058 days.

(21) Appl. No.: 16/606,633

(22) PCT Filed: Apr. 20, 2018

(86) PCT No.: PCT/EP2018/060237
§ 371 (c)(1),
(2) Date: Oct. 18, 2019

(87) PCT Pub. No.: WO2018/193118
PCT Pub. Date: Oct. 25, 2018

(65) Prior Publication Data
US 2021/0121579 A1    Apr. 29, 2021

(30) Foreign Application Priority Data

Apr. 21, 2017 (GB) ...................................... 1706394

(51) Int. Cl.
| | |
|---|---|
| A61K 48/00 | (2006.01) |
| C07K 7/64 | (2006.01) |
| C12N 5/0789 | (2010.01) |
| C12N 15/69 | (2006.01) |
| C12N 15/86 | (2006.01) |

(52) U.S. Cl.
CPC .......... A61K 48/0008 (2013.01); C07K 7/645 (2013.01); C12N 5/0647 (2013.01); C12N 15/69 (2013.01); C12N 15/86 (2013.01); *C12N 2740/15043* (2013.01)

(58) Field of Classification Search
CPC ...... C07K 7/645; C12N 5/0647; C12N 15/69; C12N 15/86
See application file for complete search history.

(56) References Cited

U.S. PATENT DOCUMENTS

| | | | |
|---|---|---|---|
| 10,391,201 B2* | 8/2019 | Kajaste-Rudnitski | ......................  C07K 7/645 |
| 2013/0323301 A1 | 12/2013 | Gruber et al. | |
| 2015/0352228 A1 | 12/2015 | Torbet et al. | |

FOREIGN PATENT DOCUMENTS

| | | |
|---|---|---|
| WO | WO 2004/032969 | 4/2004 |
| WO | WO 2004/098531 | 11/2004 |
| WO | WO 2014/109728 | 7/2014 |
| WO | WO 2015/059674 | 4/2015 |
| WO | WO 2015/162594 | 10/2015 |
| WO | WO 2016/182959 | 11/2016 |

OTHER PUBLICATIONS

Bouchard, M. J., et al., Jul. 2003, Activation and inhibition of cellular calcium and tyrosine kinase signaling pathways identify targets of the HBx protein involved in hepatitis B virus replication, J. Virol. 77(14):7713-7719.*
Zonari, E., et al., Apr. 11, 2017, Efficient ex vivo engineering and expansion of highly purified human hematopoietic stem and progenitor cell populations for gene therapy, Stem Cell Reports, 8:977-990.*
Cheng, H., et al., 2020, New Paradigms on Hematopoietic Stem Cell Differentiation, Protein Cell 11(1):34-44.*
Bulli, L., et al., Aug. 2016, Complex Interplay between HIV-1 Capsid and MX2-Independent Alpha Interferon-Induced Antiviral Factors, J. Virol. 90(16):7469-7480.*
Petrillo, C., et al., Feb. 2015, Cyclosporin A and Rapamycin Relieve Distinct Lentiviral Restriction Blocks in Hematopoietic Stem and Progenitor Cells, Mol. Ther. 23(2):352-362.*
De Iaco et al., Cyclophilin A promotes HIV-1 reverse transcription but its effect on transduction correlates best with its effect on nuclear entry . . . ; Retrovirol. 11:11 (2014).
Kajaste-Rudnitski et al., Cellular Innate Immunity and Restriction of Viral Infection: Implications for Lentiviral Gene Therapy . . . ; Human Gene Ther. 26:201-209 (2015).
Liu et al., The Interferon-Inducible MxB Protein Inhibits HIV-1 Infection; Cell Host & Microbe 14:398-410 (2013).
Montini et al., Hematopoietic stem cell gene transfer in a tumor-prone mouse model uncovers low genotoxicity . . . ; Nature Biotechnol. 24:687-696 (2006).
Petrillo et al., Cyclosporin A and Rapamycin Relieve Distinct Lentiviral Restriction Blocks in Hematopoietic Stem and Progenitor Cells; Molec. Ther. 23:352-362 (2015).
Rits et al., Efficient Transduction of Simian Cells by HIV-1-based Lentiviral Vectors that Contain Mutations in the Capsid Protein; Molec. Ther. 15:930-937 (2007).
Sutherland et al., Effects of Cyclosporine A on Lentiviral Transduction of Mouse Hematopoietic Stem Cells and Transplantation . . . ; Blood 110:Abstract 5147 (2007).
Uchida et al., Optimal conditions for lentiviral transduction of engrafting human CD34+ cells; Gene Ther. 18:1078-1086 (2011).
Uchida et al., Efficient transduction of human hematopoietic repopulating cells with a chimeric HIV1-based vector including SIV capsid; Exper. Hematol. 41:779-788 (2013).

(Continued)

*Primary Examiner* — Jeffrey S Parkin
(74) *Attorney, Agent, or Firm* — Grimes & Yvon LLP

(57) ABSTRACT

Use of cyclosporin H (CsH) or a derivative thereof for increasing the efficiency of transduction of an isolated population of cells by a viral vector and/or increasing the efficiency of gene editing of an isolated population of cells when transduced by a viral vector.

17 Claims, 42 Drawing Sheets

Specification includes a Sequence Listing.

(56) References Cited

OTHER PUBLICATIONS

Wang et al., Rapamycin relieves lentiviral vector transduction resistance in human and mouse hematopoietic stem cells; Blood 124:913-923 (2014).
Fujita et al., Cyclophilin A-independent replication of a human immunodeficiency virus type 1 isolate; Journal of Virology 75:10527-10531 (2001).
Cornilescu et al., Structure Analysis of the N-Terminal Domain of the Human T-cell Leukemia Virus Capsid Protein; J Mol Biol. 306:783-797 (2000).
Kahl et al., Tissue-specific restriction of cyclophilin A-independent HIV-1 and SIV-derived lentiviral vectors; Gene Therapy 15:1079-1089 (2008).
Noser et al., Cyclosporine increases human immunodeficiency virus type 1 vector transduction; Journal of Virology 80:7769-7774 (2006).
Petrillo et al., Dissectiong Immunomodulatory Relief of Lentiviral Restriction in human Hematopoietic Stem and Progenitor Cells . . . ; Molec. Ther. 22:205 (2014).
Santoni De Sio et al., Lentiviral vector gene transfer is limited by the proteasome at postentry steps in various . . . ; Stem Cells 26:2142-2152 (2008).
Zhang Y., Rational Design of Cyclosporin A Derivatives for selective enzyme Inhibition; Dissertation, Martn Luther Universität Halle-Wittenberg (2001).
Doulatov et al., Revised map of the human progenitor hierarchy show the origin of mcarophages and enedritic cells in early lymphoid . . . ; Nature Immunology 11:585-59 (2010).
Uchida et al., High-efficiency Transudction of Rhesus Hematopoietic Repopulating Cells by a Modified HIV1-based Lentiviral Vector; Molecular Therapy 20:1882-1892 (2012).
Notta et al., Isolation og single human hematopoietic stem cells capable of long-term multilineage engraftment; Science 333:218 (2011).
Hatziloannou et al., Retrovirus resistance factors Ref1 and Lv1 are species-specific variants of TRIM5α; Proc. National Academy of Science 101:10774-10779 (2004).
Zonari et al., Incremental Innovation of Ex Vivo Hematopoietic Stem Cell Engineering to Expand Clinical Gene Therapy Applications; Blood 128:4707 (2016).
Ma et al., Discovery of cyclosporine A and its analogs as broad-spectrum anti-influenza drugs with a high in vitro genetic barrier of . . . ; Antiviral Research 133:62-72 (2016).
Petrillo et al., Novel Molecular and Functional Insight into Cyclosporine-Mediated Enhancement of Human Hematopoietic Stem Cell Gene Therapy; Molec. Ther. 25:340 (2017).
Petrillo et al., Cyclosporine H Overcomes Innate Immune Restrictions to Improve Lentiviral Transduction and Gene Editing in Human . . . ; Cell Stem Cell 23:820-832 (2018).
Jia et al., SIRT1 suppresses PMA and ionomycin-induced ICAM-1 expression in endothelial cells; Sci. China Life Sci. 56:19-25 (2013).

* cited by examiner

B

C

C. VCN in BM of mice

VCN in spleen of mice

D. Engraftment and lineage composition in BM of mice

Engraftment in spleen of mice

B. <u>HSPC % 72h after transduction</u>

H.

I.

J.

K.

L. mPB-CD34 TD IDUA LV; VCN on CFU bulk

M. mPB-CD34 TD IDUA LV; VCN on PB of NSG mice

N.

O. hHSPC, SINRV

A.

B.

C.

D.

E.

A. Murine HSPC

J

K

METHOD FOR IMPROVING RETROVIRAL TRANSDUCTION AND GENE EDITING IN HEMATOPOIETIC STEM CELLS USING CYCLOSPORINE H (CSH)

FIELD OF THE INVENTION

The present invention relates to the genetic modification of cells. More specifically, the present invention relates to the use of compounds to improve the transduction of cells by viral vectors and to improve gene editing of cells.

BACKGROUND TO THE INVENTION

The haematopoietic system is a complex hierarchy of cells of different mature cell lineages. These include cells of the immune system that offer protection from pathogens, cells that carry oxygen through the body and cells involved in wound healing. All these mature cells are derived from a pool of haematopoietic stem cells (HSCs) that are capable of self-renewal and differentiation into any blood cell lineage. HSCs have the ability to replenish the entire haematopoietic system.

Haematopoietic cell transplantation (HCT) is a curative therapy for several inherited and acquired disorders. However, allogeneic HCT is limited by the poor availability of matched donors, the mortality associated with the allogeneic procedure which is mostly related to graft-versus-host disease (GvHD), and infectious complications provoked by the profound and long-lasting state of immune dysfunction.

Gene therapy approaches based on the transplantation of genetically modified autologous HSCs offer potentially improved safety and efficacy over allogeneic HCT. They are particularly relevant for patients lacking a matched donor.

The concept of stem cell gene therapy is based on the genetic modification of a relatively small number of stem cells. These persist long-term in the body by undergoing self-renewal, and generate large numbers of genetically "corrected" progeny. This ensures a continuous supply of corrected cells for the rest of the patient's lifetime. HSCs are particularly attractive targets for gene therapy since their genetic modification will be passed to all the blood cell lineages as they differentiate. Furthermore, HSCs can be easily and safely obtained, for example from bone marrow, mobilised peripheral blood and umbilical cord blood.

Efficient long-term gene modification of HSCs and their progeny requires a technology which permits stable integration of the corrective DNA into the genome, without affecting HSC function. Accordingly, the use of integrating recombinant viral systems such as γ-retroviruses, lentiviruses and spumaviruses has dominated this field (Chang, A. H. et al. (2007) Mol. Ther. 15: 445-456). Therapeutic benefits have already been achieved in γ-retrovirus-based clinical trials for Adenosine Deaminase Severe Combined Immunodeficiency (ADA-SCID; Aiuti, A. et al. (2009) N. Engl. J. Med. 360: 447-458), X-linked Severe Combined Immunodeficiency (SCID-X1; Hacein-Bey-Abina, S. et al. (2010) N. Engl. J. Med. 363: 355-364) and Wiskott-Aldrich syndrome (WAS; Boztug, K. et al. (2010) N. Engl. J. Med. 363: 1918-1927). In addition, lentiviruses have been employed as delivery vehicles in the treatment of X-linked adrenoleukodystrophy (ALD; Cartier, N. et al. (2009) Science 326: 818-823), and very recently for metachromatic leukodystrophy (MLD; Biffi, A. et al. (2013) Science 341: 1233158) and WAS (Aiuti, A. et al. (2013) Science 341: 1233151).

Nevertheless, although lentiviruses are among the best available platforms for cell transduction, difficulties remain with the methods employed for the genetic modification of cells, in particular haematopoietic stem and progenitor cells. For example, for gene therapy to be efficacious, effective gene transfer into target cells must be reached without inducing detrimental effects on their biological properties.

Many existing methods exhibit suboptimal target cell permissivity as high vector doses, prolonged transduction times and ex vivo culture may be required to reach clinically relevant transduction levels. This remains a hurdle for the field as it may give rise to cumbersome, costly and not always sustainable large-scale vector productions and compromised cell quality due to prolonged ex vivo transduction protocols.

Among the side effects reported in gene therapy trials, prolonged neutropenia due to delayed engraftment of ex vivo modified cells is the major cause of treatment-related morbidity and mortality. Delayed recovery may be caused by the ex vivo culture of the cell therapy product, which typically lasts more than 60 hours (Aiuti, A. et al. (2013) Science 341: 1233151; Biffi, A. et al. (2013) Science 341: 1233158). Accumulating experimental evidence suggests that cultured haematopoietic stem and progenitor cells progressively lose engraftment potential by recruitment into the cell cycle and loss of adhesion molecules, thus impeding their homing into the niche, and driving lineage commitment and differentiation. Increasing transduction efficiencies would ultimately enable decreasing the amount of vector required for clinically relevant gene transfer and also a shortening of the ex vivo culture time.

Although progress has been made in improving transduction protocols, for example the inventors have previously demonstrated improvement in transduction efficiency of haematopoietic stem and progenitor cells can be achieved by using cyclosporin A, there remains a need for further approaches to improve genetic modification of cells with viral vectors.

SUMMARY OF THE INVENTION

The inventors have surprisingly found that cyclosporin H (CsH) performed much better than cyclosporin A in improving the transduction of cells, including haematopoietic stem and progenitor cells. CsH provided almost 100% transduction efficiency and up to 3 vector copies per genome after a single lentiviral vector application ("hit") at a moderate multiplicity of infection of 10. These findings were made in the clinically relevant mobilised peripheral blood-derived haematopoietic stem and progenitor cells, and it was observed that CsH did not result in a detrimental effect on the cells' biological properties.

The inventors also found that high transduction levels were maintained in vivo in long-term repopulating haematopoietic stem and progenitor cells and additionally CsH was found to overcome basal and type I IFN-induced lentiviral restriction in these cells. The effects of CsH were also found to be further improved when combined with other early-acting compounds such as rapamycin and prostaglandin E2.

Moreover, the inventors found that CsH increased transduction efficiency in unstimulated haematopoietic stem and progenitor cells, in activated T cells and when using an integrase defective lentiviral (IDLV) vector. CsH also enhanced gene targeting efficiency in murine and human haematopoietic stem and progenitor cells, particularly in the more primitive CD34+CD133+CD90+ fraction. In addition, CsH might be used to reduce the IDLV dose during transduction without compromising targeting efficiency in primary human T cells.

Accordingly, in one aspect the invention provides use of cyclosporin H (CsH) or a derivative thereof for increasing the efficiency of transduction of an isolated population of cells by a viral vector and/or increasing the efficiency of gene editing of an isolated population of cells when transduced by a viral vector.

In one embodiment, the use is for increasing the efficiency of transduction of an isolated population of cells by a viral vector.

In another embodiment, the use is for increasing the efficiency of gene editing of an isolated population of cells when transduced by a viral vector. Preferably, the viral vector is a non-integrating vector (e.g. an integration-defective lentiviral vector, IDLV).

In one embodiment, the gene editing uses one or more zinc-finger nucleases, transcription-activator like effector nucleases (TALENs) and/or CRISPR/Cas systems.

In one embodiment, the cells are haematopoietic stem and/or progenitor cells. In another embodiment, the cells are T cells. In one embodiment, the T cells are CD4+ T cells. In one embodiment, the T cells are CD3+ T cells.

In one embodiment, the isolated population of cells comprises CD34+CD38− cells.

In a preferred embodiment, the cells are human cells.

In one embodiment, the cells are stimulated cells. In another embodiment, the cells are unstimulated cells.

In one embodiment, the viral vector is a retroviral vector. In a preferred embodiment, the viral vector is a lentiviral vector.

In one embodiment, the lentiviral vector is derived from HIV-1, HIV-2, SIV, FIV, BIV, EIAV, CAEV or visna lentivirus. In a preferred embodiment, the lentiviral vector is derived from HIV-1. The HIV-1-derived vector may be, for example, derived from any of the HIV-1 strains NL4-3, IIIB_LAI or HXB2_LAI (X4-tropic), or BAL (R5-tropic), or a chimaera thereof.

In one embodiment, the viral vector is a non-integrating vector. In one embodiment, the viral vector is an integration-defective lentiviral vector (IDLV), for example an integration-defective vector derived from HIV-1.

In one embodiment, the viral vector is a gamma-retroviral vector.

In one embodiment, the vector is "matched" to the host cell. By "matched" it is to be understood that the vector capsid is derived from a virus which naturally infects a certain type of host (for example, HIV capsids are "matched" to humans). Therefore, in one embodiment, a vector for use in human haematopoietic stem and/or progenitor cells does not comprise capsid proteins other than those derived from a human immunodeficiency virus.

In a preferred embodiment, the viral vector is a VSV-g pseudotyped vector.

In one embodiment, the viral vector is pseudotyped to enter cells via an endocytosis-dependent mechanism.

In one embodiment, the viral vector is not a Ampho-RV pseudotyped vector. In one embodiment, the vector is not a BaEV-TR pseudotyped vector.

In one embodiment, the percentage of cells transduced by the vector is increased. In another embodiment, the vector copy number per cell is increased. Both the percentage of cells transduced by the vector and the vector copy number per cell may be increased at the same time.

In one embodiment, the gene editing efficiency is increased in primitive haematopoietic stem cells. In one embodiment, the gene editing efficiency is increased in CD34+CD133+CD90+ cells.

In one embodiment, the CsH or derivative thereof is at a concentration of about 1-50 µM. In another embodiment, the CsH or derivative thereof is at a concentration of about 5-50 µM. In another embodiment, the CsH or derivative thereof is at a concentration of about 10-50 µM.

In another embodiment, the CsH or derivative thereof is at a concentration of about 1-40, 5-40 or 10-40 µM. In another embodiment, the CsH or derivative thereof is at a concentration of about 1-30, 5-30 or 10-30 µM. In another embodiment, the CsH or derivative thereof is at a concentration of about 1-20, 5-20 or 10-20 µM. In another embodiment, the CsH or derivative thereof is at a concentration of about 1-15, 5-15 or 10-15 µM.

In another embodiment, the CsH or derivative thereof is at a concentration of about 1-15, 2-14, 3-13, 4-12, 5-11, 6-10 or 7-9 µM.

For example the concentration of CsH may be about 1, 2, 3, 4, 5, 6, 7, 8, 9, 10, 11, 12, 13, 14, 15, 20, 25, 30, 35, 40, 45 or 50 µM. In a preferred embodiment, the concentration of CsH or a derivative thereof is about 5, 6, 7, 8, 9, 10, 11, 12, 13, 14 or 15 µM. In a particularly preferred embodiment, the concentration of CsH or a derivative thereof is about 10 µM.

In one embodiment, the population of cells is contacted with CsH or a derivative thereof in combination with another agent capable of increasing the efficiency of transduction.

In one embodiment, the population of cells is contacted with CsH or a derivative thereof in combination with rapamycin or a derivative thereof.

In one embodiment, the population of cells is contacted with CsH or a derivative thereof in combination with prostaglandin E2 or a derivative thereof. In a preferred embodiment, the prostaglandin E2 derivative is 16-16 dimethyl prostaglandin E2.

In one embodiment, the population of cells is contacted with CsH or a derivative thereof in combination with Staurosporine or a derivative thereof.

In one embodiment, the population of cells is contacted with CsH or a derivative thereof in combination with rapamycin or a derivative thereof, and prostaglandin E2 or a derivative thereof.

In another aspect, the invention provides a method of transducing a population of cells comprising the steps of:
  (a) contacting the population of cells with cyclosporin H (CsH) or a derivative thereof; and
  (b) transducing the population of cells with a viral vector.

In one embodiment, steps (a) and (b) are carried out in vitro or ex vivo.

In one embodiment, the method includes a further step of enriching the population for haematopoietic stem and/or progenitor cells. The step of enriching the population for haematopoietic stem and/or progenitor cells may be carried out before contacting the population of cells with CsH or a derivative thereof. Alternatively, or additionally, the step of enriching the population for haematopoietic stem and/or progenitor cells may be carried out after transducing the population of cells with a vector.

The method may also include wash steps. The wash step may be used to substantially remove the CsH or derivative thereof from the medium. The wash step may be carried out after transducing the population of cells with a vector.

Alternatively, or additionally, the wash step may be carried out before transducing the cells.

In one embodiment, the population of haematopoietic stem and/or progenitor cells is obtained from mobilised peripheral blood, bone marrow or umbilical cord blood.

In another aspect, the invention provides a method of gene therapy comprising the steps of:
 (a) transducing a population of cells according to the method of the invention; and
 (b) administering the transduced cells to a subject.

In one embodiment, the transduced cells are administered to a subject as part of an autologous stem cell transplant procedure. In another embodiment, the transduced cells are administered to a subject as part of an allogeneic stem cell transplant procedure.

In another aspect, the invention provides a population of cells prepared according to the method of the invention.

In another aspect, the invention provides a pharmaceutical composition comprising the population of cells of the invention.

In another aspect, the invention provides the population of cells of the invention for use in therapy.

In one embodiment, the population is administered to a subject as part of an autologous stem cell transplant procedure. In another embodiment, the population is administered to a subject as part of an allogeneic stem cell transplant procedure.

In another aspect, the invention provides cyclosporin H (CsH) or a derivative thereof for use in gene therapy.

Figure 1:
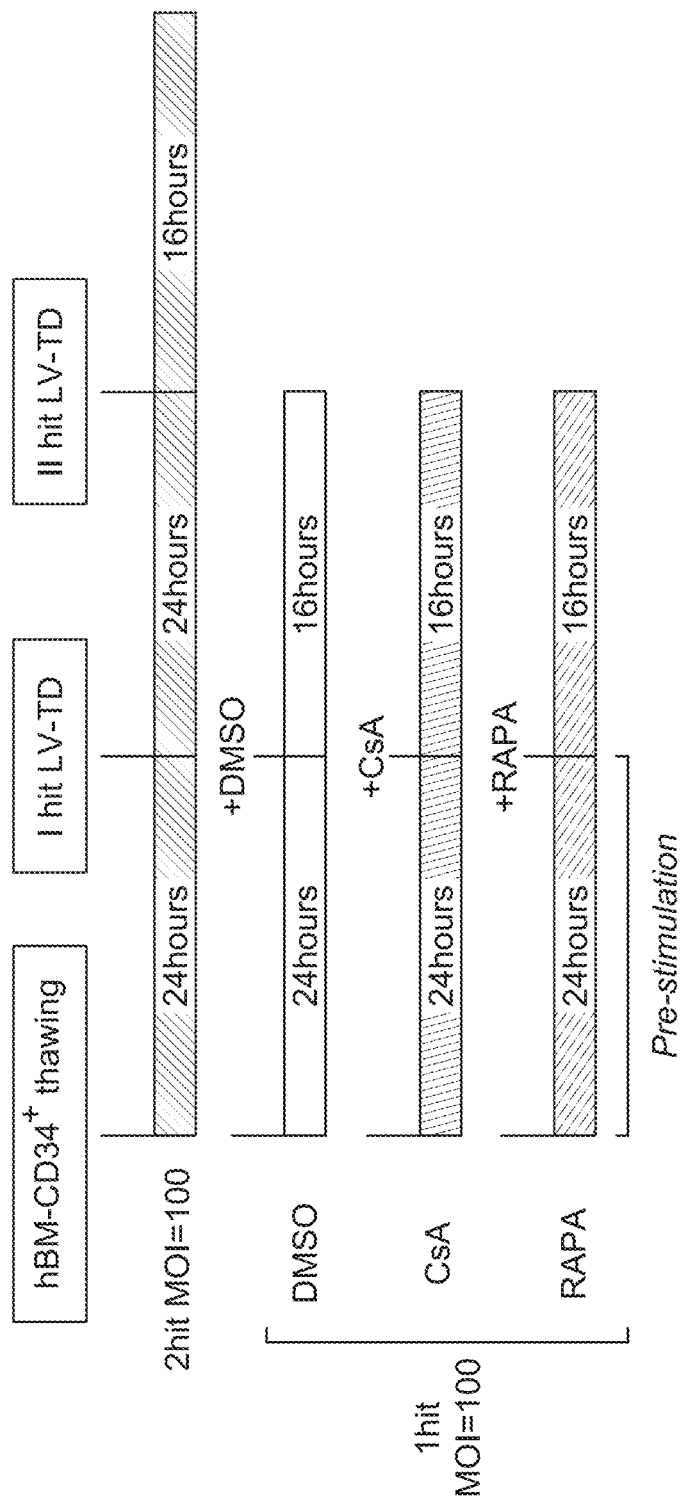
FIG. 1
Figure 1:
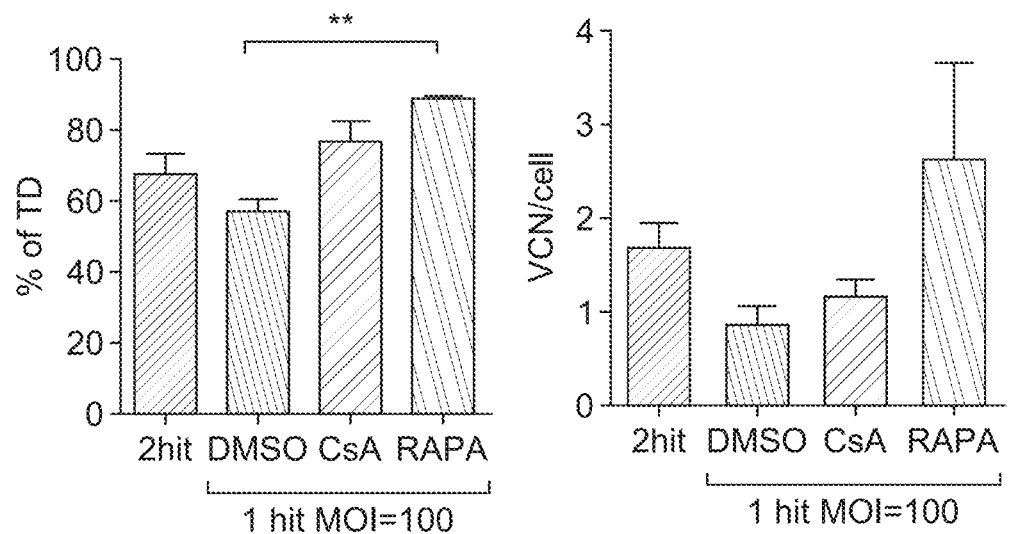
Figure 1:
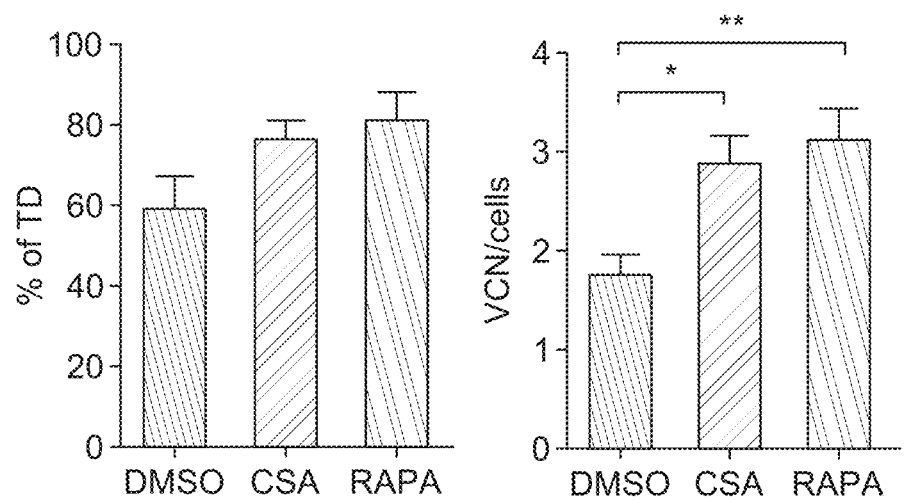
Figure 1:
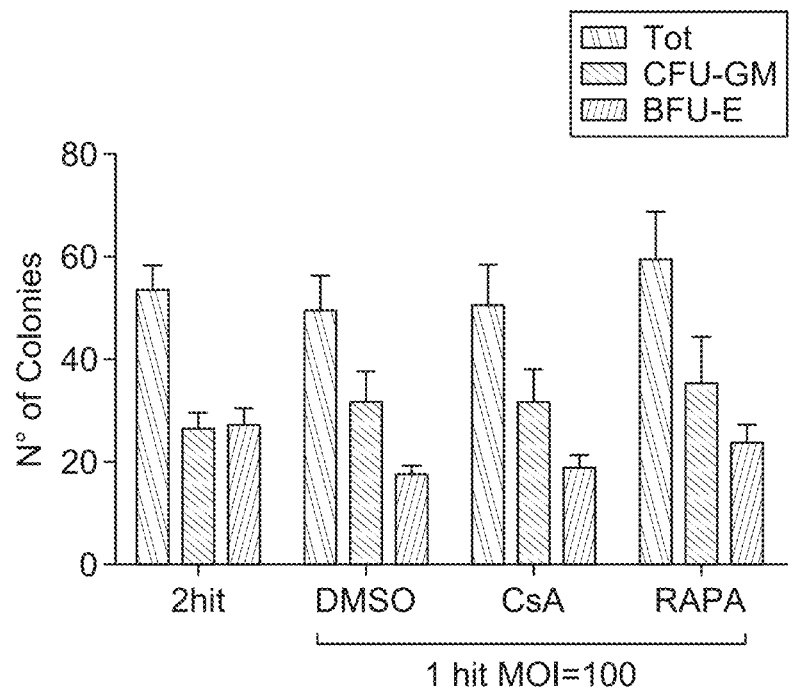
Figure 1:
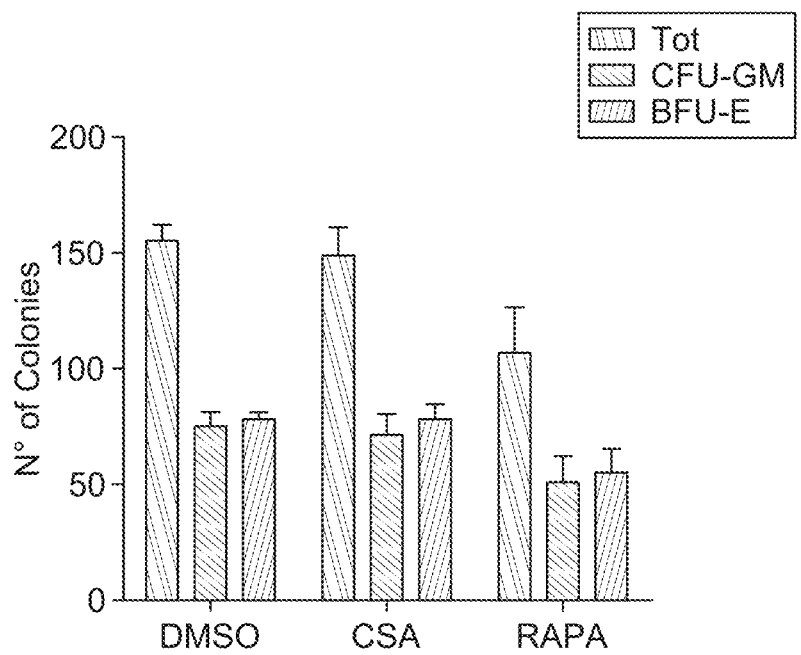

Shorter cyclosporin A (CsA) and rapamycin (Rapa)-based transduction protocols compared to the current clinical standard. (A) Scheme of the experimental approach comparing the different transduction protocols using two clinical-grade LVs and bone marrow (BM)-derived CD34+ cells. (B-C) The percentage of transduction (TD) and vector copy numbers (VCN) per cell as well as (D) the number of colony-forming units (CFU-GM, BFU) counted 14 days after plating are shown for cells transduced with IDUA or ARSA-encoding LV. Data are the mean±SEM of three independent experiments in triplicate each, p values are for One-way ANOVA with Bonferonni's multiple comparison versus DMSO, * for $p<0.05$, ** for $p<0.01$.

FIG. 2

Shorter transduction protocols, in particular in the presence of CsA, improve HSPC engraftment in vivo. (A-B) Peripheral blood analyses in NSG mice at different times post-transplant: (A) engraftment levels evaluated as percent of human CD45+ cells over the total of blood mononuclear cells (y-axis) in mice from different treatment groups (indicated on the x-axis), (B) percentages of human B, T and myeloid cell linages (hCD19+, hCD3+ and hCD13+, respectively) within human CD45+ cells are shown overtime. (C) VCN and (D) engraftment levels of human CD45+ cells in the bone marrow (BM) and spleen are shown at 20 weeks post-transplant. All values are expressed as mean±SEM. p values are for One way ANOVA with Bonferroni's multiple comparison.

FIG. 3

CsA preserves primitive HSCs ex vivo independently of transduction. The subpopulation composition of BM-derived CD34+ HSPCs was measured using the gating strategy shown at (A) 16 hours and (B) 72 hours post-transduction in the presence or absence of CsA. Data represent the mean±SEM of three independent experiments. p values are for One way ANOVA with Bonferroni's multiple comparison.

FIG. 4

CsA reduces HSPC proliferation and preserves quiescence in culture. BM-derived CD34+ cells were stained with a red fluorescent dye that can be used to monitor individual cell divisions, as shown in (A). The mean fluorescence intensity (MFI) of the dye was monitored over time by FACS in the total CD34+ population (B) and within the different subpopulations at (C) 16 hours and (D) 72 hours of culture. (E) Cell cycle status and (F) ROS levels of BM-derived HSPCs was assessed in the presence or absence of CsA at 48 hours post-transduction. Data represent the mean±SEM of three independent experiments. p values are for One way ANOVA with Bonferroni's multiple comparison.

FIG. 5

CsH is a potent and non-toxic enhancer of lentiviral (LV) vector transduction in haematopoietic stem cells.

(A, B) Human CB-derived $CD34^+$ cells were transduced with an LV expressing a shRNA against CypA or a non-silencing control at an MOI of 100 and knock-down (KD) of CypA was verified by Western blot (A) and by mRNA expression (B). Levels of CypB were monitored as a control of RNAi specificity (A, B). (C) Impact of the depletion was then evaluated by transducing the cells with a second LV at an MOI of 10 and evaluating transduction efficiency by FACS in terms of $GFP^+$ cells and by VCN. (D) Human cord-blood (CB) (mean±SEM; n=20; One way ANOVA with Bonferroni's multiple comparison, *$p<0.05$, $p<0.01$, **$p<0.0001$), (E) mobilised peripheral blood (mPB)-$CD34^+$ cells (mean±SEM, n=4, Mann Whitney test, *$p<0.05$), or (F) murine HSPC (mHSPC) (mean±SEM, n=8, Wilcoxon Signed Rank Test, *$p=0.0078$) were transduced with a VSV-g PGK-GFP/BFP WT LVs at a multiplicity of infection (MOI) of 1 transducing unit (TU)/293T cell in the presence or absence of 8 μM CsA or CsH. Percentages of transduced cells and vector copy numbers/human genome (VCN/genome) were assessed at 5 or 14 days post-transduction, respectively. Impact of CsA and CsH on (G) apoptosis (mean±SEM; n=6; Dunn's adjusted Kruskal-Wallis test, ns=not significant) and (H) cell proliferation (mean±SEM; n=4; Dunn's adjusted Kruskal-Wallis test, *$p<0.05$) was assessed in $hCB-CD34^+$ cells 48 hours post-transduction. (K) Transduction efficiencies in the different subpopulations were measured in human CB- or mPB-$CD34^+$ cells transduced with LV at an MOI of 1 (mean±SEM, n=4, Mann Whitney test vs. each DMSO, *$p<0.05$). (N) The composition and cell cycle status of hCB- or mPB-$CD34^+$ cells transduced in the presence of CsH was evaluated 48 hours post-transduction. (1,J) hCB- and mPB-derived HSPC were transduced in the presence of different drug combinations with LV at an MOI of 1 or 10. (O) hCB-CD34+ cells were transduced with a VSV-g pseudo-typed γRV at MOI=10 with or without 8 μM CsH (mean±SEM, n=4, Mann Whitney test, *$p<0.05$). (L) VCN retrieved from mPB-CD34+ cells transduced with the clinical grade IDUA-LV at an MOI of 50 14 days post-transduction in vitro. (M) VCN retrieved from the peripheral blood of NSG-mice 8 weeks after transplantation with human mPB-CD34+ cells transduced with the clinical-grade IDUA-LV at an MOI of 50, represented as fold increase versus the 2-hit group.

FIG. 6

Characterisation of the CsH capacity to improve LV transduction. (A) Human monocyte-derived macrophages (MDM) pre-exposed or not to Vpx (mean±SEM, n=3) and (B) primary CD3⁺ or CD4⁺ T cells were transduced at an MOI of 1 in presence or absence of 8 µM CsA/H (mean±SEM, n=8, Wilcoxon Signed Rank Test vs. DMSO=1, **p=0.0078). (C-H and J-L) human CD34+ cells from different sources were transduced with different vectors as indicated, in the presence or absence of CsA or CsH and transduction efficiencies were evaluated 5 days post-transduction. For example, hCB-CD34+ cells were transduced at an MOI of 50 with an integrase defective LV (IDLV) vector with or without CsH (H). (I) Late-RT and 2LTR circle replication intermediates were measured in CB-CD34⁺ cells transduced with an LV MOI 100 at 6 or 24 hours post-transduction (mean±SEM, n≥3). Transduction efficiencies were evaluated 5 days post-transduction. (M,N) Transduction efficiency (M) and apoptosis (N) in human CB-CD34⁺ cells in presence of different concentrations of CsH (mean±SEM, n=2). Data represent the mean±SEM of three independent experiments. p values are for One way ANOVA with Bonferroni's multiple comparison.

FIG. 7

Cyclosporines counteract an IFN-inducible block to VSV-g-mediated vector entry. (A) THP-1 (mean±SEM; n=10; One way ANOVA with Bonferroni's multiple comparison, *p<0.05, *p<0.001; Mann Whitney test, $$$p=0.0007), (B) K562 (mean±SEM, n=8) and (C) human CB-derived CD34⁺ cells (mean±SEM; n=6; One way ANOVA with Bonferroni's multiple comparison, p=0.0051; Mann Whitney test, $p=0.02) were pre-stimulated or not with 1000 IU/mL of human IFNα for 24 hours followed by transduction with an LV at an MOI of 1 in the presence or absence of 8 µM CsA/H. (D) THP-1 cells pre-stimulated with human IFNα and transduced with Ampho-pseudotyped RV with or without CsH (mean±SEM, n=4). (E) THP-1 (mean±SEM, n=4); and (F) human CB-derived CD34⁺ cells (mean±SEM, n≥4) were pre-stimulated or not with IFNα for 24 hours followed by transduction with a BaEV-TR LV at an MOI of 0.5-1 in presence or absence of CsA/H. Transduction efficiencies were assessed by FACS 5 days post-transduction.

FIG. 8

CsH increases gene editing in human and murine HSPCs. (A) The percentage of gene edited GFP+ human CB-derived CD34+ subpopulations or murine Lin− HSPCs was assessed 3 days post-nucleofection. (B) CB-CD34+ subpopulation composition was assessed by FACS 3 days post-nucleofection. Data represent the mean±SEM of two independent experiments.

FIG. 9

CsA does not alter LV integration profiles in human HSPC. Lentiviral integration sites were retrieved from genomic DNA extracted from CB-derived CD34+ HSPCs transduced at an MOI of 100 in the presence or absence of CsA. Genome distribution of identified integration sites (IS) are shown in circos plot. The human genome is represented by chromosomes 1 to 22, x and y clockwise from top (outer circle). The middle circle represents all IS with their abundancy reflected in the height of the peak with green peaks corresponding to IS from control transduced cells and red to those from cells transduced in the presence of CsA. The blue histograms within the inner circle represent the significance of the difference between the two groups (DMSO v. CsA), the higher the histogram the more significant is the difference. The red band is set at the threshold of p<0.1 and histograms crossing it can be considered significant.

FIG. 10

CsH increases gene transfer and editing in long-term SCID-repopulating human HSPC. (A) Experimental scheme of the different transduction protocols using a clinical-grade LV and human mPB-derived CD34⁺ cells. (B) The number of myeloid and erythroid colony-forming units (CFU) were assessed in vitro (mean±SEM; n=8; Dunn's adjusted Kruskal-Wallis test vs. 2hit total CFU, *p≤0.05). (C) VCN/genome were measured in the bone marrow (BM) at 18 weeks (mean±SEM; n=8; Dunn's adjusted Kruskal-Wallis, *p<0.05, *p<0.001). (D, E) Engraftment levels were evaluated as percent of human CD45⁺ cells over the total of blood mononuclear cells (y-axis) in the peripheral blood of mice from different treatment groups (indicated on x-axis) (mean±SEM; n≥11; Dunn's adjusted Kruskal-Wallis, ns=not significant). (F) Engraftment levels of human CD45⁺ cells in the BM are shown at 18 weeks post-transplant (mean±SEM; n≥11; Dunn's adjusted Kruskal-Wallis, p<0.01). (G) Scheme of the gene editing protocol for human CB-derived CD34⁺ cells. (H) Percentage of edited cells measured within the indicated subpopulations 3 days after editing (mean±SEM; n=7, Mann-Whitney test, *p<0.05, *p<0.05). (1) Human CD45⁺ cell engraftment in peripheral blood (PB) at indicated times after transplantation of edited CB-CD34⁺ cells (n=5). (J) Percentage of gene editing by homology-driven repair (HDR) measured within human cells in mice from (1). (K) Percentage of human gene edited cells and editing efficiency in the BM of mice from (J).

FIG. 11

Figure 10:
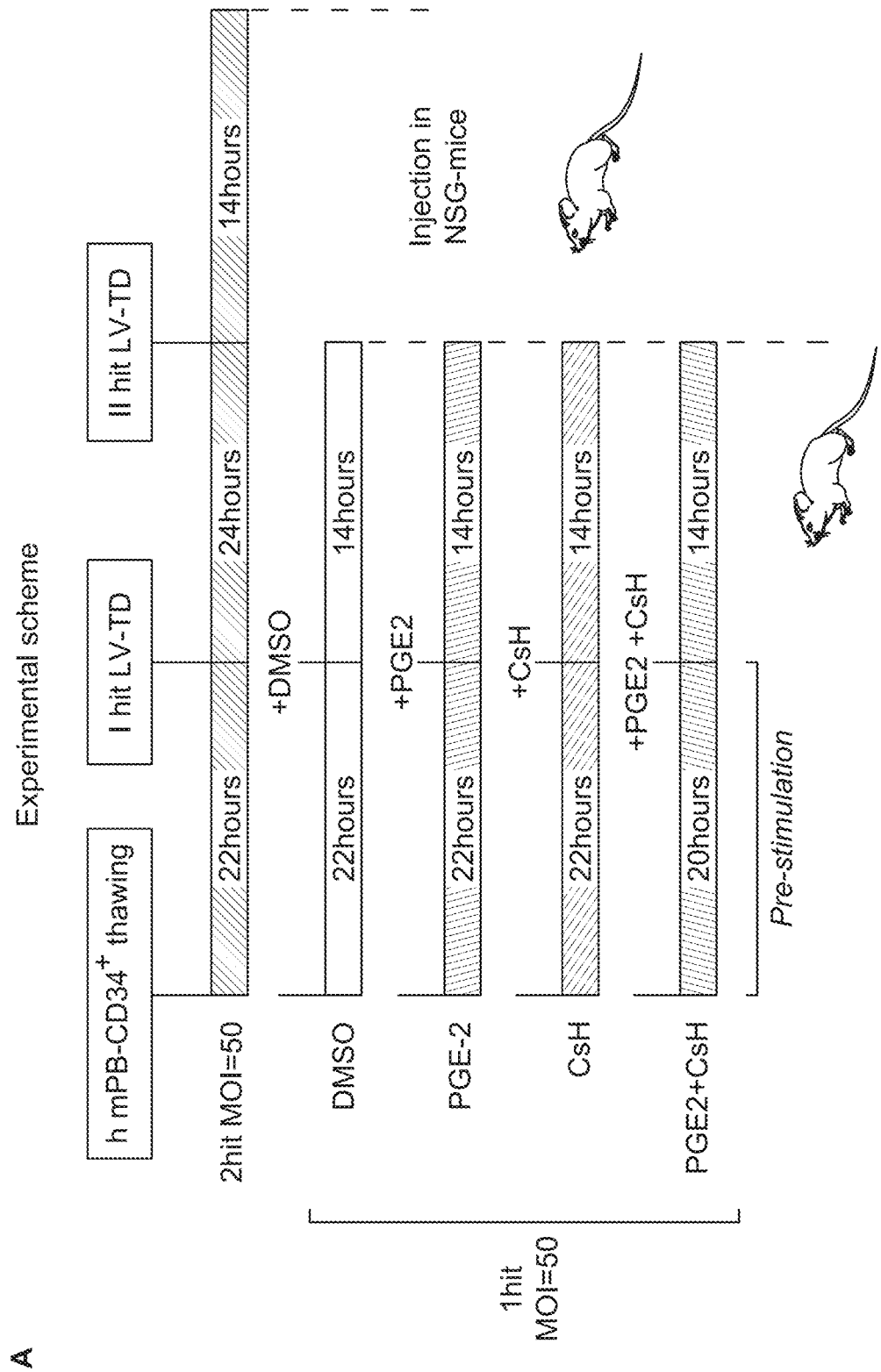
Figure 10:
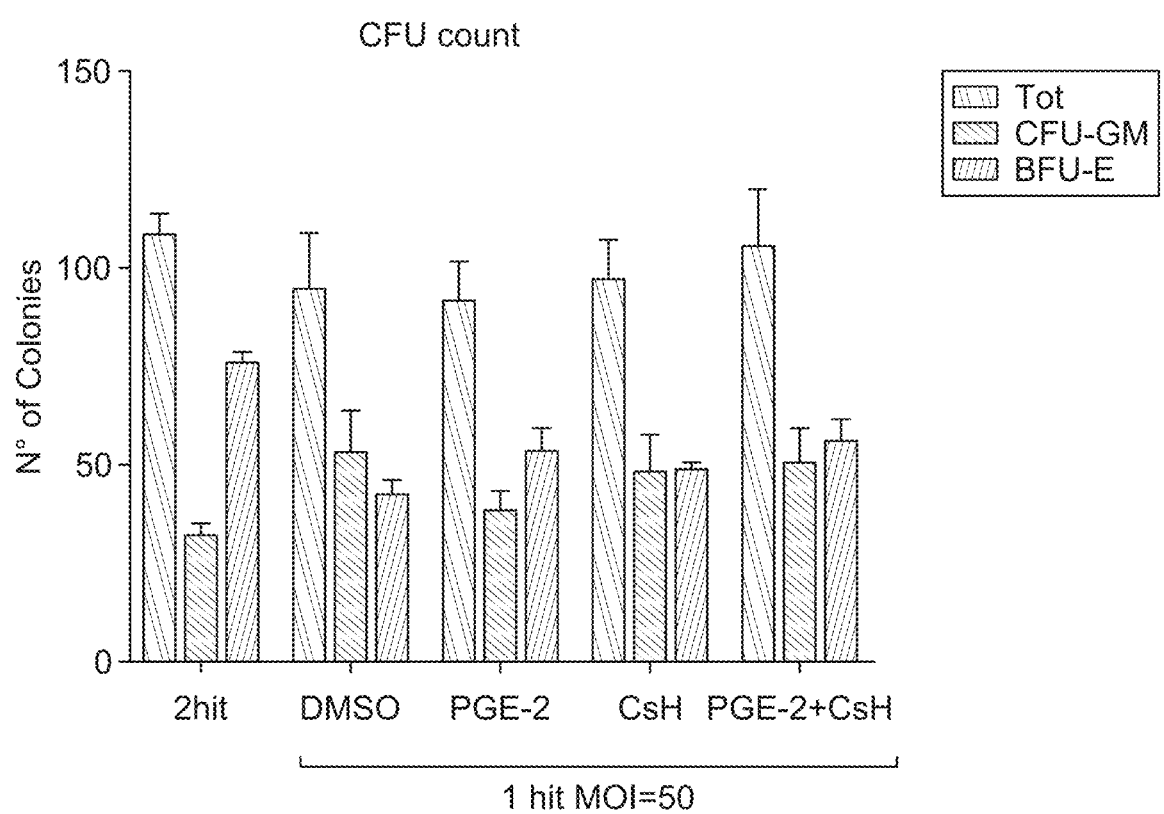
Figure 10:
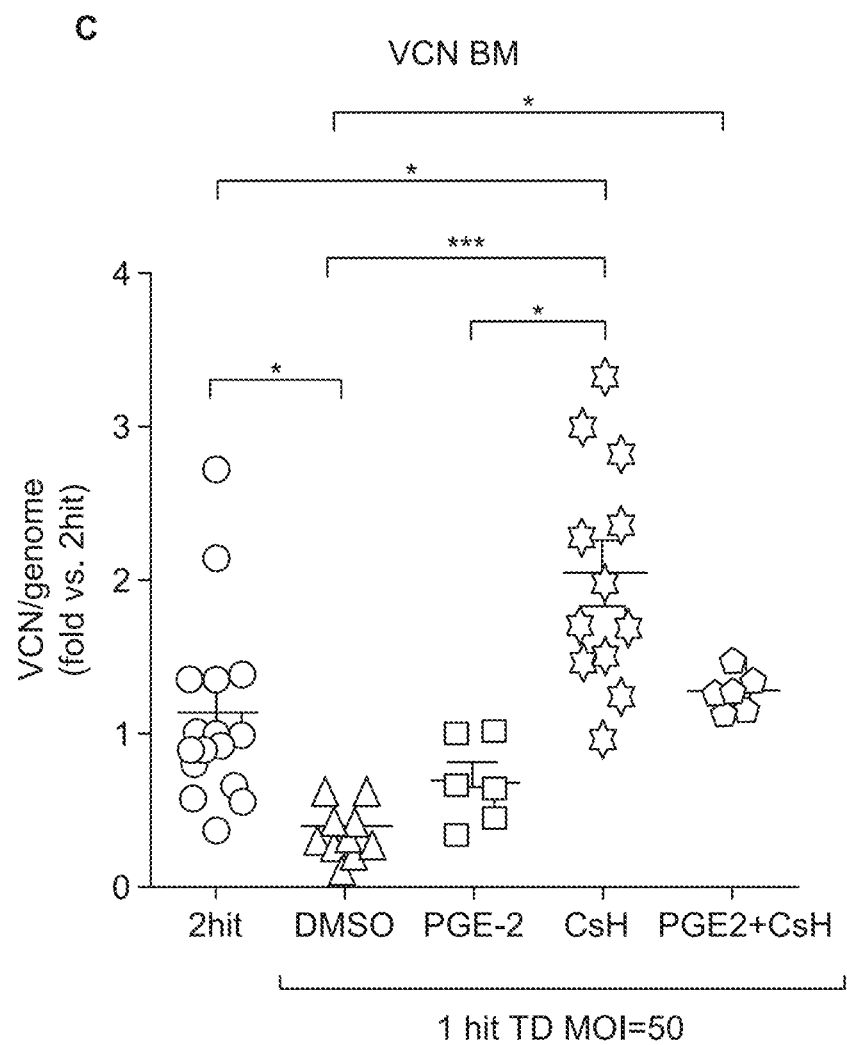
Figure 10:
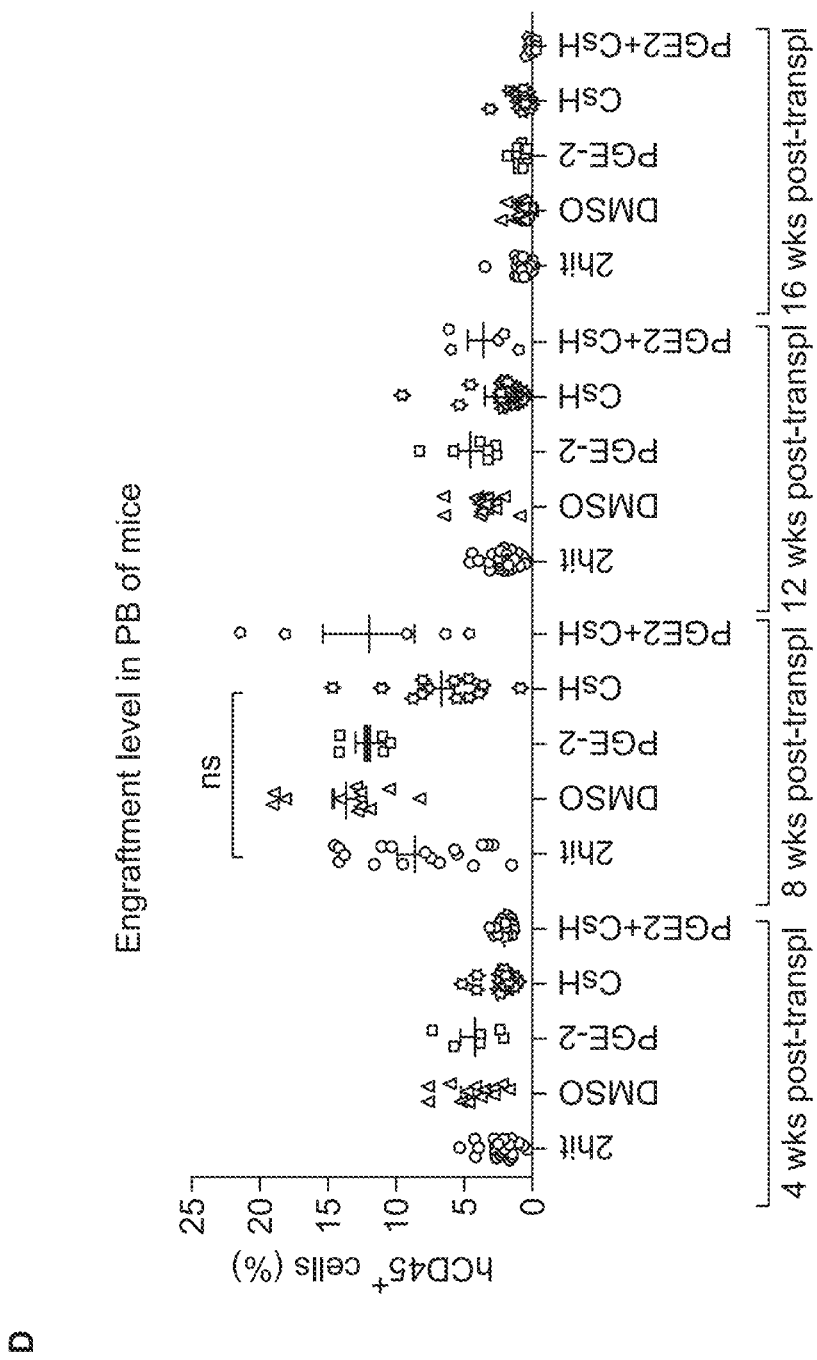
Figure 10:
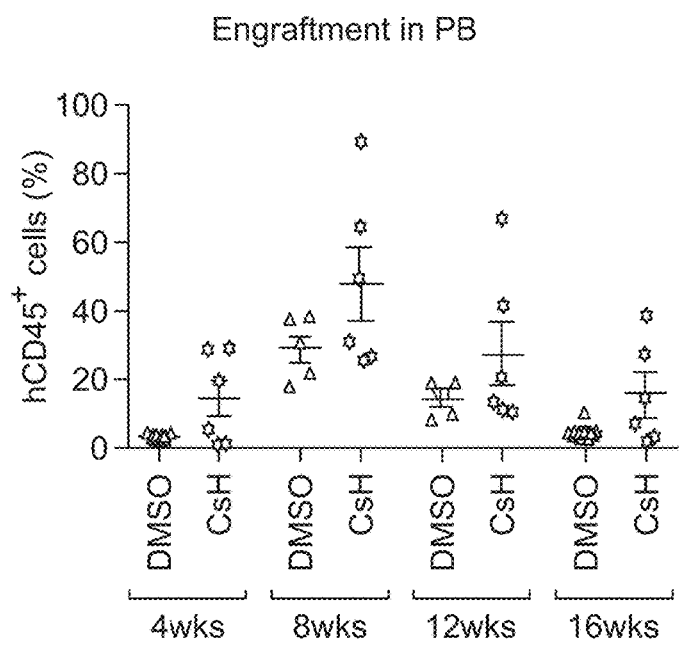
Figure 10:
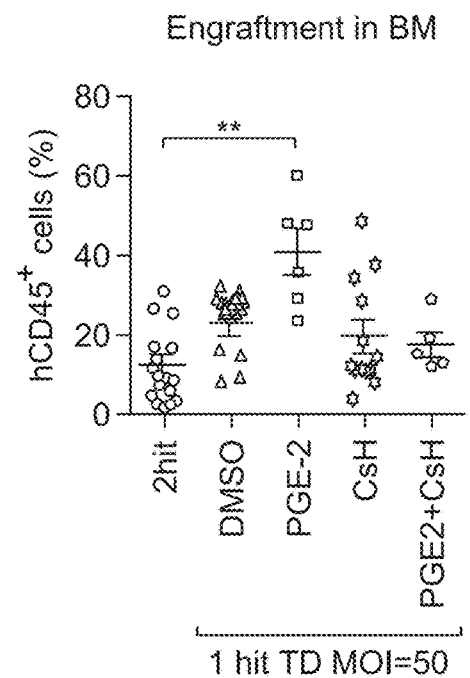
Figure 10:
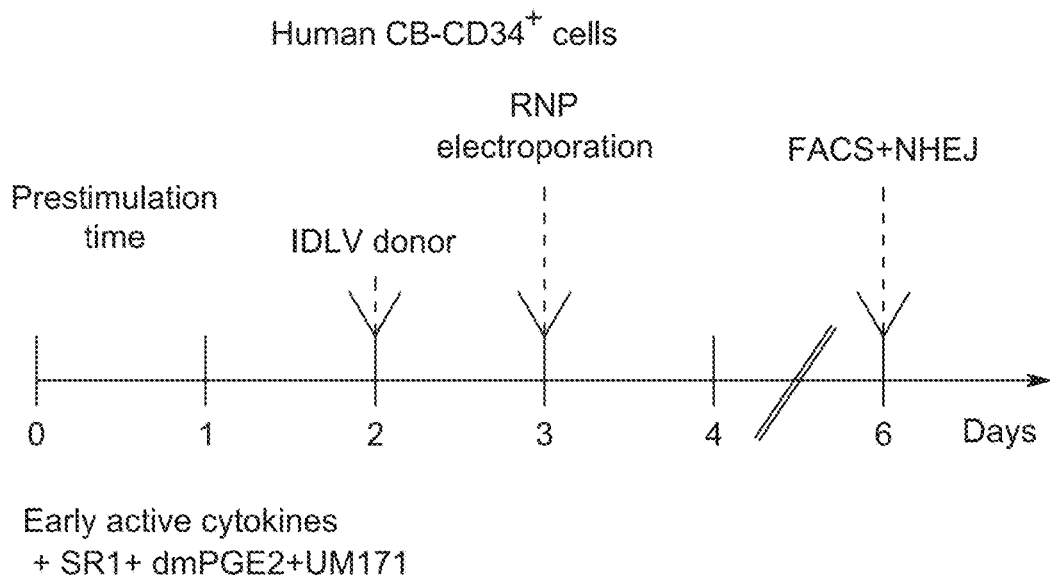
Figure 10:
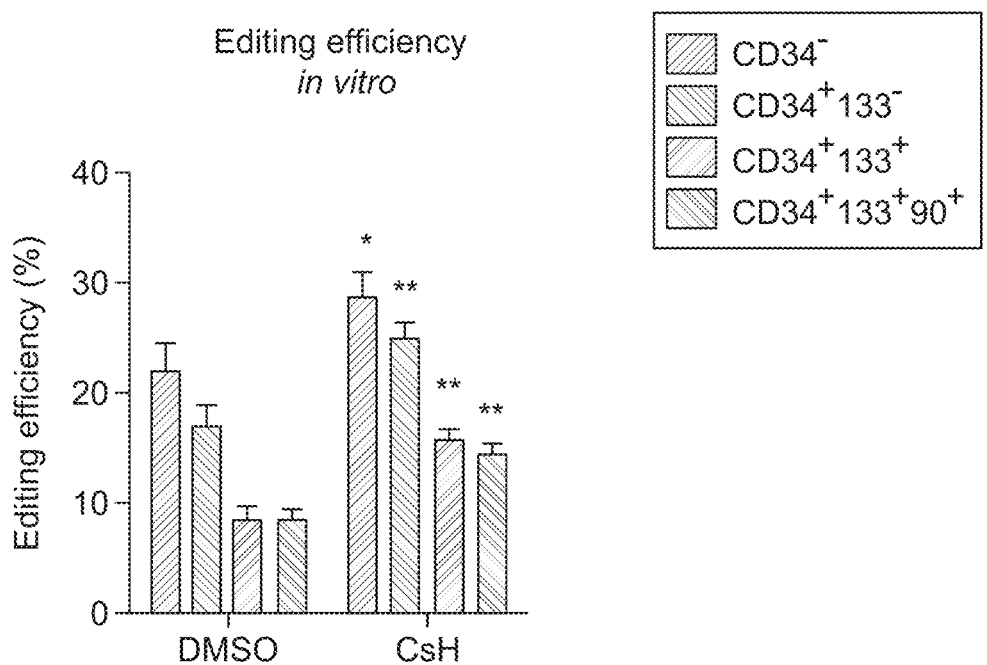
Figure 10:
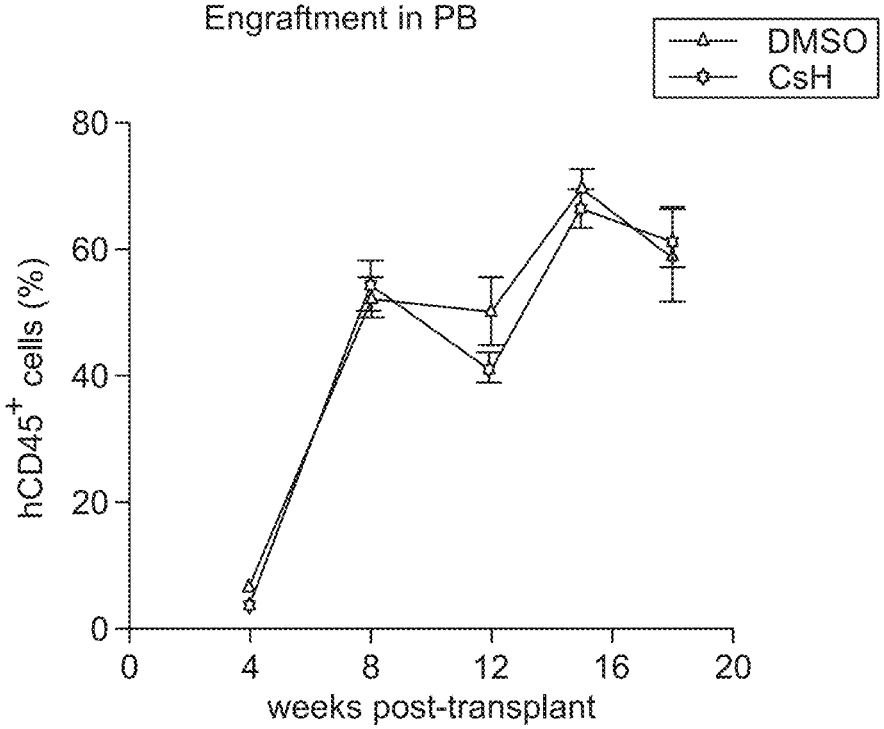
Figure 10:
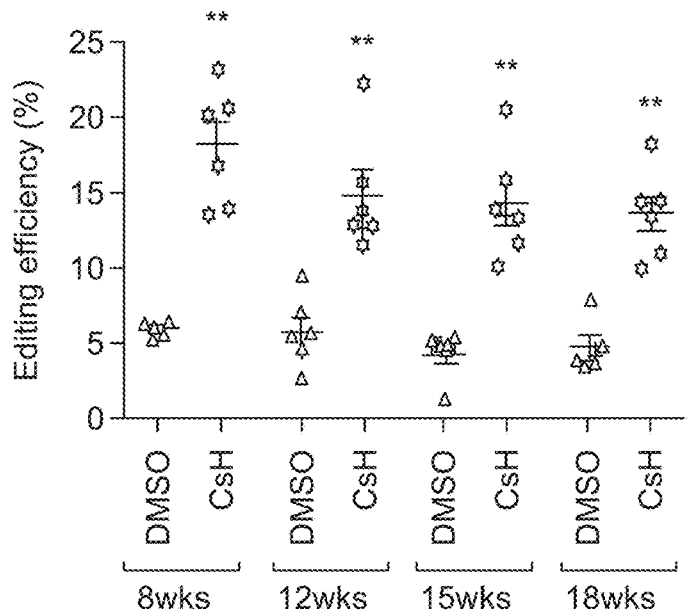
Figure 10:
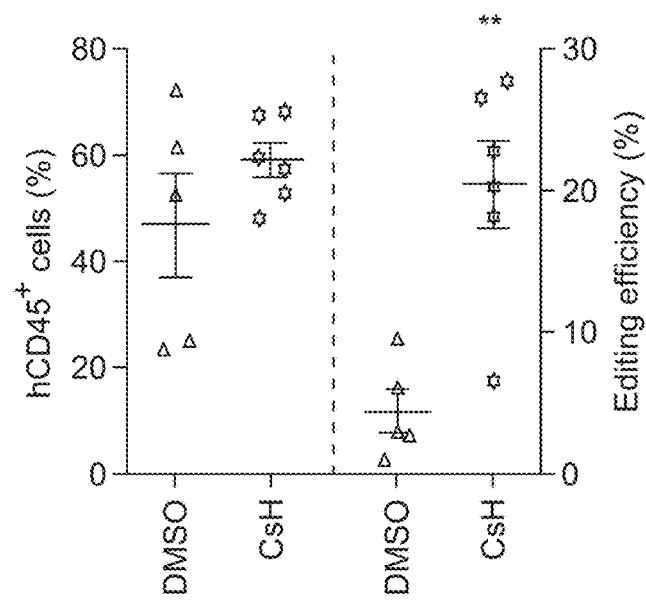
Figure 11:
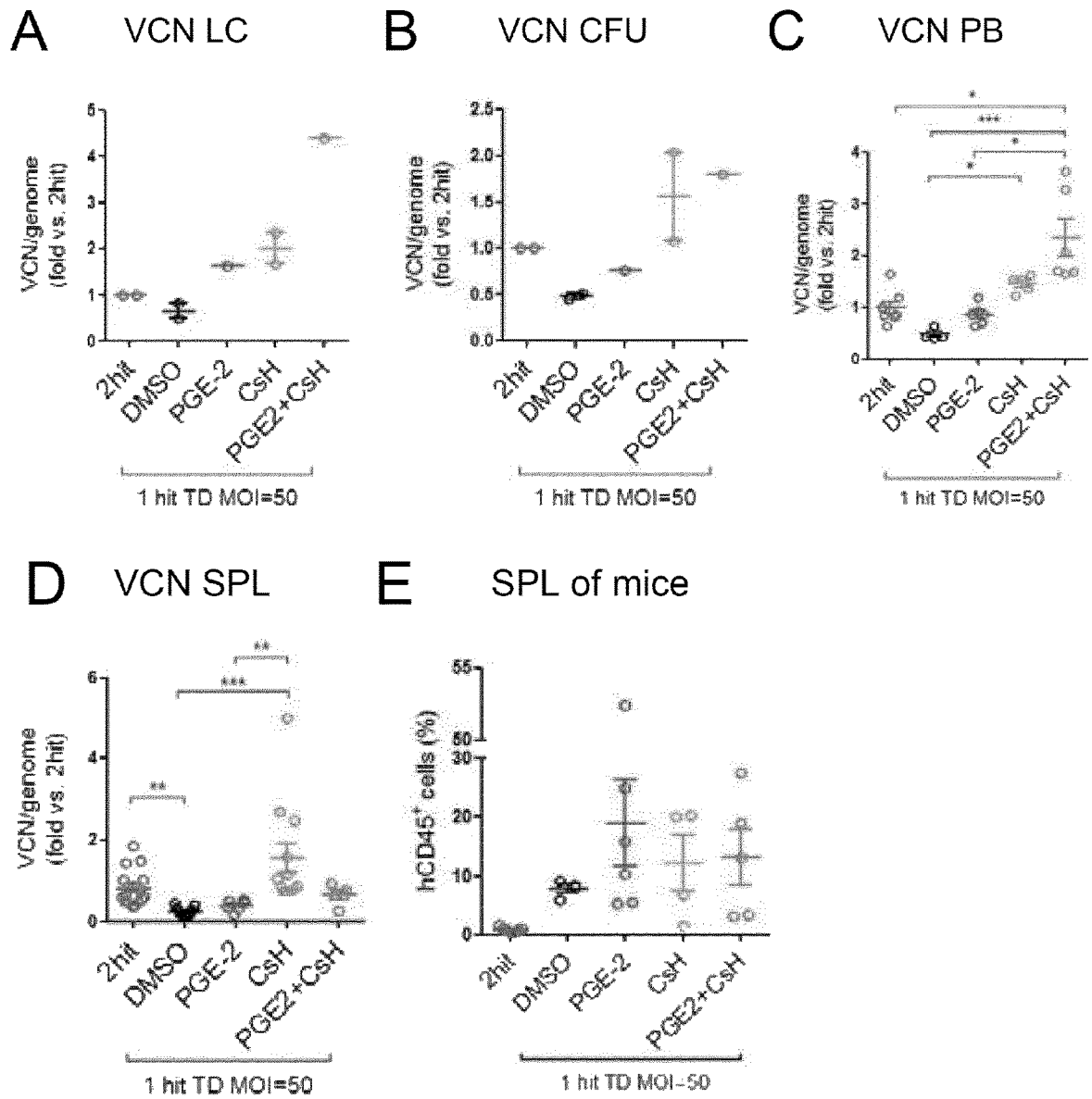
Figure 11:
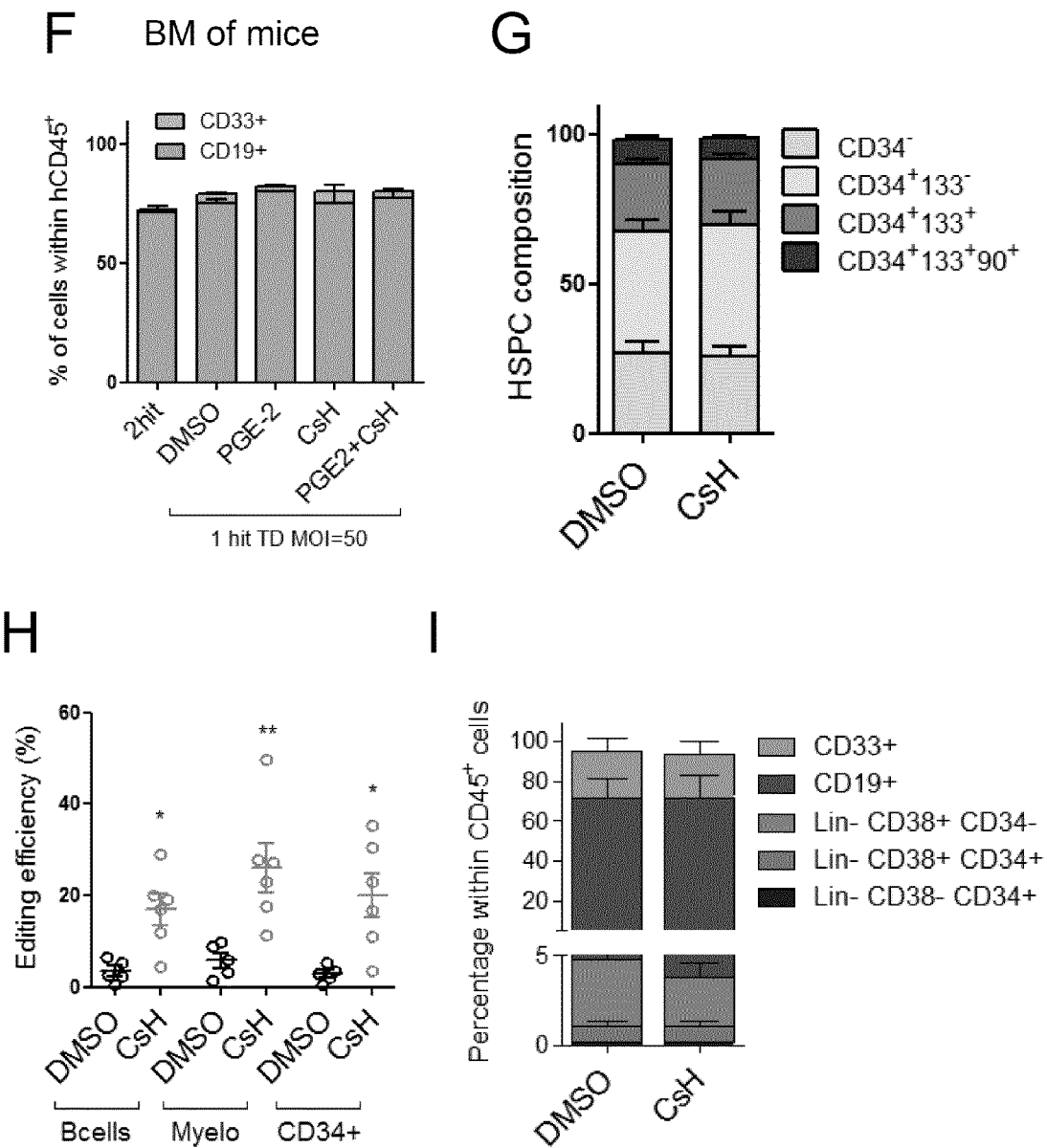

CsH increases LV transduction and gene editing efficiencies in SCID-repopulating HSPC. Human mPB-derived CD34⁺ cells were transduced with a clinical-grade LV comparing different transduction protocols. VCN/genome were measured in (A) liquid culture (LC) and (B) bulk CFU 14 days post-transduction (mean±SEM, n=2). (C) VCN/genome were measured in the peripheral blood (PB) of NSG-mice 8 weeks after transplantation (mean±SEM, n≥4, Dunn's adjusted Kruskal-Wallis test, *p<0.05, *p<0.001). (D) VCN and (E) engraftment levels of human CD45⁺ cells in the spleen (SPL) are shown 18 weeks post-transplant (mean±SEM, n≥6; Dunn's adjusted Kruskal-Wallis test, p<0.01, ***p<0.001). (F) Percentages of human B and myeloid cell linages (hCD19⁺ and hCD33⁺ respectively) within human CD45⁺ cells are shown in the bone marrow (BM) of mice at 18 weeks. (G) Subpopulation composition of treated human CB-CD34⁺ cells from FIG. 10J measured by flow cytometry 3 days after electroporation (n=7). (H) Editing efficiency measured by ddPCR in sorted CD34⁺ HSPCs, CD19⁺ B cells, and CD33⁺ myeloid cells from mice in FIG. 10K 19 weeks post-transplantation (Mann-Whitney Test). (1) Percentage of the indicated subpopulations measured within grafted human cells in the BM of mice from FIG. 10K.

FIG. 12

Cyclosporins counteract an IFN-inducible lentiviral restriction block also in HSPC. (A) THP-1 cells deleted for FPR1 were transduced with an LV at MOI 1+/−8 µM CsH. Transduction efficiencies were assessed by FACS 5 days post second transduction (mean±SEM, n=4, Mann Whitney test vs. each DMSO control, *p<0.05). (B) THP-1, (C) K562 and (D) CB-derived CD34⁺ cells were pre-stimulated with 1000 IU/mL of human IFNα for 24 hours followed by transduction only for human HSPC with LV at an MOI of 1 in the presence or absence of 8 µM CsA/H. Upregulation of selected IFN-stimulated genes (ISG) was assessed by RT-qPCR (mean±SEM, n=2-3).

DETAILED DESCRIPTION OF THE INVENTION

The terms "comprising", "comprises" and "comprised of" as used herein are synonymous with "including" or "includes"; or "containing" or "contains", and are inclusive or open-ended and do not exclude additional, non-recited members, elements or steps. The terms "comprising", "comprises" and "comprised of" also include the term "consisting of".

In one aspect, the invention provides use of cyclosporin H (CsH) or a derivative thereof for increasing the efficiency of transduction of an isolated population of cells by a viral vector and/or increasing the efficiency of gene editing of an isolated population of cells when transduced by a viral vector.

Increasing the efficiency of transduction refers to an increase in the transduction of the cells (e.g. haematopoietic stem and/or progenitor cells; or T cells) in the presence of an agent (e.g. CsH or a derivative thereof), in comparison to the transduction achieved in the absence of the agent but under otherwise substantially identical conditions. An increased efficiency of transduction may therefore allow the multiplicity of infection (MOI) and/or the transduction time required to achieve effective transduction to be reduced.

In one embodiment, the percentage of cells transduced by the vector is increased. In another embodiment, the vector copy number per cell is increased. Preferably both are achieved at the same time.

Methods for determining the percentage of cells transduced by a vector are known in the art. Suitable methods include flow cytometry, fluorescence-activated cell sorting (FACS) and fluorescence microscopy. The technique employed is preferably one which is amenable to automation and/or high throughput screening.

For example, a population of cells may be transduced with a vector which harbours a reporter gene. The vector may be constructed such that the reporter gene is expressed when the vector transduces a cell. Suitable reporter genes include genes encoding fluorescent proteins, for example green, yellow, cherry, cyan or orange fluorescent proteins. Once the population of cells has been transduced by the vector, both the number of cells expressing and not-expressing the reporter gene may be quantified using a suitable technique, such as FACS. The percentage of cells transduced by the vector may then be calculated.

Alternatively, quantitative PCR (qPCR) may be used to determine the percentage of cells transduced by a vector that does not harbour a reporter gene. For example, single colonies of cells (e.g. CD34+ cells) may be picked from a semi-solid culture and qPCR may be performed on each colony separately to determine the percentage of vector-positive colonies among those analysed.

Methods for determining vector copy number are also known in the art. The technique employed is preferably one which is amenable to automation and/or high throughput screening. Suitable techniques include quantitative PCR (qPCR) and Southern blot-based approaches.

Increasing the efficiency of gene editing may refer to an increase in the number of cells (e.g. haematopoietic stem and/or progenitor cells; or T cells) in which a target gene or site has been edited (e.g. disrupted, replaced, deleted or had a nucleic acid sequence inserted within or at it) in the intended manner following transduction of a population of cells with a viral vector in the presence of an agent (e.g. CsH or a derivative thereof), in comparison to that achieved in the absence of the agent but under otherwise substantially identical conditions. An increased efficiency of gene editing may therefore allow the multiplicity of infection (MOI) and/or the transduction time required to achieve effective gene editing to be reduced. Methods for determining whether a target gene or site has been edited are known in the art.

In the context of gene editing, for example using a CRISPR/Cas system, preferably the vector used to transduce the population of cells is a non-integrating vector (e.g. an integration-defective lentiviral vector, IDLV).

Cyclosporin H

Cyclosporin H (CsH, CAS No. 83602-39-5) is a cyclic undecapeptide having the following structure:

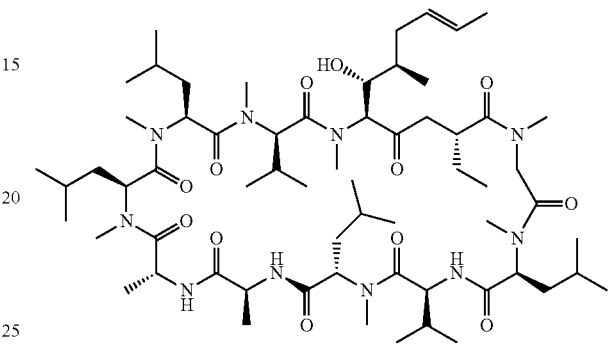

CsH is known to selectively antagonise the formyl peptide receptor, however unlike cyclosporin A (CsA), CsH does not bind cyclophilin to evoke immunosuppression. CsA mediates immunosuppression as a complex with the host peptidyl-prolyl isomerase cyclophilin A (CypA). This inhibits the $Ca^{2+}$-dependent phosphatase calcineurin and consequent activation of pro-inflammatory cytokines such as IL-2 (Sokolskaja, E. et al. (2006) Curr. Opin. Microbiol. 9: 404-8).

Solutions of CsH for use in the present invention may be prepared using routine methods known in the art.

The concentration at which CsH or a derivative thereof is applied to a population of cells may be adjusted for different vector systems to optimise transduction efficiency and/or gene editing. Methods for determining transduction efficiency and gene editing have been described above. A skilled person may therefore select a suitable concentration of CsH or a derivative thereof to maximise increase in transduction efficiency and/or gene editing while minimising any toxicity using the approaches described herein.

The present invention encompasses the use of CsH and derivatives of CsH. The CsH derivatives of the present invention are those which increase the efficiency of transduction of an isolated population of cells by a viral vector and/or increasing the efficiency of gene editing of an isolated population of cells when transduced by a viral vector.

CsH derivatives of the present invention may have been developed for increased solubility, increased stability and/or reduced toxicity.

CsH derivatives of the invention are preferably of low toxicity for mammals, in particular humans. Preferably, CsH derivatives of the invention are of low toxicity for haematopoietic stem and/or progenitor cells; and/or T cells.

Suitable CsH derivatives may be identified using methods known in the art for determining transduction efficiency and/or gene editing. For example, methods for determining the percentage of cells that are transduced by a vector, or methods for determining the vector copy number per cell may be employed. Such methods have been described above. The method employed is preferably one which is amenable to automation and/or high throughput screening of candidate CsH derivatives. The candidate CsH derivatives may form part of a library of CsH derivatives.

Rapamycin

Rapamycin (CAS No. 53123-88-9, also known as Sirolimus) is a macrolide produced by *Streptomyces hygroscopicus*. Rapamycin has the following structure:

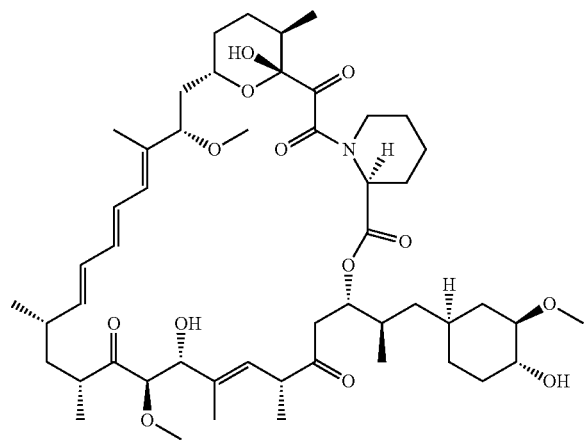

Rapamycin is an approved immunosuppressive agent for use in prevention of allograft rejection. Rapamycin exerts its immunosuppressive effect through binding and inhibition of the host peptidyl-prolyl isomerase FKBP12 (Harding, M. W. et al. (1989) Nature 341: 758-60; Siekierka, J. J. et al. (1989) Nature 341: 755-7).

By derivative of rapamycin, it is to be understood that rapamycin is modified by any of a number of techniques known in the art, preferably to improve properties such as stability and activity, while still retaining its function of increasing transduction efficiency and/or gene editing efficiency of an isolated population of cells.

Prostaglandin E2

Prostaglandin E2, which is also known as dinoprostone, is a naturally occurring prostaglandin having the structure:

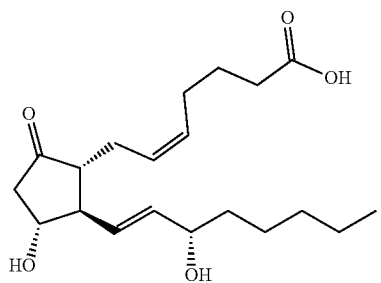 [SMILES: CCCCC[C@H](O)/C=C/[C@H]1[C@H](O)CC(=O)[C@@H]1C/C=C\CCCC(=O)O]

Prostaglandin E2 or a prostaglandin E2 derivative may be used, according to the invention in combination with CsH for increasing transduction efficiency and/or gene editing efficiency of an isolated population of cells.

In one embodiment, the prostaglandin E2 derivative is 16,16-dimethyl prostaglandin E2.

By derivative of prostaglandin E2, it is to be understood that prostaglandin E2 is modified by any of a number of techniques known in the art, preferably to improve properties such as stability and activity, while still retaining its function of increasing transduction efficiency and/or gene editing efficiency of an isolated population of cells.

Staurosporine

Staurosporine is a natural product originally isolated from *Streptomyces staurosporeus*. It displays activity as an inhibitor of protein kinases through the prevention of ATP binding to the kinase.

Haematopoietic Stem and Progenitor Cells

A stem cell is able to differentiate into many cell types. A cell that is able to differentiate into all cell types is known as totipotent. In mammals, only the zygote and early embryonic cells are totipotent. Stem cells are found in most, if not all, multicellular organisms. They are characterised by the ability to renew themselves through mitotic cell division and differentiate into a diverse range of specialised cell types. The two broad types of mammalian stem cells are embryonic stem cells that are isolated from the inner cell mass of blastocysts, and adult stem cells that are found in adult tissues. In a developing embryo, stem cells can differentiate into all of the specialised embryonic tissues. In adult organisms, stem cells and progenitor cells act as a repair system for the body, replenishing specialised cells, but also maintaining the normal turnover of regenerative organs, such as blood, skin or intestinal tissues.

Haematopoietic stem cells (HSCs) are multipotent stem cells that may be found, for example, in peripheral blood, bone marrow and umbilical cord blood. HSCs are capable of self-renewal and differentiation into any blood cell lineage. They are capable of recolonising the entire immune system, and the erythroid and myeloid lineages in all the haematopoietic tissues (such as bone marrow, spleen and thymus). They provide for life-long production of all lineages of haematopoietic cells.

Haematopoietic progenitor cells have the capacity to differentiate into a specific type of cell. In contrast to stem cells however, they are already far more specific: they are pushed to differentiate into their "target" cell. A difference between stem cells and progenitor cells is that stem cells can replicate indefinitely, whereas progenitor cells can only divide a limited number of times. Haematopoietic progenitor cells can be rigorously distinguished from HSCs only by functional in vivo assay (i.e. transplantation and demonstration of whether they can give rise to all blood lineages over prolonged time periods).

The haematopoietic stem and progenitor cells of the invention comprise the CD34 cell surface marker (denoted as CD34+).

Haematopoietic Stem and Progenitor Cell (HSPC) Source

A population of haematopoietic stem and/or progenitor cells may be obtained from a tissue sample.

For example, a population of haematopoietic stem and/or progenitor cells may be obtained from peripheral blood (e.g. adult and foetal peripheral blood), umbilical cord blood, bone marrow, liver or spleen. Preferably, these cells are obtained from peripheral blood or bone marrow. They may be obtained after mobilisation of the cells in vivo by means of growth factor treatment.

Mobilisation may be carried out using, for example, G-CSF, plerixaphor or combinations thereof. Other agents, such as NSAIDs and dipeptidyl peptidase inhibitors, may also be useful as mobilising agents.

With the availability of the stem cell growth factors GM-CSF and G-CSF, most haematopoietic stem cell transplantation procedures are now performed using stem cells collected from the peripheral blood, rather than from the bone marrow. Collecting peripheral blood stem cells provides a bigger graft, does not require that the donor be subjected to general anaesthesia to collect the graft, results in a shorter time to engraftment and may provide for a lower long-term relapse rate.

Bone marrow may be collected by standard aspiration methods (either steady-state or after mobilisation), or by using next-generation harvesting tools (e.g. Marrow Miner).

In addition, haematopoietic stem and progenitor cells may also be derived from induced pluripotent stem cells.

HSC Characteristics

HSCs are typically of low forward scatter and side scatter profile by flow cytometric procedures. Some are metabolically quiescent, as demonstrated by Rhodamine labelling which allows determination of mitochondrial activity. HSCs may comprise certain cell surface markers such as CD34, CD45, CD133, CD90 and CD49f. They may also be defined as cells lacking the expression of the CD38 and CD45RA cell surface markers. However, expression of some of these markers is dependent upon the developmental stage and tissue-specific context of the HSC. Some HSCs called "side population cells" exclude the Hoechst 33342 dye as detected by flow cytometry. Thus, HSCs have descriptive characteristics that allow for their identification and isolation.

Negative Markers

CD38 is the most established and useful single negative marker for human HSCs.

Human HSCs may also be negative for lineage markers such as CD2, CD3, CD14, CD16, CD19, CD20, CD24, CD36, CD56, CD66b, CD271 and CD45RA. However, these markers may need to be used in combination for HSC enrichment.

By "negative marker" it is to be understood that human HSCs lack the expression of these markers.

Positive Markers

CD34 and CD133 are the most useful positive markers for HSCs.

Some HSCs are also positive for lineage markers such as CD90, CD49f and CD93. However, these markers may need to be used in combination for HSC enrichment.

By "positive marker" it is to be understood that human HSCs express these markers.

In one embodiment, the haematopoietic stem and progenitor cells are CD34+CD38− cells.

Differentiated Cells

A differentiated cell is a cell which has become more specialised in comparison to a stem cell or progenitor cell. Differentiation occurs during the development of a multicellular organism as the organism changes from a single zygote to a complex system of tissues and cell types. Differentiation is also a common process in adults: adult stem cells divide and create fully-differentiated daughter cells during tissue repair and normal cell turnover. Differentiation dramatically changes a cell's size, shape, membrane potential, metabolic activity and responsiveness to signals. These changes are largely due to highly-controlled modifications in gene expression. In other words, a differentiated cell is a cell which has specific structures and performs certain functions due to a developmental process which involves the activation and deactivation of specific genes. Here, a differentiated cell includes differentiated cells of the haematopoietic lineage such as monocytes, macrophages, neutrophils, basophils, eosinophils, erythrocytes, megakaryocytes/platelets, dendritic cells, T cells, B-cells and NK-cells. For example, differentiated cells of the haematopoietic lineage can be distinguished from stem cells and progenitor cells by detection of cell surface molecules which are not expressed or are expressed to a lesser degree on undifferentiated cells. Examples of suitable human lineage markers include CD33, CD13, CD14, CD15 (myeloid), CD19, CD20, CD22, CD79a (B), CD36, CD71, CD235a (erythroid), CD2, CD3, CD4, CD8 (T) and CD56 (NK).

T Cells

T cells (or T lymphocytes) are a type of lymphocyte that play a central role in cell-mediated immunity. They can be distinguished from other lymphocytes, such as B cells and natural killer cells (NK cells), by the presence of a T-cell receptor (TCR) on the cell surface.

In one embodiment, the T cells are CD4+ T cells. In another embodiment, the T cells are CD3+ T cells.

Isolation and Enrichment of Populations of Cells

The term "isolated population" of cells as used herein may refer to the population of cells having been previously removed from the body. An isolated population of cells may be cultured and manipulated ex vivo or in vitro using standard techniques known in the art. An isolated population of cells may later be reintroduced into a subject. Said subject may be the same subject from which the cells were originally isolated or a different subject.

A population of cells may be purified selectively for cells that exhibit a specific phenotype or characteristic, and from other cells which do not exhibit that phenotype or characteristic, or exhibit it to a lesser degree. For example, a population of cells that expresses a specific marker (such as CD34) may be purified from a starting population of cells. Alternatively, or in addition, a population of cells that does not express another marker (such as CD38) may be purified.

By "enriching" a population of cells for a certain type of cells it is to be understood that the concentration of that type of cells is increased within the population. The concentration of other types of cells may be concomitantly reduced.

Purification or enrichment may result in the population of cells being substantially pure of other types of cell.

Purifying or enriching for a population of cells expressing a specific marker (e.g. CD34 or CD38) may be achieved by using an agent that binds to that marker, preferably substantially specifically to that marker.

An agent that binds to a cellular marker may be an antibody, for example an anti-CD34 or anti-CD38 antibody.

The term "antibody" refers to complete antibodies or antibody fragments capable of binding to a selected target, and including Fv, ScFv, F(ab') and F(ab')$_2$, monoclonal and polyclonal antibodies, engineered antibodies including chimeric, CDR-grafted and humanised antibodies, and artificially selected antibodies produced using phage display or alternative techniques.

In addition, alternatives to classical antibodies may also be used in the invention, for example "avibodies", "avimers", "anticalins", "nanobodies" and "DARPins".

The agents that bind to specific markers may be labelled so as to be identifiable using any of a number of techniques known in the art. The agent may be inherently labelled, or may be modified by conjugating a label thereto. By "conjugating" it is to be understood that the agent and label are operably linked. This means that the agent and label are linked together in a manner which enables both to carry out their function (e.g. binding to a marker, allowing fluorescent identification or allowing separation when placed in a magnetic field) substantially unhindered. Suitable methods of conjugation are well known in the art and would be readily identifiable by the skilled person.

A label may allow, for example, the labelled agent and any cell to which it is bound to be purified from its environment (e.g. the agent may be labelled with a magnetic bead or an affinity tag, such as avidin), detected or both. Detectable markers suitable for use as a label include fluorophores (e.g.

green, cherry, cyan and orange fluorescent proteins) and peptide tags (e.g. His tags, Myc tags, FLAG tags and HA tags).

A number of techniques for separating a population of cells expressing a specific marker are known in the art. These include magnetic bead-based separation technologies (e.g. closed-circuit magnetic bead-based separation), flow cytometry, fluorescence-activated cell sorting (FACS), affinity tag purification (e.g. using affinity columns or beads, such biotin columns to separate avidin-labelled agents) and microscopy-based techniques.

It may also be possible to perform the separation using a combination of different techniques, such as a magnetic bead-based separation step followed by sorting of the resulting population of cells for one or more additional (positive or negative) markers by flow cytometry.

Clinical grade separation may be performed, for example, using the CliniMACS® system (Miltenyi). This is an example of a closed-circuit magnetic bead-based separation technology.

It is also envisaged that dye exclusion properties (e.g. side population or rhodamine labelling) or enzymatic activity (e.g. ALDH activity) may be used to enrich for haematopoietic stem cells.

Gene Editing

The term "gene editing" refers to a type of genetic engineering in which a nucleic acid is inserted, deleted or replaced in a cell. Gene editing may be achieved using engineered nucleases, which may be targeted to a desired site in a polynucleotide (e.g. a genome). Such nucleases may create site-specific double-strand breaks at desired locations, which may then be repaired through non-homologous end-joining (NHEJ) or homologous recombination (HR), resulting in targeted mutations.

Such nucleases may be delivered to a target cell using viral vectors. The present invention provides methods of increasing the efficiency of the gene editing process.

Examples of suitable nucleases known in the art include zinc finger nucleases (ZFNs), transcription activator like effector nucleases (TALENs), and the clustered regularly interspaced short palindromic repeats (CRISPR)/Cas system (Gaj, T. et al. (2013) Trends Biotechnol. 31: 397-405; Sander, J. D. et al. (2014) Nat. Biotechnol. 32: 347-55).

Meganucleases (Silve, G. et al. (2011) Cur. Gene Ther. 11: 11-27) may also be employed as suitable nucleases for gene editing.

The CRISPR/Cas system is an RNA-guided DNA binding system (van der Oost et al. (2014) Nat. Rev. Microbiol. 12: 479-92), wherein the guide RNA (gRNA) may be selected to enable a Cas9 domain to be targeted to a specific sequence. Methods for the design of gRNAs are known in the art. Furthermore, fully orthogonal Cas9 proteins, as well as Cas9/gRNA ribonucleoprotein complexes and modifications of the gRNA structure/composition to bind different proteins, have been recently developed to simultaneously and directionally target different effector domains to desired genomic sites of the cells (Esvelt et al. (2013) Nat. Methods 10: 1116-21; Zetsche, B. et al. (2015) Cell pii: S0092-8674 (15)01200-3; Dahlman, J. E. et al. (2015) Nat. Biotechnol. 2015 Oct. 5. doi: 10.1038/nbt.3390. [Epub ahead of print]; Zalatan, J. G. et al. (2015) Cell 160: 339-50; Paix, A. et al. (2015) Genetics 201: 47-54), and are suitable for use in the invention.

Vectors

A vector is a tool that allows or facilitates the transfer of an entity from one environment to another. The vectors used to transduce the cells in the present invention are viral vectors.

In one embodiment, the viral vectors are retroviral vectors. In a preferred embodiment, the viral vectors are lentiviral vectors.

In one embodiment, the lentiviral vectors are derived from HIV-1, HIV-2, SIV, FIV, BIV, EIAV, CAEV or visna lentivirus.

In one embodiment, the viral vector is a gamma-retroviral vector.

By "vector derived from" a certain type of virus, it is to be understood that the vector comprises at least one component part derivable from that type of virus.

Retroviral and Lentiviral Vectors

A retroviral vector may be derived from or may be derivable from any suitable retrovirus. A large number of different retroviruses have been identified. Examples include murine leukaemia virus (MLV), human T cell leukaemia virus (HTLV), mouse mammary tumour virus (MMTV), Rous sarcoma virus (RSV), Fujinami sarcoma virus (FuSV), Moloney murine leukaemia virus (Mo-MLV), FBR murine osteosarcoma virus (FBR MSV), Moloney murine sarcoma virus (Mo-MSV), Abelson murine leukaemia virus (A-MLV), avian myelocytomatosis virus-29 (MC29) and avian erythroblastosis virus (AEV). A detailed list of retroviruses may be found in Coffin, J. M. et al. (1997) Retroviruses, Cold Spring Harbour Laboratory Press, 758-63.

Retroviruses may be broadly divided into two categories, "simple" and "complex". Retroviruses may be even further divided into seven groups. Five of these groups represent retroviruses with oncogenic potential. The remaining two groups are the lentiviruses and the spumaviruses. A review of these retroviruses is presented in Coffin, J. M. et al. (1997) Retroviruses, Cold Spring Harbour Laboratory Press, 758-63.

The basic structure of retrovirus and lentivirus genomes share many common features such as a 5' LTR and a 3' LTR. Between or within these are located a packaging signal to enable the genome to be packaged, a primer binding site, integration sites to enable integration into a host cell genome, and gag, pol and env genes encoding the packaging components—these are polypeptides required for the assembly of viral particles. Lentiviruses have additional features, such as rev and RRE sequences in HIV, which enable the efficient export of RNA transcripts of the integrated provirus from the nucleus to the cytoplasm of an infected target cell.

In the provirus, these genes are flanked at both ends by regions called long terminal repeats (LTRs). The LTRs are responsible for proviral integration and transcription. LTRs also serve as enhancer-promoter sequences and can control the expression of the viral genes.

The LTRs themselves are identical sequences that can be divided into three elements: U3, R and U5. U3 is derived from the sequence unique to the 3' end of the RNA. R is derived from a sequence repeated at both ends of the RNA. U5 is derived from the sequence unique to the 5' end of the RNA. The sizes of the three elements can vary considerably among different retroviruses.

In a defective retroviral vector genome gag, pol and env may be absent or not functional.

In a typical retroviral vector, at least part of one or more protein coding regions essential for replication may be removed from the virus. This makes the viral vector replication-defective. Portions of the viral genome may also be replaced by a library encoding candidate modulating moieties operably linked to a regulatory control region and a reporter moiety in the vector genome in order to generate a vector comprising candidate modulating moieties which is capable of transducing a target host cell and/or integrating its genome into a host genome.

Lentivirus vectors are part of the larger group of retroviral vectors. A detailed list of lentiviruses may be found in Coffin, J. M. et al. (1997) Retroviruses, Cold Spring Harbour Laboratory Press, 758-63. In brief, lentiviruses can be divided into primate and non-primate groups. Examples of primate lentiviruses include but are not limited to human immunodeficiency virus (HIV), the causative agent of human acquired immunodeficiency syndrome (AIDS); and simian immunodeficiency virus (SIV). Examples of non-primate lentiviruses include the prototype "slow virus" visna/maedi virus (VMV), as well as the related caprine arthritis-encephalitis virus (CAEV), equine infectious anaemia virus (EIAV), and the more recently described feline immunodeficiency virus (FIV) and bovine immunodeficiency virus (BIV).

The lentivirus family differs from retroviruses in that lentiviruses have the capability to infect both dividing and non-dividing cells (Lewis, P et al. (1992) EMBO J. 11: 3053-8; Lewis, P. F. et al. (1994) J. Virol. 68: 510-6). In contrast, other retroviruses, such as MLV, are unable to infect non-dividing or slowly dividing cells such as those that make up, for example, muscle, brain, lung and liver tissue.

A lentiviral vector, as used herein, is a vector which comprises at least one component part derivable from a lentivirus. Preferably, that component part is involved in the biological mechanisms by which the vector infects cells, expresses genes or is replicated.

The lentiviral vector may be a "primate" vector. The lentiviral vector may be a "non-primate" vector (i.e. derived from a virus which does not primarily infect primates, especially humans). Examples of non-primate lentiviruses may be any member of the family of lentiviridae which does not naturally infect a primate.

As examples of lentivirus-based vectors, HIV-1- and HIV-2-based vectors are described below.

The HIV-1 vector contains cis-acting elements that are also found in simple retroviruses. It has been shown that sequences that extend into the gag open reading frame are important for packaging of HIV-1. Therefore, HIV-1 vectors often contain the relevant portion of gag in which the translational initiation codon has been mutated. In addition, most HIV-1 vectors also contain a portion of the env gene that includes the RRE. Rev binds to RRE, which permits the transport of full-length or singly spliced mRNAs from the nucleus to the cytoplasm. In the absence of Rev and/or RRE, full-length HIV-1 RNAs accumulate in the nucleus. Alternatively, a constitutive transport element from certain simple retroviruses such as Mason-Pfizer monkey virus can be used to relieve the requirement for Rev and RRE. Efficient transcription from the HIV-1 LTR promoter requires the viral protein Tat.

Most HIV-2-based vectors are structurally very similar to HIV-1 vectors. Similar to HIV-1-based vectors, HIV-2 vectors also require RRE for efficient transport of the full-length or singly spliced viral RNAs.

In one system, the vector and helper constructs are from two different viruses, and the reduced nucleotide homology may decrease the probability of recombination. In addition to vectors based on the primate lentiviruses, vectors based on FIV have also been developed as an alternative to vectors derived from the pathogenic HIV-1 genome. The structures of these vectors are also similar to the HIV-1 based vectors.

Preferably the viral vector used in the present invention has a minimal viral genome.

By "minimal viral genome" it is to be understood that the viral vector has been manipulated so as to remove the non-essential elements and to retain the essential elements in order to provide the required functionality to infect, transduce and deliver a nucleotide sequence of interest to a target host cell. Further details of this strategy can be found in WO 1998/017815.

Preferably the plasmid vector used to produce the viral genome within a host cell/packaging cell will have sufficient lentiviral genetic information to allow packaging of an RNA genome, in the presence of packaging components, into a viral particle which is capable of infecting a target cell, but is incapable of independent replication to produce infectious viral particles within the final target cell. Preferably the vector lacks a functional gag-pol and/or env gene and/or other genes essential for replication.

However, the plasmid vector used to produce the viral genome within a host cell/packaging cell will also include transcriptional regulatory control sequences operably linked to the lentiviral genome to direct transcription of the genome in a host cell/packaging cell. These regulatory sequences may be the natural sequences associated with the transcribed viral sequence (i.e. the 5' U3 region), or they may be a heterologous promoter, such as another viral promoter (e.g. the CMV promoter).

The vectors may be self-inactivating (SIN) vectors in which the viral enhancer and promoter sequences have been deleted. SIN vectors can be generated and transduce non-dividing cells in vivo with an efficacy similar to that of wild-type vectors. The transcriptional inactivation of the long terminal repeat (LTR) in the SIN provirus should prevent mobilisation by replication-competent virus. This should also enable the regulated expression of genes from internal promoters by eliminating any cis-acting effects of the LTR.

The vectors may be integration-defective. Integration defective lentiviral vectors (IDLVs) can be produced, for example, either by packaging the vector with catalytically inactive integrase (such as an HIV integrase bearing the D64V mutation in the catalytic site; Naldini, L. et al. (1996) Science 272: 263-7; Naldini, L. et al. (1996) Proc. Natl. Acad. Sci. USA 93: 11382-8; Leavitt, A. D. et al. (1996) J. Virol. 70: 721-8) or by modifying or deleting essential att sequences from the vector LTR (Nightingale, S. J. et al. (2006) Mol. Ther. 13: 1121-32), or by a combination of the above.

HIV-Derived Vectors

HIV-derived vectors for use in the present invention are not particularly limited in terms of HIV strain. Numerous examples of sequences of HIV strains may be found at the HIV Sequence Database (http://www.hiv.lanl.gov/content/index).

For example, a HIV-1-derived vector may be derived from any of the HIV-1 strains NL4-3, IllB_LAI or HXB2_LAI (X4-tropic), or BAL (R5-tropic), or a chimaera thereof. Preferably, HIV-1-derived vectors are derived from the pMDLg/pRRE Gag-Pol-expressing packaging construct (U.S. Pat. Nos. 7,629,153; 8,652,837; Naldini, L. et al. (1996) Science 272: 263-7; Follenzi, A. et al. (2002) Methods Enzymol. 346: 454-65).

A HIV-2-derived vector may be derived, for example, from the HIV-2 strain ROD.

Nucleotide of Interest

The vector used in the present invention preferably comprises a nucleotide of interest.

Preferably the nucleotide of interest gives rise to a therapeutic effect.

Suitable NOIs include, but are not limited to sequences encoding enzymes, cytokines, chemokines, hormones, antibodies, anti-oxidant molecules, engineered immunoglobulin-like molecules, single chain antibodies, fusion proteins, immune co-stimulatory molecules, immunomodulatory molecules, anti-sense RNA, microRNA, shRNA, siRNA, guide RNA (gRNA, e.g. used in connection with a CRISPR/Cas system), ribozymes, miRNA target sequences, a transdomain negative mutant of a target protein, toxins, conditional toxins, antigens, tumour suppressor proteins, growth factors, transcription factors, membrane proteins, surface receptors, anti-cancer molecules, vasoactive proteins and peptides, anti-viral proteins and ribozymes, and derivatives thereof (such as derivatives with an associated reporter group). The NOIs may also encode pro-drug activating enzymes.

An example of a NOI is the beta-globin chain which may be used for gene therapy of thalassemia/sickle cell disease.

NOIs also include those useful for the treatment of other diseases requiring non-urgent/elective gene correction in the myeloid lineage such as: chronic granulomatous disease (CGD, e.g. the gp91phox transgene), leukocyte adhesion defects, other phagocyte disorders in patients without ongoing severe infections and inherited bone marrow failure syndromes (e.g. Fanconi anaemia), as well as primary immunodeficiencies (SCIDs).

NOIs also include those useful in the treatment of lysosomal storage disorders and immunodeficiencies.

The applicability of the invention to T cells also facilitates its application in cell therapies that are based on infusion of modified T cells into patients, including anti-cancer strategies (such as using engineered CAR-T cells) and approaches based on infusion of universal donor T cells. NOIs may therefore also include, for example, chimeric antigen receptors (CARs).

Pharmaceutical Composition

The cells of the invention may be formulated for administration to subjects with a pharmaceutically acceptable carrier, diluent or excipient. Suitable carriers and diluents include isotonic saline solutions, for example phosphate-buffered saline, and potentially contain human serum albumin.

Handling of the cell therapy product is preferably performed in compliance with FACT-JACIE International Standards for cellular therapy.

Haematopoietic Stem and/or Progenitor Cell Transplantation

The present invention provides a population of cells, for example a population of haematopoietic stem and/or progenitor cells, or a population of T cells, prepared according to a method of the invention for use in therapy, for example for use in gene therapy.

The use may be as part of a cell transplantation procedure, for example a haematopoietic stem and/or progenitor cell transplantation procedure.

Haematopoietic stem cell transplantation (HSCT) is the transplantation of blood stem cells derived from the bone marrow (in this case known as bone marrow transplantation) or blood. Stem cell transplantation is a medical procedure in the fields of haematology and oncology, most often performed for people with diseases of the blood or bone marrow, or certain types of cancer.

Many recipients of HSCTs are multiple myeloma or leukaemia patients who would not benefit from prolonged treatment with, or are already resistant to, chemotherapy. Candidates for HSCTs include paediatric cases where the patient has an inborn defect such as severe combined immunodeficiency or congenital neutropenia with defective stem cells, and also children or adults with aplastic anaemia who have lost their stem cells after birth. Other conditions treated with stem cell transplants include sickle-cell disease, myelodysplastic syndrome, neuroblastoma, lymphoma, Ewing's Sarcoma, Desmoplastic small round cell tumour and Hodgkin's disease. More recently non-myeloablative, or so-called "mini transplant", procedures have been developed that require smaller doses of preparative chemotherapy and radiation. This has allowed HSCT to be conducted in the elderly and other patients who would otherwise be considered too weak to withstand a conventional treatment regimen.

In one embodiment, a population of haematopoietic stem and/or progenitor cells prepared according to a method of the invention is administered as part of an autologous stem cell transplant procedure.

In another embodiment, a population of haematopoietic stem and/or progenitor cells prepared according to a method of the invention is administered as part of an allogeneic stem cell transplant procedure.

The term "autologous stem cell transplant procedure" as used herein refers to a procedure in which the starting population of cells (which are then transduced according to a method of the invention) is obtained from the same subject as that to which the transduced cell population is administered. Autologous transplant procedures are advantageous as they avoid problems associated with immunological incompatibility and are available to subjects irrespective of the availability of a genetically matched donor.

The term "allogeneic stem cell transplant procedure" as used herein refers to a procedure in which the starting population of cells (which are then transduced according to a method of the invention) is obtained from a different subject as that to which the transduced cell population is administered. Preferably, the donor will be genetically matched to the subject to which the cells are administered to minimise the risk of immunological incompatibility.

Suitable doses of transduced cell populations are such as to be therapeutically and/or prophylactically effective. The dose to be administered may depend on the subject and condition to be treated, and may be readily determined by a skilled person.

Haematopoietic progenitor cells provide short term engraftment. Accordingly, gene therapy by administering transduced haematopoietic progenitor cells would provide a non-permanent effect in the subject. For example, the effect may be limited to 1-6 months following administration of the transduced haematopoietic progenitor cells. An advantage of this approach would be better safety and tolerability, due to the self-limited nature of the therapeutic intervention.

Such haematopoietic progenitor cell gene therapy may be suited to treatment of acquired disorders, for example cancer, where time-limited expression of a (potentially toxic) anti-cancer nucleotide of interest may be sufficient to eradicate the disease.

The invention may be useful in the treatment of the disorders listed in WO 1998/005635. For ease of reference, part of that list is now provided: cancer, inflammation or inflammatory disease, dermatological disorders, fever, cardiovascular effects, haemorrhage, coagulation and acute phase response, cachexia, anorexia, acute infection, HIV infection, shock states, graft-versus-host reactions, autoimmune disease, reperfusion injury, meningitis, migraine and aspirin-dependent anti-thrombosis; tumour growth, invasion and spread, angiogenesis, metastases, malignant, ascites and malignant pleural effusion; cerebral ischaemia, ischaemic heart disease, osteoarthritis, rheumatoid arthritis, osteoporosis, asthma, multiple sclerosis, neurodegeneration, Alzheimer's disease, atherosclerosis, stroke, vasculitis, Crohn's disease and ulcerative colitis; periodontitis, gingivitis; psoriasis, atopic dermatitis, chronic ulcers, epidermolysis bullosa; corneal ulceration, retinopathy and surgical wound healing; rhinitis, allergic conjunctivitis, eczema, anaphylaxis; restenosis, congestive heart failure, endometriosis, atherosclerosis or endosclerosis.

In addition, or in the alternative, the invention may be useful in the treatment of the disorders listed in WO 1998/007859. For ease of reference, part of that list is now provided: cytokine and cell proliferation/differentiation activity; immunosuppressant or immunostimulant activity (e.g. for treating immune deficiency, including infection with human immune deficiency virus; regulation of lymphocyte growth; treating cancer and many autoimmune diseases, and to prevent transplant rejection or induce tumour immunity); regulation of haematopoiesis, e.g. treatment of myeloid or lymphoid diseases; promoting growth of bone, cartilage, tendon, ligament and nerve tissue, e.g. for healing wounds, treatment of burns, ulcers and periodontal disease and neurodegeneration; inhibition or activation of follicle-stimulating hormone (modulation of fertility); chemotactic/chemokinetic activity (e.g. for mobilising specific cell types to sites of injury or infection); haemostatic and thrombolytic activity (e.g. for treating haemophilia and stroke); anti-inflammatory activity (for treating e.g. septic shock or Crohn's disease); as antimicrobials; modulators of e.g. metabolism or behaviour; as analgesics; treating specific deficiency disorders; in treatment of e.g. psoriasis, in human or veterinary medicine.

In addition, or in the alternative, the invention may be useful in the treatment of the disorders listed in WO 1998/009985. For ease of reference, part of that list is now provided: macrophage inhibitory and/or T cell inhibitory activity and thus, anti-inflammatory activity; anti-immune activity, i.e. inhibitory effects against a cellular and/or humoral immune response, including a response not associated with inflammation; inhibit the ability of macrophages and T cells to adhere to extracellular matrix components and fibronectin, as well as up-regulated fas receptor expression in T cells; inhibit unwanted immune reaction and inflammation including arthritis, including rheumatoid arthritis, inflammation associated with hypersensitivity, allergic reactions, asthma, systemic lupus erythematosus, collagen diseases and other autoimmune diseases, inflammation associated with atherosclerosis, arteriosclerosis, atherosclerotic heart disease, reperfusion injury, cardiac arrest, myocardial infarction, vascular inflammatory disorders, respiratory distress syndrome or other cardiopulmonary diseases, inflammation associated with peptic ulcer, ulcerative colitis and other diseases of the gastrointestinal tract, hepatic fibrosis, liver cirrhosis or other hepatic diseases, thyroiditis or other glandular diseases, glomerulonephritis or other renal and urologic diseases, otitis or other oto-rhino-laryngological diseases, dermatitis or other dermal diseases, periodontal diseases or other dental diseases, orchitis or epididimo-orchitis, infertility, orchidal trauma or other immune-related testicular diseases, placental dysfunction, placental insufficiency, habitual abortion, eclampsia, pre-eclampsia and other immune and/or inflammatory-related gynaecological diseases, posterior uveitis, intermediate uveitis, anterior uveitis, conjunctivitis, chorioretinitis, uveoretinitis, optic neuritis, intraocular inflammation, e.g. retinitis or cystoid macular oedema, sympathetic ophthalmia, scleritis, retinitis pigmentosa, immune and inflammatory components of degenerative fondus disease, inflammatory components of ocular trauma, ocular inflammation caused by infection, proliferative vitreo-retinopathies, acute ischaemic optic neuropathy, excessive scarring, e.g. following glaucoma filtration operation, immune and/or inflammation reaction against ocular implants and other immune and inflammatory-related ophthalmic diseases, inflammation associated with autoimmune diseases or conditions or disorders where, both in the central nervous system (CNS) or in any other organ, immune and/or inflammation suppression would be beneficial, Parkinson's disease, complication and/or side effects from treatment of Parkinson's disease, AIDS-related dementia complex HIV-related encephalopathy, Devic's disease, Sydenham chorea, Alzheimer's disease and other degenerative diseases, conditions or disorders of the CNS, inflammatory components of stokes, post-polio syndrome, immune and inflammatory components of psychiatric disorders, myelitis, encephalitis, subacute sclerosing pan-encephalitis, encephalomyelitis, acute neuropathy, subacute neuropathy, chronic neuropathy, Guillaim-Barre syndrome, Sydenham chora, myasthenia gravis, pseudo-tumour cerebri, Down's Syndrome, Huntington's disease, amyotrophic lateral sclerosis, inflammatory components of CNS compression or CNS trauma or infections of the CNS, inflammatory components of muscular atrophies and dystrophies, and immune and inflammatory related diseases, conditions or disorders of the central and peripheral nervous systems, post-traumatic inflammation, septic shock, infectious diseases, inflammatory complications or side effects of surgery, bone marrow transplantation or other transplantation complications and/or side effects, inflammatory and/or immune complications and side effects of gene therapy, e.g. due to infection with a viral carrier, or inflammation associated with AIDS, to suppress or inhibit a humoral and/or cellular immune response, to treat or ameliorate monocyte or leukocyte proliferative diseases, e.g. leukaemia, by reducing the amount of monocytes or lymphocytes, for the prevention and/or treatment of graft rejection in cases of transplantation of natural or artificial cells, tissue and organs such as cornea, bone marrow, organs, lenses, pacemakers, natural or artificial skin tissue.

In addition, or in the alternative, the invention may be useful in the treatment of β-thalassemia, chronic granulomatous disease, metachromatic leukodystrophy, mucopolysaccharidoses disorders and other lysosomal storage disorders.

As mentioned above, the applicability of the invention to T cells also facilitates its application in cell therapies that are based on infusion of modified T cells into patients, including anti-cancer strategies (such as using engineered CAR-T cells) and approaches based on infusion of universal donor T cells. Thus, in addition, or in the alternative, the invention may be useful in the prevention of graft-versus-host disease.

Kit

In another aspect, the present invention provides a kit comprising CsH or a derivative thereof and/or cell populations of the invention.

The CsH or a derivative thereof, and/or cell populations may be provided in suitable containers.

The kit may also include instructions for use.

Method of Treatment

It is to be appreciated that all references herein to treatment include curative, palliative and prophylactic treatment; although in the context of the invention references to preventing are more commonly associated with prophylactic treatment. The treatment of mammals, particularly humans, is preferred. Both human and veterinary treatments are within the scope of the invention.

The skilled person will understand that they can combine all features of the invention disclosed herein without departing from the scope of the invention as disclosed.

Preferred features and embodiments of the invention will now be described by way of non-limiting examples.

The practice of the present invention will employ, unless otherwise indicated, conventional techniques of chemistry, biochemistry, molecular biology, microbiology and immunology, which are within the capabilities of a person of ordinary skill in the art. Such techniques are explained in the literature. See, for example, Sambrook, J., Fritsch, E. F. and Maniatis, T. (1989) Molecular Cloning: A Laboratory Manual, 2nd Edition, Cold Spring Harbor Laboratory Press; Ausubel, F. M. et al. (1995 and periodic supplements) Current Protocols in Molecular Biology, Ch. 9, 13 and 16, John Wiley & Sons; Roe, B., Crabtree, J. and Kahn, A. (1996) DNA Isolation and Sequencing: Essential Techniques, John Wiley & Sons; Polak, J. M. and McGee, J. O'D. (1990) In Situ Hybridization: Principles and Practice, Oxford University Press; Gait, M. J. (1984) Oligonucleotide Synthesis: A Practical Approach, IRL Press; and Lilley, D. M. and Dahlberg, J. E. (1992) Methods in Enzymology: DNA Structures Part A: Synthesis and Physical Analysis of DNA, Academic Press. Each of these general texts is herein incorporated by reference.

EXAMPLES

Example 1

Materials and Methods

Vectors

Third generation lentivirus (LV) stocks were prepared, concentrated and titered as previously described (Dull, T. et al. (1998) J Virol 72: 8463-8471; Follenzi, A. et al. (2000) Nat Genet 25: 217-222). Briefly, self-inactivating (SIN) LV vectors were produced using the transfer vector pCCLsin.cPPT.hPGK.eGFP.Wpre, the packaging plasmid pMDLg/pRRE, Rev-expressing pCMV-Rev and the VSV-g envelope-encoding pMD2.VSV-G plasmids. Integrase-defective lentiviral vector (IDLV) was produced as previoulsly described (Lombardo, A. et al. (2007) Nat Biotechnol 25: 1298-1306) substituting the packaging plasmid pMDLg/pRRE with pMD.Lg/pRRE.D64Vlnt. Bald vector, a normal LV produced omitting the Env-encoding plasmid during vector production, was produced as a negative control. During vector production, the Env construct was substituted by pcDNA3.1 (Invitrogen Inc.). For SINLV capsid mutants, vectors were produced as described above, except that the wild-type pMDLg/pRRE was replaced with a packaging plasmid harbouring a specific point-mutation in the p24 coding region as follows: pMDLg/pRRE-N74D; pMDLg/pRRE-P90A. All modified packaging plasmids were purchased from GenScript Inc. For pseudotyping LVs with the mutant baboon retrovirus envelope, pMD2.VSV-G was replaced by the BaEV-TR during vector production as previously described (Girard-Gagnepain, A. et al. (2014) Blood 124: 1221-1231). The SIN-retroviral vector (SIN-RV) was produced as previously described (Montini, E. et al. (2006) Nat Biotechnol 24: 687-696) using as transfer vector RVrkat43.2MLV GFP, the packaging plasmid pCM-gag-pol and the VSV-g envelope-encoding pMD2.VSV-G plasmid or pseudotyped with the amphotropic envelope glycoprotein (AmphoRV). Simian immunodeficiency vector (SIV) was produced as previously described (Mangeot, P. E. et al. (2002) Mol Ther 5: 283-290) using an SIV-GFP transfer vector, SIV3+ packaging plasmid and VSV-G pseudotyped. AAV6 donor templates for HDR were generated from a construct containing AAV2 inverted terminal repeats, produced by a triple-transfection method and purified by ultracentrifugation on a caesium chloride gradient as previously described (Wang, L. et al. (2015) Mol Ther 23: 1877-1887). Clinical-grade ARSA and IDUA LVs were produced by MolMed (Milan, Italy) using a large scale validated process as previously reported (Biffi, A. et al. (2013) Science 341: 1233158).

Cells

Cell Lines

The human embryonic kidney 293T cells (HEK293T) as well as the human K562 myelogenous leukaemia cell lines were maintained in Iscove's modified Dulbecco's medium (IMDM; Sigma). Human THP-1 cells were maintained in Roswell Park Memorial Institute medium (RPMI; Lonza). Both media were supplemented with 10% fetal bovine serum (FBS; Gibco), penicillin (100 IU/ml), streptomycin (100 µg/ml) and 2% glutamine.

Primary Cells

Human CD34+ HSPCs, CD4+ or CD3+ T cells and CD14+ monocytes were isolated through positive magnetic bead selection according to manufacturer's instructions (Miltenyi) from umbilical cord blood (CB) or from mononuclear cells collected upon informed consent from healthy volunteers according to the Institutional Ethical Committee approved protocol (TIGET01). Otherwise, CB, bone marrow (BM) or G-CSF mobilised peripheral blood (mPB) CD34+ cells were directly purchased from Lonza or Hemacare. CD4+ T cells were activated in RPMI, supplemented with 10% FBS, penicillin (100 IU/ml), streptomycin (100 µg/ml), 2% glutamine, phytohaemagglutanin (PHA) (2 µg/ml, Roche) and IL-2 (300 IU/ml, Novartis) for three days and maintained in RPMI, supplemented with 10% FBS, penicillin (100 IU/ml), streptomycin (100 µg/ml), 2% glutamine and IL-2 (300 UI/ml). Otherwise CD3+ T cells were stimulated using magnetic beads conjugated to anti-human CD3 and CD28 antibodies (Dynabeads human T-activator CD3/CD28; Invitrogen), following the manufacturers' instructions, and grown in Iscove's Modified Dulbecco's Media (IMDM) (GIBCO-BRL) supplemented with penicillin, streptomycin, 10% FBS and 5 ng/ml each of IL-7 and IL-15 (PeproTech). Monocyte-derived macrophages (MDM) were differentiated from isolated CD14+ monocytes in DMEM supplemented with 10% FBS, penicillin (100 IU/ml), streptomycin (100 µg/ml), 2% glutamine and 5% human serum AB (Lonza) for seven days.

All cells were maintained in a 5% $CO_2$ humidified atmosphere at 37° C.

Transduction

Human CB-derived haematopoietic stem/progenitor cells (HSPCs) were cultured in serum-free StemSpan medium (StemCell Technologies) supplemented with penicillin (100 IU/ml), streptomycin (100 µg/ml), 100 ng/ml recombinant human stem cell factor (rhSCF), 20 ng/ml recombinant human thrombopoietin (rhTPO), 100 ng/ml recombinant human Flt3 ligand (rhFlt3), and 20 ng/ml recombinant human IL6 (rhIL6) (all from Peprotech) 16 to 24 hours prior to transduction. HSPCs were then transduced at a concentration of 1×10⁶ cells per millilitre with vesicular stomatitis virus glycoprotein (VSV-G)-pseudotyped SINLV for 16 hours at the indicated multiplicity of infection (MOI) in the same medium. Bone marrow and G-CSF mobilised peripheral blood CD34+ cells were placed in culture on retronectin-coated non tissue culture-treated wells (T100A Takara) in CellGro medium (Cell Genix) containing a cocktail of cytokines: 60 ng/ml IL-3, 100 ng/ml TPO, 300 ng/ml SCF, and 300 ng/ml FLT-3L (all from Cell Peprotech). Cells were then transduced with the indicated dose of vectors for 14-15 hours in the same cytokine-containing medium. After transduction with a single hit reporter LV, cells were washed and maintained in serum-free medium supplemented with cytokines as above until reading the percentage of positive cells by FACS, after which they were maintained in IMDM supplemented with 10% FBS, 25 ng/ml rhSCF, 5 ng/ml rhIL6-3, 25 ng/ml rhFlt3 and 5 ng/ml rhTPO for another seven days before vector copy number analysis. In the protocol that foresees two rounds of transduction, selected for clinical application, cells were washed for 10 hours in CellGro SCGM medium supplemented with cytokines and underwent a second hit of transduction in the same conditions as the first, as reported previously (Biffi, A. et al. (2013) Science 341: 1233158). At the end of transduction, cells were counted and collected for clonogenic assays, flow cytometry, and in vivo studies. Remaining cells were plated in IMDM 10% foetal bovine serum (FBS) with cytokines (IL-3, 60 ng/ml; IL-6, 60 ng/ml; SCF, 300 ng/ml) and cultured for a total of 14 days. Thereafter, cells were collected for molecular and biochemical studies. Unstimulated HSPCs were transduced freshly isolated in StemSpan medium supplemented with penicillin (100 IU/ml), streptomycin (100 μg/ml) for 16-24 hours and then maintained in presence of human cytokines and 10 μM of the reverse-transcriptase inhibitor 3TC (SIGMA) to avoid subsequent transduction due to cytokine stimulation.

MDM were transduced 7 days after differentiation. T lymphocytes were transduced at a concentration of 10⁶ cells/ml, after 2-3 days of stimulation. The cells were exposed to the vector for 16-20 hours.

Compounds

Cyclosporin A (CsA), cyclosporin H (CsH) and rapamycin (all from Sigma-Aldrich) were resuspended and stored according to the manufacturer's instructions. They were added to the transduction medium at the indicated concentration and washed out with the vector 16-20 hours later. Where described, Prostaglandin E2 (Dinoprostone from Yonsung) was added at a final concentration of 10 μM two hours before LV transduction.

Linear Amplification Mediated-PCR and Sequencing

Linear amplification mediated (LAM)-PCR was performed on ~300 ng of DNA extracted from cultured cells. Briefly, 100 cycles of linear PCR pre-amplification of vector-genome junctions were made, followed by magnetic capture of the biotinylated target DNA by streptavidin-coupled magnetic beads, hexanucleotide priming, restriction digestion using MluCI, HpyCHIV4 and AciI enzymes, and ligation to a restriction site-complementary linker cassette. The ligation product was then amplified by two nested PCR with primers specific for the vector long terminal repeat (LTR) and the Linker cassette sequences. LAM-PCR amplicons were separated on a Shimadzu MultiNA Microchip Electrophoresis System to evaluate PCR efficiency and the band pattern for each sample. Primers and PCR thermal protocols used have been described previously (Schmidt, M. et al. (2007) Nat Methods 4: 1051-1057). LAM-PCR products were then purified by AmpureXP beads and quantified with a Qubit™ Fluorometer (Thermo Fisher Scientific, Pittsburgh, PA). 40 ng of PCR product was reamplified with Fusion-LTR (AATGATACGGCGACCACCGAGATCTA-CACTCTTTCCCTACACGACGCTCTTCCGATCTNN NNNNNNNNNNXXXXXXXXACCCTTT-TAGTCAGTGTGGA) (SEQ ID NO: 1) and Fusion-LC (CAAGCAGAAGACGGCATACGAGATGTGACTG-GAGTTCAGACGTGTGCTCTTCCGATCTNN NNNNNNNNNXXXXXXXXgatctgaattcagtggcacag) (SEQ ID NO: 2) primers, containing eight nucleotide (X) tags allowing the samples to be barcoded on both the LTR and the Linker cassette side of the amplicons, specific sequences that allow paired end sequencing with the Illumina MiSeq System, and a random 12 nucleotide (N) sequence to increase cluster separation. PCR was performed using Qiagen TAQ DNA Polymerase under the following conditions: 95° C. for 2 min, and 95° C. for 45 s, 58° C. for 45 s, and 72° C. for 1 min, for 12 cycles, followed by a further 5 min incubation at 72° C. Barcoded LAM-PCR products were quantified by fluorometric quantification and assembled into libraries in equimolar ratios, and avoiding repetition of identical pairs.

Common Insertion Site Analysis

Significant common insertion sites (CIS) were identified by using a sliding-window approach (Abel, U. et al. (2007) PLoS One 2: e570) and the Grubbs test for outliers for insertion site (IS) analysis (Biffi, A. et al. (2011) Blood 117: 5332-5339). For the sliding-window method, the R package (latest update of August 2012) was exploited using the function "Cluster" that returned the original input list of IS with additional annotation fields such as "CIS max order" that represents the maximum number of integrations contained in each CIS and "Cluster ID" that represents a genomic window in which one or more CIS intervals are clustered. For the gene-centric method, the annotation of RefSeq genes was used (General Feature Format file downloaded from UCSC Genome Browser, release hg19, NCBI Build 37), and the average transcript length for each gene symbol was computed. Then, the Grubbs test was performed for outliers to compare the integration frequency for each targeted gene with respect to the average frequency for all the targeted genes of the data set. To compare the IS distributions retrieved from cells transduced in the presence of DMSO versus those transduced in the presence of CsA we extracted the coverage of IS over 5 Mb windows sliding 1 Mb over the entire genome. We then calculated the log 2-Fold Change for each window, comparing CsA with DMSO.

Gene Editing of Human and Mouse Cells

LV donor templates for HDR were generated using HIV-derived, third-generation self-inactivating transfer constructs. IDLV stocks were prepared and titered as previously described (Lombardo, A. et al. (2007) Nat Biotechnol 25: 1298-1306). For gene editing experiments in mouse HSPC, Gt(ROSA)26Sortm1.1(CAG-cas9*,-EGFP)Fezh/J mice were crossed to humanized SCID-X1 C57B6 mice, which have a knock-in of a mutated human IL2RG in place of the murine ll2rg gene (Schiroli, G. et al. (2017) Sci Transl Med 9: 411). HSPCs were purified from 8 weeks-old donor mice by Lin− selection using the mouse Lineage Cell Depletion Kit (Miltenyi Biotec) according to the manufacturer's instructions. Lin− cells were cultured at a concentration of 10⁶ cells/ml in serum-free StemSpan medium (StemCell Technologies) containing penicillin, streptomycin, glutamine, 200 ng/ml B18R Recombinant Protein (eBiovision) and a combination of mouse cytokines (20 ng/ml IL-3, 100 ng/ml SCF, 100 ng/ml Flt-3L, 50 ng/ml TPO all from Peprotech). Lin− cells were pre-stimulated for 2 hours and then transduced with IDLV comprising a donor template for correcting IL2RG (plus a reporter cassette to track edited cells) and expressing the cognate gRNA to edit IL2RG under the control of the constitutive PolIII promoter U6 (recognized genomic sequence: TTCCACAGAGTGGGT-TAAAGcgg) (SEQ ID NO: 3) (Schiroli, G. et al. (2017) Sci Transl Med 9: 411). After 24 hours of transduction at MOI 100 in presence or not of CsH, cells were washed with PBS and then cultured in vitro for additional 3 days to quantify the fraction of edited cells by flow cytometry. For gene editing experiments in human HSPC, $10^6$ CD34$^+$ cells/ml were stimulated in serum-free StemSpan medium (StemCell Technologies) supplemented with penicillin, streptomycin, glutamine, 1 µM SR-1 (Biovision), 50 µM UM171 (STEM-Cell Technologies), 10 µM PGE2 added only at the beginning of the culture (Cayman), and human early-acting cytokines (SCF 100 ng/ml, Flt3-L 100 ng/ml, TPO 20 ng/ml, and IL-6 20 ng/ml; all purchased from Peprotech) (Schiroli, G. et al. (2017) Sci Transl Med 9: 411). Transduction with IDLV was performed at MOI 100, in presence or not of CsH, after 2 days of prestimulation. IDLV donor templates with homologies for AA VS1 locus (encoding for a PGK.GFP reporter cassette; (Genovese, P. et al. (2014) Nature 510: 235-240) or targeting the intron 1 of/L2RG (encoding for IL2RG corrective cDNA; (Schiroli, G. et al. (2017) Sci Transl Med 9: 411) were utilized as indicated. After 24 hours from transduction, cells were washed with PBS and electroporated (P3 Primary Cell 4D-Nucleofector X Kit, program EO-100; Lonza) with 1.25 µM of ribonucleoproteins (RNP). RNPs were assembled by incubating at 1:1.5 molar ratio s.p.Cas9 protein (Integrated DNA Technologies) with synthetic cr:tracrRNA (Integrated DNA Technologies) for 10' at 25° C. Electroporation enhancer (Integrated DNA Technologies) was added prior to electroporation according to manufacturer's instructions. Genomic sequences recognized by the gRNAs are the following: TCAC-CAATCCTGTCCCTAGtgg (SEQ ID NO: 4) for AAVS1 locus and ACTGGCCATTACAATCATGTggg (SEQ ID NO: 5) for intron 1 IL2RG. Gene editing efficiency was measured from cultured cells in vitro 3 days after electroporation. For AAVS1 edited cells, editing by homology-directed repair (HDR) was quantified by flow cytometry measuring the percentage of cells expressing the GFP marker. For IL2RG edited cells, HDR was quantified by digital droplet PCR analysis designing primers and probe on the junction between the vector sequence and the targeted locus and on control sequences utilized as normalizer (human TTC5 genes) as previously described (Schiroli, G. et al. (2017) Sci Transl Med 9: 411).

Transplantation of Human HSPC in NSG Mice

NOD-SCID-IL2Rg−/− (NSG) mice were purchased from Jackson laboratory. All animal procedures were performed according to protocols approved by the Animal Care and Use Committee of the Ospedale San Raffaele (IACUC 784) and communicated to the Ministry of Health and local authorities according to Italian law. Human bone marrow-derived CD34+ cells were pre-stimulated and transduced as described before with IDUA-LV at an MOI of 100 in presence or not of DMSO, CsA and/or rapamycin as indicated. Human mPB CD34+ cells were pre-stimulated and transduced as described before with IDUA-LV at an MOI of 50 in presence or not of DMSO, CsH and/or 16-16 dimethyl prostaglandin E2 or their combination as indicated. After transduction 2-5×$10^5$ cells were infused into the tail vein of sublethally irradiated 8-10 week-old NSG mice (radiation dose: 200 cGy for mice weighing 18-25 g and of 220 cGy for mice above 25 g in weight). Transduced and untransduced cells were also cultured in vitro for 14 days for further analysis. In vitro cultured cells and BM cells isolated from transplanted mice at time of sacrifice were then used to quantify the VCN by qPCR.

Colony-Forming Cell Assay

Colony-forming cell assays were performed by plating 8×$10^2$ human HSPCs transduced in the presence of the different compounds in a methylcellulose-based medium (Methocult GF4434; Stem Cell Technologies). Fifteen days later colonies were scored by light microscopy for colony numbers and morphology. CFU-E and BFU-E were scored as erythroid colonies, while CFU-G, CFU-M and CFU-GM and CFU-GEMM were scored as myeloid colonies. Moreover, single colonies were plucked for molecular analysis.

Flow Cytometry

All cytometric analyses were performed using the FACSCanto III instrument and LSRFortessa instruments (BD Biosciences) and analysed with the FACS Express software (De Novo Software).

Transduced Cells

GFP or BFP expression in transduced cells was measured 5-7 days post-transduction. Adherent MDM were detached by scraping in 5 mM PBS-EDTA, washed and resuspended in PBS containing 2% fetal bovine serum (FBS). Cells grown in suspension were washed and resuspended in PBS containing 2% FBS. To measure HSPC subpopulation composition cells were harvested 16 or 72 hours post-transduction, incubated with anti-human receptor blocking antibodies for 15 min at 4° C. and then stained for 20 min at 4° C. with anti-human CD34, CD38, CD45RA, CD90 or with anti-human CD34, CD133, CD90 antibodies (for antibodies, see Table 3). To exclude dead cells from the analysis, 10 ng/ml 7-aminoactinomycin D (7-AAD) was added.

Human Colonies

Human differentiated cells from CFC were harvested from a single plate (pool of colonies) and mixed into a single cell suspension. Cells were then washed and resuspended in PBS containing 2% FBS. For immunostaining, cells were incubated with anti-human receptor blocking antibodies for 15 min at 4° C. and then stained for 20 min at 4° C. with anti-human CD235a and CD33 antibodies (for antibodies, see Table 3). To exclude dead cells from the analysis, cells were washed and resuspended in PBS containing 10 ng/ml 7-aminoactinomycin D (7-AAD).

Peripheral Blood from Mice

For each mouse, 250 µl of peripheral blood were added to 15 µL of PBS containing 45 mg/mL EDTA. For immunostaining a known volume of whole blood (100 µl) was first incubated with anti-human FcγIII/II receptor (Cd16/Cd32) blocking antibodies for 15 min at 4° C. and then incubated in the presence of monoclonal antibodies (for antibodies, see Table 3) for 20 min at 4° C. Erythrocytes were removed by lysis with the TQ-Prep workstation (Beckman-Coulter) in the presence of an equal volume of FBS (100 µl) to protect white blood cells.

Bone Marrow

BM cells were obtained by flushing the femurs in PBS 2% FBS solution. Cells (1×$10^6$ cells) were washed, resuspended in 100 µl of PBS containing 2% FBS, and incubated with anti-human receptor (Cd16/Cd32) blocking antibodies for 15 min at 4° C. Staining was then performed with monoclonal antibodies (for antibodies, see Table 3) for 20 min at 4° C. Cells were washed and finally resuspended in PBS containing 2% FBS.

Spleen

Spleens were first smashed and the resulting cell suspension was passed through a 40 μm nylon filter and washed in cold phosphate buffered saline (PBS) containing 2 mM EDTA and 0.5% bovine serum albumin (BSA). Cells were incubated with anti-human receptor (Cd16/Cd32) blocking antibodies for 15 min at 4° C. and then stained with anti-human monoclonal antibodies (for antibodies, see Table 3) for 20 min at 4° C. Cells were finally washed and resuspended in PBS containing 2% FBS.

Ki67 and Hoechst Flow Cytometry

Cells were washed and fixed using BD Cytofix buffer (Cat. #554655), washed and permeabilised with BD Perm 2 (Cat. #347692), washed and stained with PE-conjugated Ki67 antibody (BD) and finally resuspended in BD Cytofix buffer with Hoechst at 1 μg/mL. The cells were then analysed on a BD LSRII machine with a UV laser.

Cell Proliferation Assay

Cells were stained with Cell Proliferation Dye eFluor® 670 (Affimetrix, eBioscience) after 24 hours of cytokine pre-stimulation and before cell transduction. This fluorescent dye binds to any cellular protein containing primary amines, and as cells divide, the dye is distributed equally between daughter cells that can be measured as successive halving of the fluorescence intensity of the dye. At different time points after transduction, cells were harvested and analysed by flow cytometry. Cell Proliferation Dye eFluor®670 has a peak excitation of 647 nm and can be excited by the red (633 nm) laser line. It has a peak emission of 670 nm and can be detected with a 660/20 band pass filter (equivalent to APC, Alexa Fluor® 647 or eFluor® 660).

ROS Quantification

Cells were stained with CM-H2DCFDA (Thermo Fisher Scientific) which passively diffuses into cells where its acetate groups are cleaved by intracellular esterases and its thiol-reactive chloromethyl group reacts with intracellular glutathione and other thiols. Subsequent oxidation yields a fluorescent adduct that is trapped inside the cell and monitored using a flow cytometer. N-acetyl-L-cysteine (NAC, from SIGMA) and hydrogen peroxide ($H_2O_2$, SIGMA) were added with the fluorescent probe at a concentration 1 mM and 10 mM, respectively.

RNA Extraction, qPCR and Gene Expression Analysis

RNA extraction from cells was performed using the RNeasy Plus mini Kit (Qiagen). Briefly, cells were lysed in Buffer RLT plus, supplemented with beta-mercaptoethanol. RNA was then extracted according to the manufacturer's instructions. The extracted mRNAs were retrotranscribed using the SuperScript Vilo kit (11754250; Invitrogen). Q-PCR analyses were done using TaqMan probes from Applied Biosystems (see below). Q-PCR was run for 40 cycles using the Viia 7 instrument while the Viia 7 software was then used to extract the raw data (Ct). To determine gene expression, the difference (ΔCt) between the threshold cycle (Ct) of each gene and that of the reference gene was calculated by applying an equal threshold. Relative quantification values were calculated as the fold-change expression of the gene of interest over its expression in the reference sample, by the formula 2-ΔΔCt. The expression was normalised using the housekeeping gene HPRT1. The following Taqman probes from Applied Biosystems were used: PPIA (Hs99999904_m1), PPIB (Hs00168719_m1), OAS1 (Hs00973637_m1), IRF7 (Hs01014809_g1), MX2 (Hs01550808_m1) and HPRT1 (Hs01003267_m1).

Replication Intermediates

CB-derived CD34+ cells were transduced at an MOI of 100, in presence or absence of CsA or CsH. To analyse viral replication intermediates, transduced cells were washed and resuspended in Monini lysis buffer (0.1% polyoxyethylene 10 lauryl ether (Sigma), 0.1 mg/mL proteinase K (Promega)) (25 μl/1×10⁵ cells), incubated at 65° C. for 2 h and heat inactivated at 94° C. for 15 min (Monini, P. et al. (1999) Blood 93: 4044-4058). Lysis of the cells to retrieve Late-RT and 2-LTR intermediates was performed at 6 or 24 hours post-transduction, respectively. Late-RT and 2LTR circles were measured by quantitative droplet digital-PCR (dd-PCR) assay with primers described below and normalised using the human TERT gene.

The primers to detect late-RT products are:

LATE RT fw (DU3 sense): 5'-TCACTCCCAACGAAGACAAGAT

C-3' (SEQ ID NO: 6)c(Matrai, J. et al.

(2011) Hepatology 53: 1696-1707)

LATE RT rv (5NC2 rev): 5'-GAGTCCTGCGTCGAGAGAG-3'

(SEQ ID NO: 7) (Naldini, L. et al. (1996)

Science 272: 263-267)

The primers to detect 2LTR products are:

2LTR fw (2junct): 5'-CAGTGTGGAAAATCTCTA

GCAGTAC-3' (SEQ ID NO: 8)

2LTR rv (J2 rev): 5'-GCCGTGCGCGCTTCA

GCAAGC-3' (SEQ ID NO: 9)

The primers to detect TELO are:

hTelo fw: 5'-GGCACACGTGGCTTTTCG-3'

(SEQ ID NO: 10) (Follenzi, A. et al. (2002)

Methods Enzymol 346: 454-465)

hTelo rev: 5'-GGTGAACCTCGTAAGTTTATGCAA-3'

(SEQ ID NO: 11)

Genomic DNA Extraction and qPCR

DNA from cell cultures and blood was extracted using a Maxwell 16 instrument (Promega) or Blood & Cell Culture DNA micro kit (Qiagen). Vector copies per diploid genome (vector copy number, VCN) of the integrated lentiviral vectors were quantified by quantitative droplet digital-PCR (dd-PCR) using the following primers (HIV sense: 5'-TACTGACGCTCTCGCACC-3' (SEQ ID NO: 12); HIV antisense: 5'-TCTCGACGCAGGACTCG-3' (SEQ ID NO: 13)) and probe (FAM 5'-ATCTCTCTCCTTCTAGCCTC-3') (SEQ ID NO: 14) against the primer binding site region of LVs. VCN quantification of the total lentiviral DNA (integrated and non-integrated) was performed as previously described (Matrai, J. et al. (2011) Hepatology 53: 1696-1707) at three days post-transduction. Copy numbers of the reverse transcribed retroviral vector genome (both integrated and non-integrated) was performed by quantitative droplet digital-PCR (dd-PCR) discriminating it from plasmid carried over from the transient transfection using the following primers: RT-RV; AU3 sense: 5'-CGAGCT-CAATAAAAGAGCCCAC-3' (SEQ ID NO: 15), PBS antisense: 5'-GAGTCCTGCGTCGGAGAGAG-3' (SEQ ID NO: 16). Vector copy numbers and replication intermediates were normalised to genomic DNA content, which was assessed using the human TERT gene. VCN analysis by dd-PCR involved quantification of target and reference loci through the use of duplex target and reference assays. In the QuantaSoft™ software, copy number was determined by calculating the ratio of the target molecule concentration to the reference molecule concentration, times the number of copies of reference species in the genome (usually 2).

TABLE 1

PCR reactions for dd-PCR.

| Cycling step | Temperature (° C.) | Time | Number of cycles | |
|---|---|---|---|---|
| Enzyme Activation | 95 | 5 min | 1 | dd-PCR |
| Denaturation | 95 | 30 sec | 40 | 200 or |

TABLE 1-continued

PCR reactions for dd-PCR.

| Cycling step | Temperature (° C.) | Time | Number of cycles | |
|---|---|---|---|---|
| Annealing/Extension | 63 | 1 min | 40 | 300 nM |
| Signal Stabilisation | 4 | 5 min | 1 | |
| | 90 | 5 min | 1 | |
| Hold (Optional) | 4 | Infinite | 1 | |

Western Blot

Whole cell extracts were prepared from HSPCs as previously described (Kajaste-Rudnitski, A. et al. (2011) J Virol 85: 5183-5196; Kajaste-Rudnitski, A. et al. (2006) J Biol Chem 281: 4624-4637). Samples were subjected to SDS-PAGE, transferred to PVDF membrane by electroblotting, and blotted with a mouse polyclonal antibody (Ab) raised against CypA (Santa-Cruz Biotechnology). An anti-actin Ab (Sigma-Aldrich) was used as a normaliser.

Statistical Analysis

In all studies, values are expressed as mean±standard error of the mean (SEM). Statistical analyses were performed by unpaired Student's t test or ANOVA for multiple comparisons, as indicated. Percentages were converted into Log ODDs for statistical analysis. Differences were considered statistically significant at $p<0.05$.

TABLE 2

Phenotypes reported for the CA mutants tested in this study.

| CA Mutants | Phenotypes | References |
|---|---|---|
| P90A | CypA and Nup153-independent | (Matreyek, K. A. et al. (2011) J Virol 85: 7818-7827; Rasaiyaah, J. et al. (2013) Nature 503: 402-405) |
| N74D | TNPO3 and Nup153-independent, affects CypA interaction | (Lee, K. et al. (2010) Cell Host Microbe 7: 221-233; Matreyek, K. A. et al. (2011) J Virol 85: 7818-7827; Zhou, L. et al. (2011) PLoS Pathog 7: e1002194) |

TABLE 3

List of anti-human antibodies used for flow cytometry.

| Antibody | Fluorochrome | Dilution | Clone | Company | Code |
|---|---|---|---|---|---|
| hCD235a | APC | 1:25 | GA-R2 | BD Biosciences | 551336 |
| hCD33 | BV421 | 1:25 | WM53 | BD Biosciences | 562854 |
| Anti human FCR Blocking | | 1:50 | | Miltenyi Biotec | 120-000-442 |
| hCD45 | APCh7 | 1:25 | 2D1 | BD Biosciences | 641417 |
| hCD19 | PE | 1:25 | SJ25C1 | BD Biosciences | 345789 |
| hCD33 | PeCy7 | 1:25 | P67.6 | BD Biosciences | 333952 |
| hCD3 | APC | 1:25 | UCHT1 | BD Biosciences | 555335 |
| hCD13 | BV | 1:25 | WM15 | BD Biosciences | 562596 |
| hCD34 | PeCy7 | 1:25 | 8G12 | BD Biosciences | 348811 |
| hCD38 | V450 | 1:25 | HB7 | BD Biosciences | 646851 |
| hCD90 | APC | 1:25 | 5E10 | BD Biosciences | 559869 |
| hCD133/2 | PE | 1:25 | 293C3 | Miltenyi Biotec | 130-090-853 |
| hCD45RA | PE | 1:25 | | Miltenyi Biotec | 130-092-248 |
| hKi67 | PE | 1:10 | B56 | BD | 51-36525X |
| IgG1 isotype control | PE | 1:10 | MOPC-21 | BD | 51-35405X |

Results

The Shortened CsA and Rapamycin-Based Protocols Safely Achieve Similar Gene Transfer Efficiency as the Current Clinical Standard and Improve HSPC Engraftment Human BM-derived CD34+ cells were transduced with a single hit of clinical-grade IDUA-expressing or ARSA-expressing LV with or without the compounds. As a control, cells were transduced with the current standard clinical transduction protocol, which consists of two hits of transduction (TD) at an MOI of 100 of vector (FIG. 1A). CsA and rapamycin were able to increase transduction efficiency of both clinical-grade IDUA and ARSA-LV as compared to the one-hit control without drugs, reaching VCN comparable to the two-hit gold standard in vitro (FIG. 1B-C). Moreover, no alterations in colony-forming capacity were observed (FIG. 1D).

Figure 2:
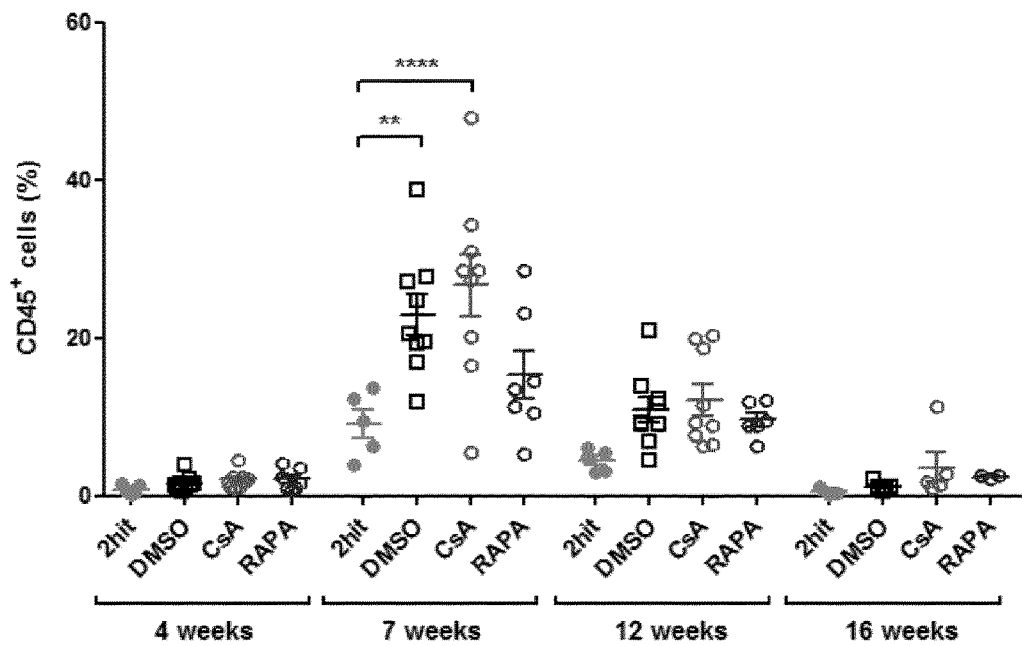
Figure 2:
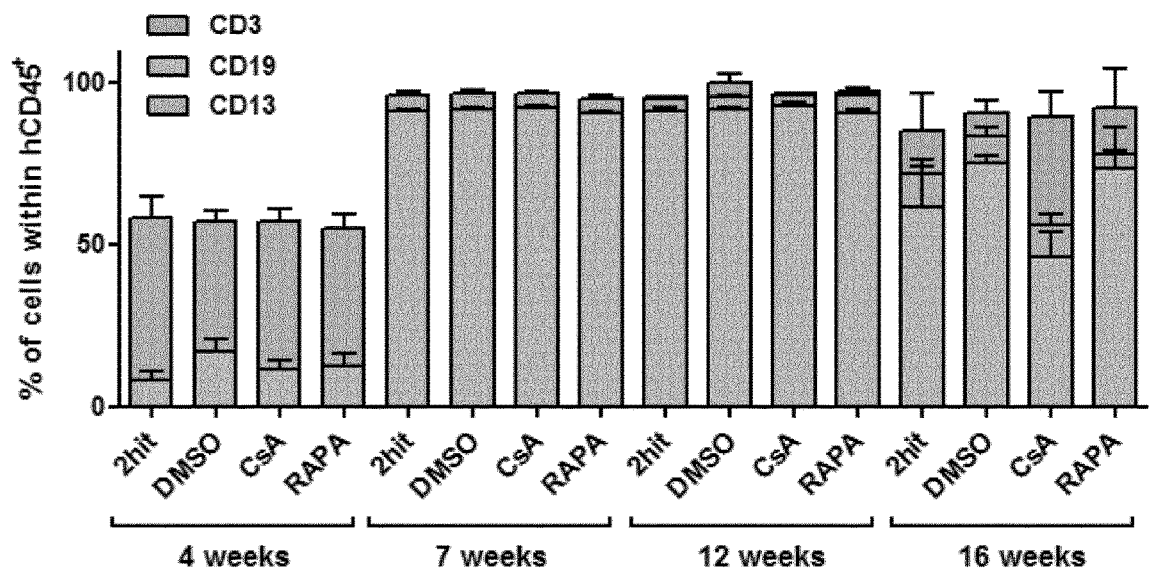
Figure 2:
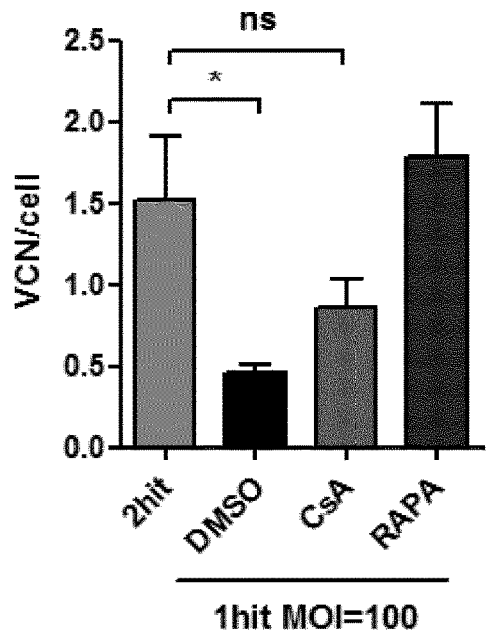
Figure 2:
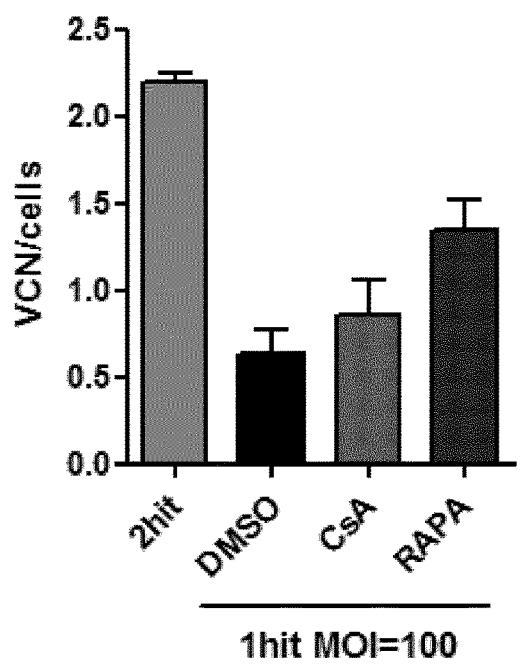
Figure 2:
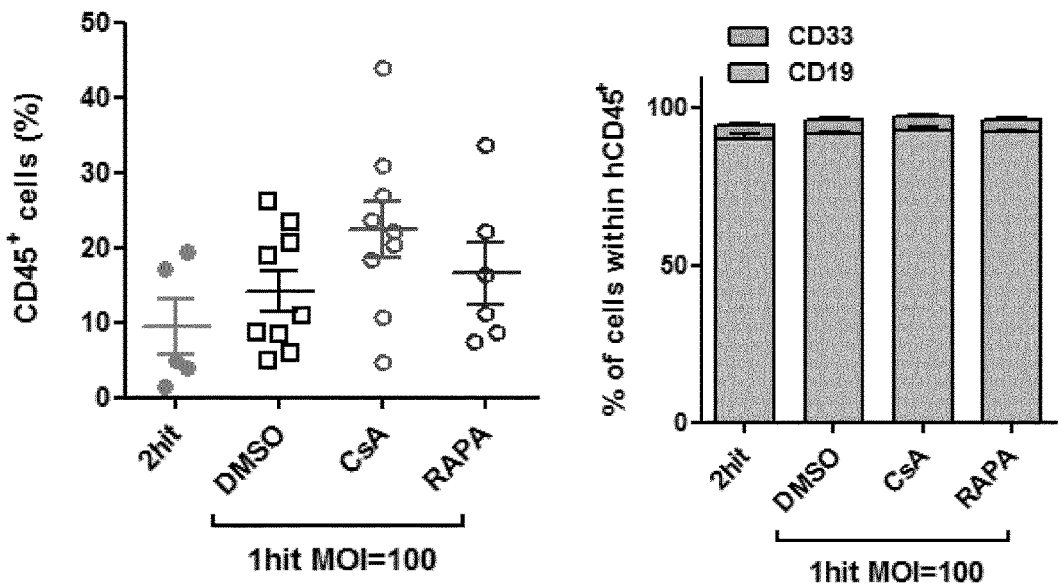
Figure 2:
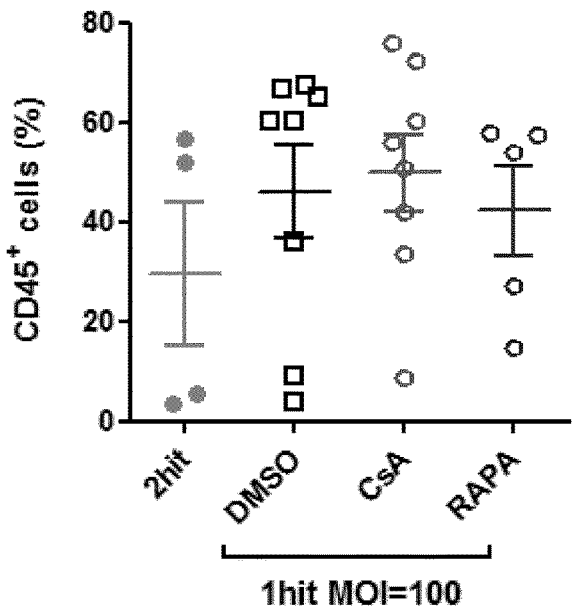

FACS analysis of the peripheral blood (PB) of NSG mice transplanted with single-hit transduced HSPCs showed better engraftment of human CD45+ cells compared to the clinical protocol, particularly with CsA, up to 16 weeks post-transplant (FIG. 2A). Moreover, no alterations in the different lineage outputs were observed (FIG. 2B). Both protocols enabled improved transduction of long-term repopulating HSPCs in vivo as VCN/human genome comparable to the two-hit gold standard were achieved in the BM and in the spleen of the mice 22 weeks post-transplantation (FIG. 2C). The shorter ex-vivo culture period per se improved HSPC engraftment also in the BM and in the spleen of the mice for all shorter protocols (FIG. 2D).

Figure 9:
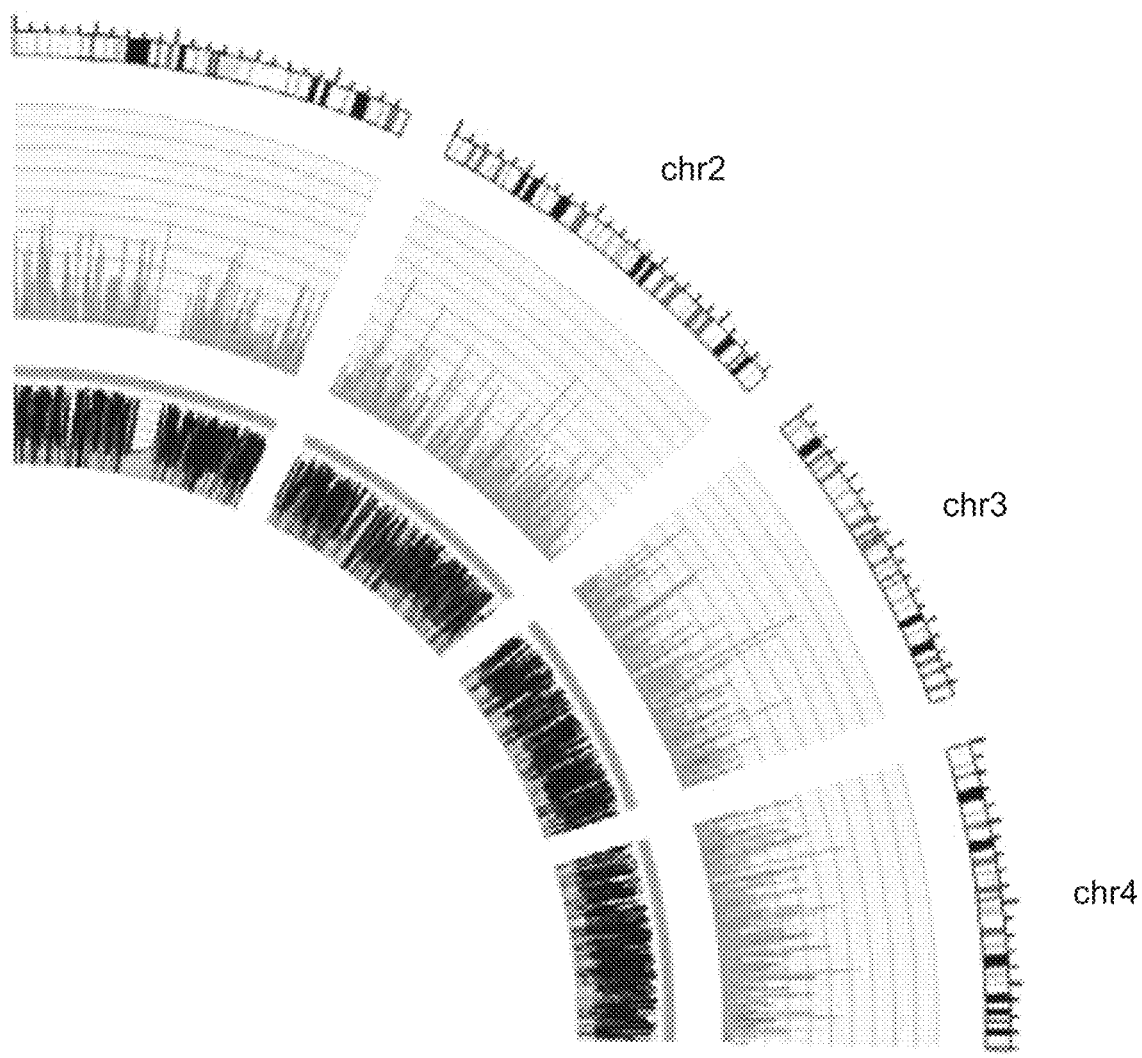
Figure 9:
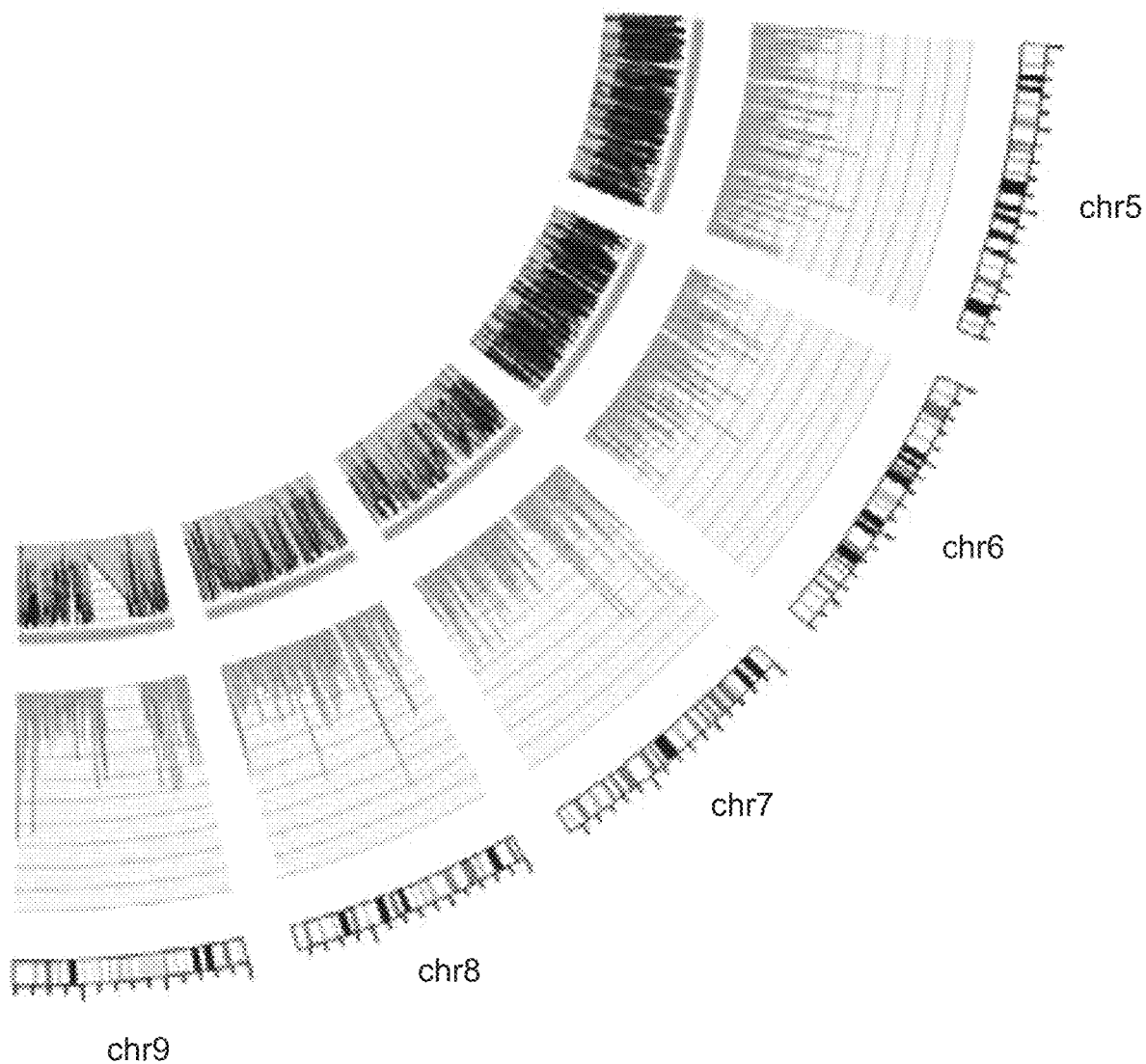
Figure 9:
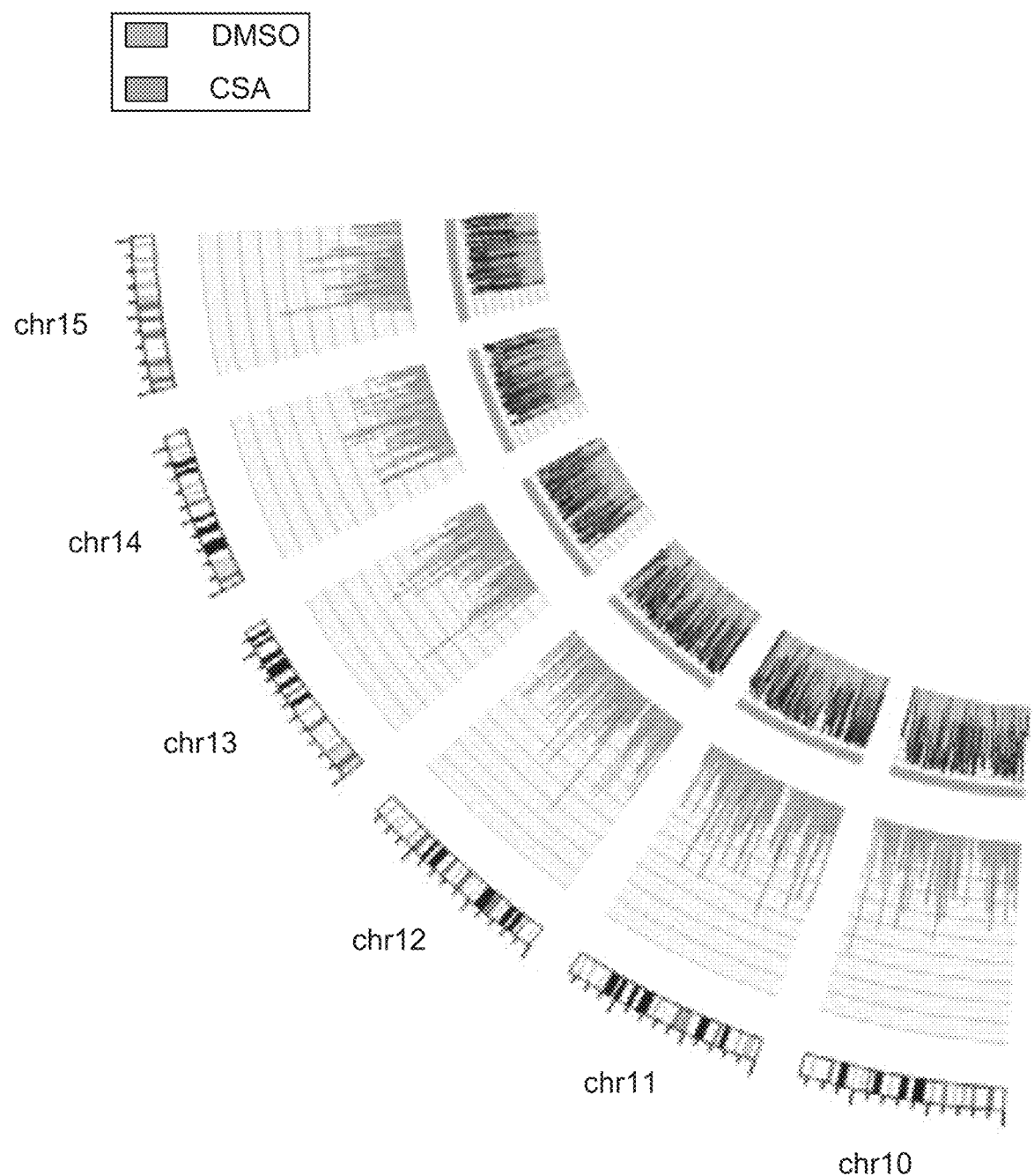
Figure 9:
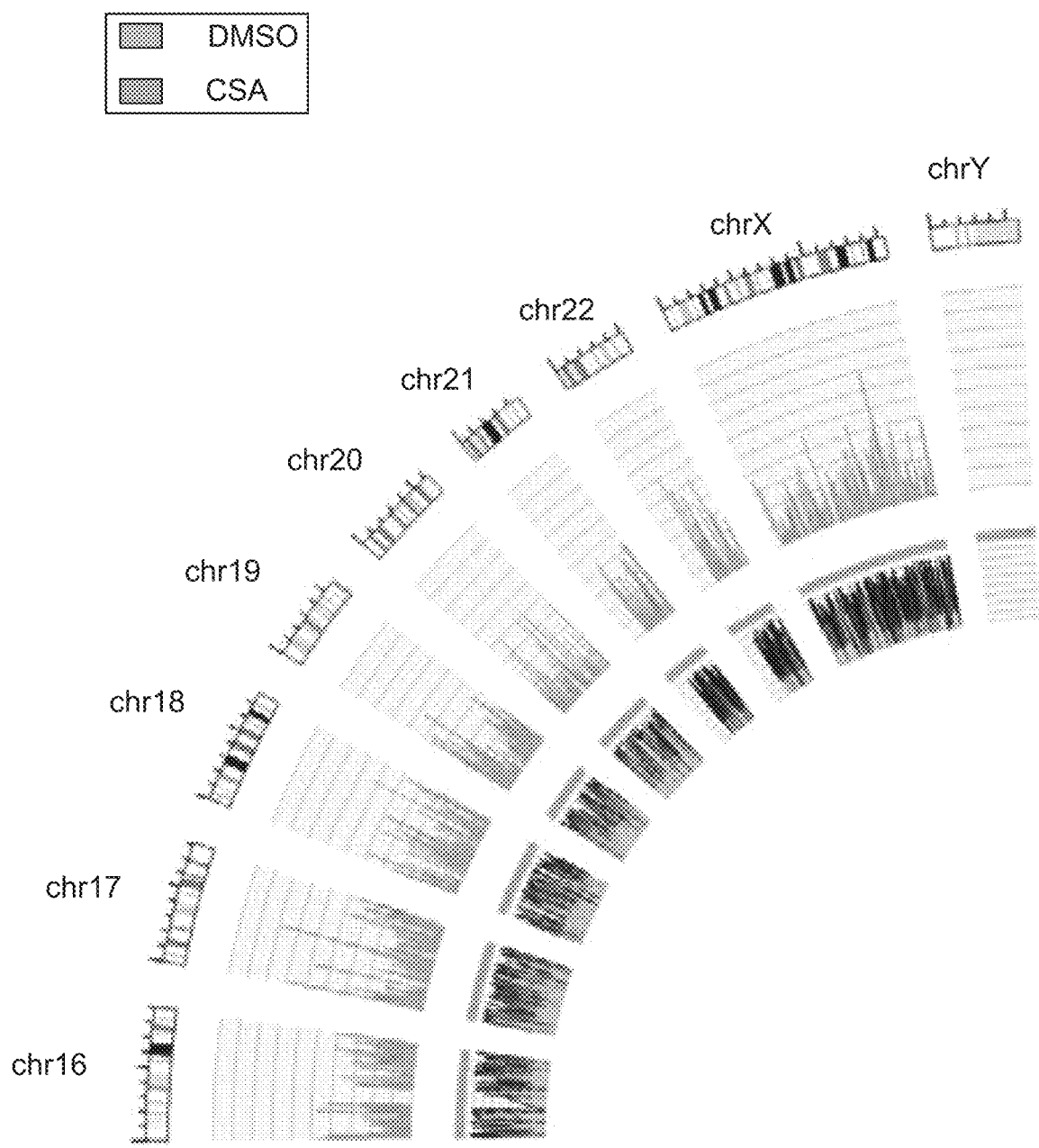

Rapamycin has been previously shown not to impact the LV integration site profile in human HSPCs (Wang, C X. et al. (2014). Rapamycin relieves lentiviral vector transduction resistance in human and mouse hematopoietic stem cells. Blood). We evaluated here the safety profile of the CsA-based gene transfer protocol in terms of LV integration site profiling. Although more integration sites were systematically retrieved in the presence of CsA, in agreement with its ability to increase vector copies per cell, we did not detect any significant differences between the distribution of the integration sites retrieved from HSPCs transduced in absence of presence of CsA and in comparison to the numerous IS studies obtained from recent gene therapy trials (Aiuti, A. et al. (2013) Science 341: 1233151; Biffi, A. et al. (2013) Science 341: 1233158) (FIG. 9).

CsA Preserves Primitive HSCs Ex Vivo Independently of Transduction

Figure 3:
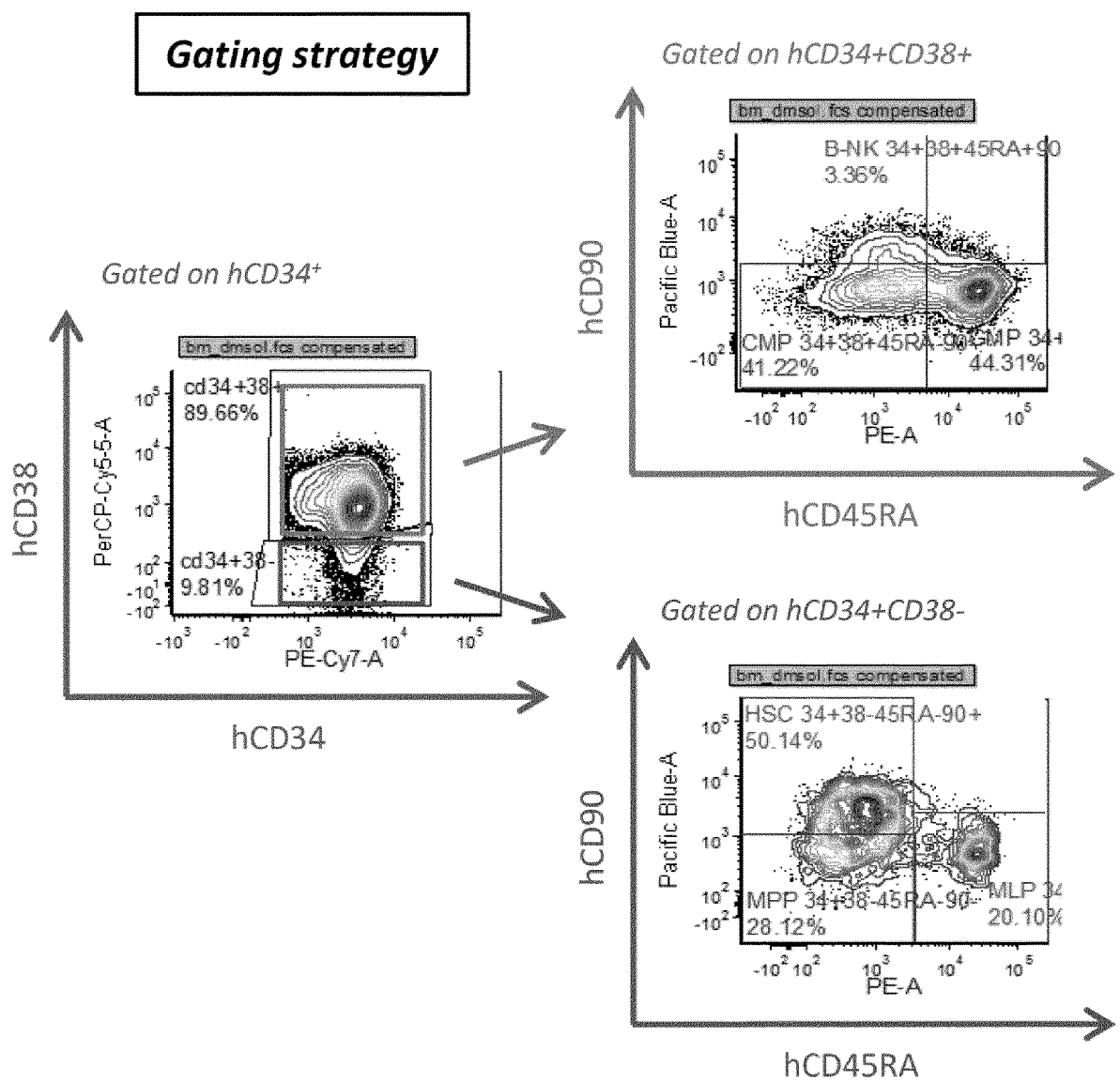
Figure 3:
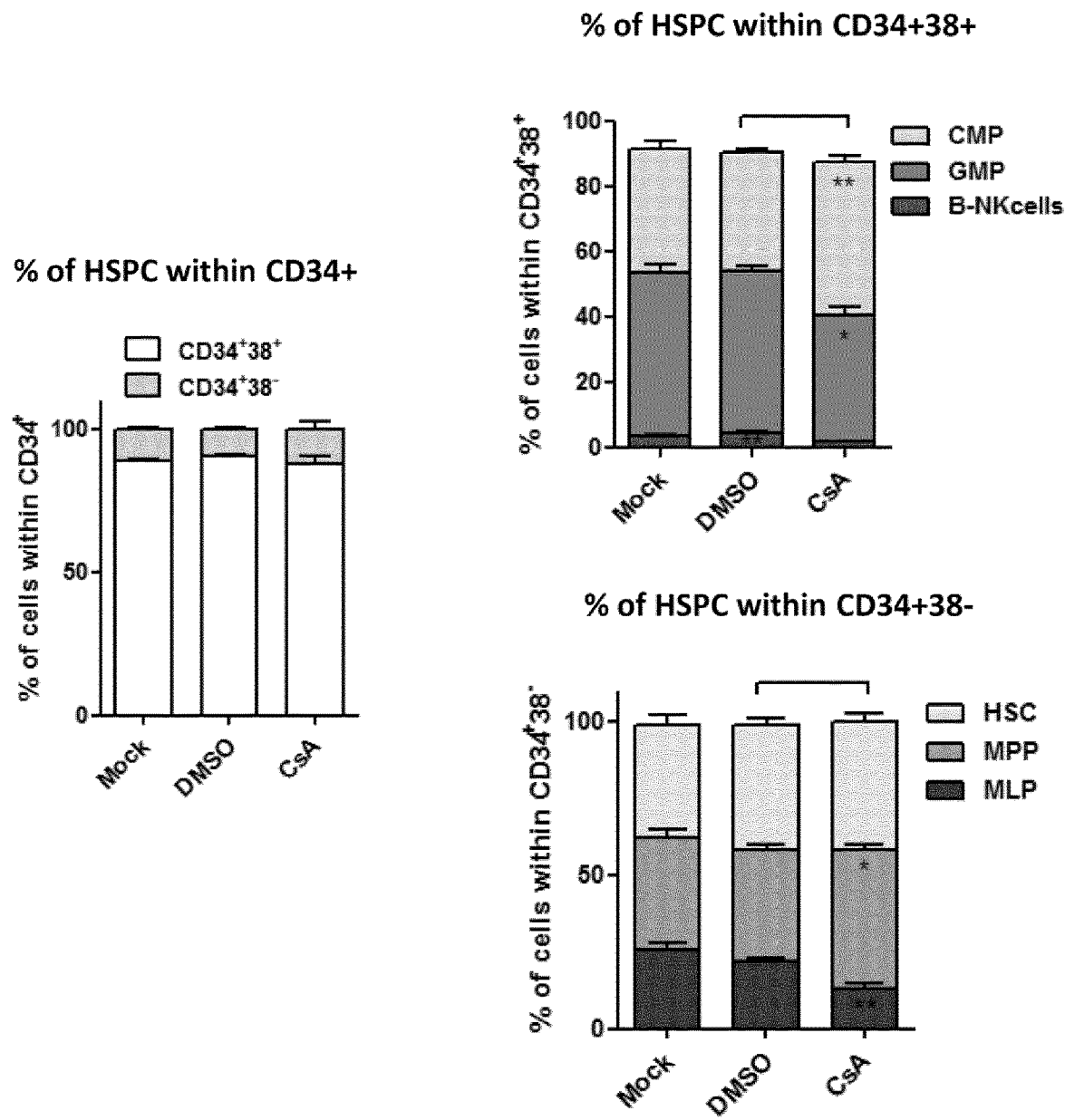
Figure 3:
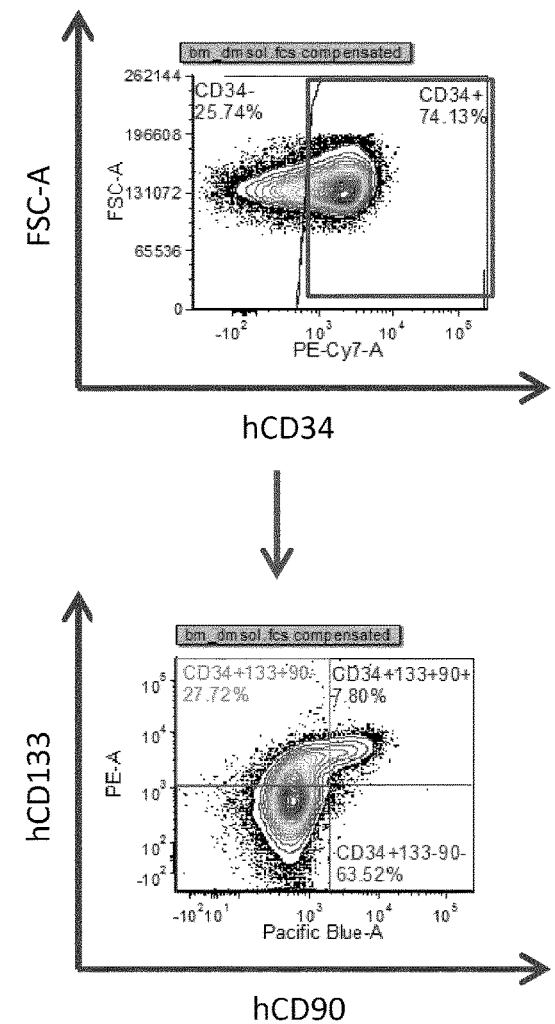
Figure 3:
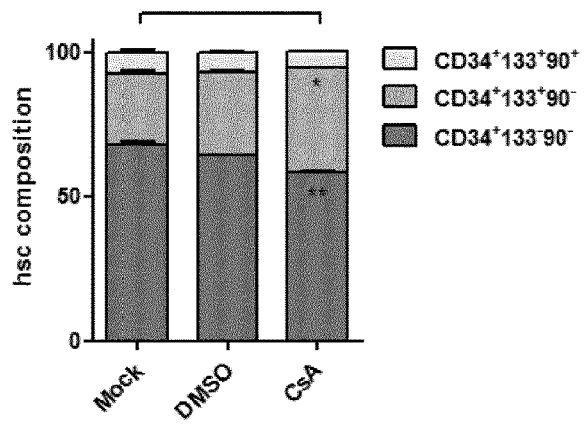
Figure 3:
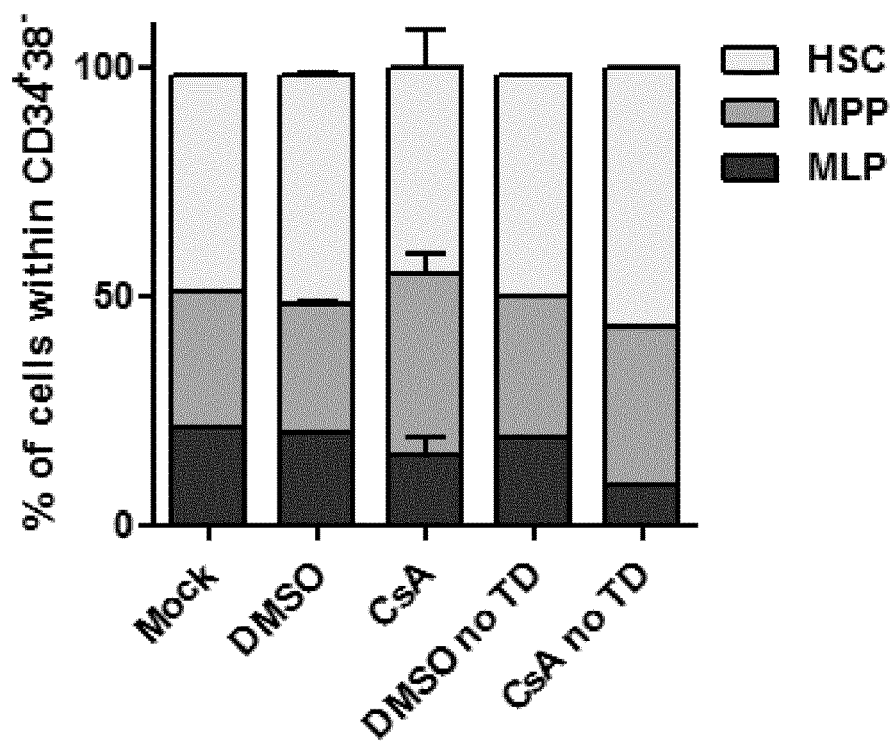

To investigate the reasons behind higher engraftment of human cells observed for the CsA condition, we evaluated the impact of CsA on the stem cell composition in vitro. Human BM-derived CD34+ cells were transduced with SINLV-GFP at an MOI of 10, in the presence or absence of CsA. The percentage of the primitive stem and progenitor cells was evaluated by FACS 16 hours post-TD (FIG. 3A). CsA exposure in vitro increases the percentage of the more primitive stem and multipotent progenitors while decreasing the more committed ones. Of note, no alterations in myeloid differentiation in culture over time were observed. The percentage of the primitive stem and progenitor cells was evaluated by FACS 72 hours post-TD (FIG. 3B). CsA exposure in vitro still increased the percentage of the more primitive stem and multipotent progenitors 3 days after TD.

Figure 4:
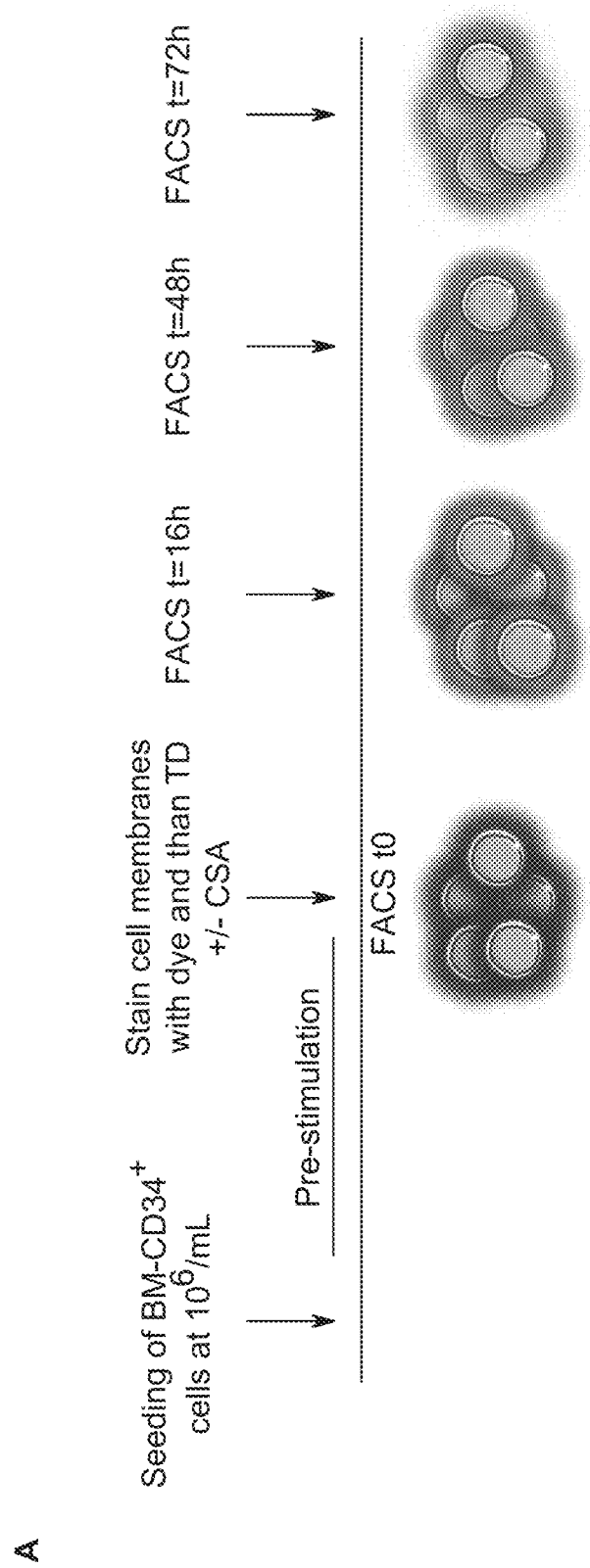
Figure 4:
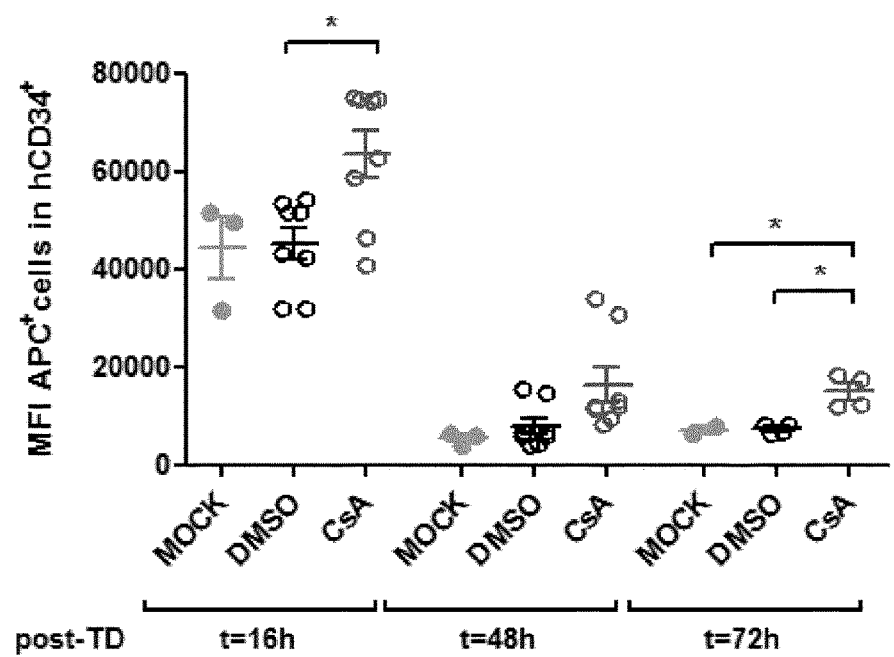
Figure 4:
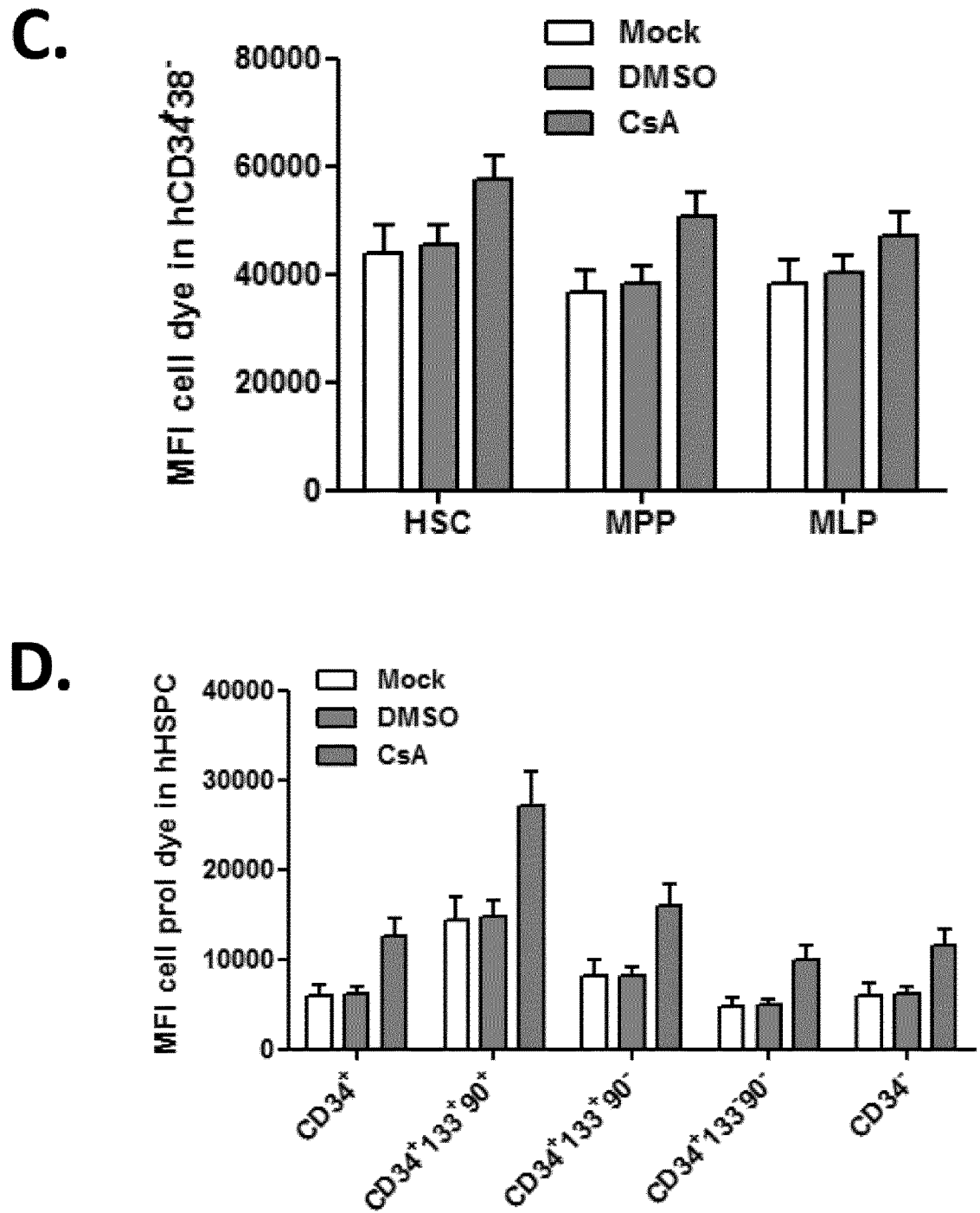
Figure 4:
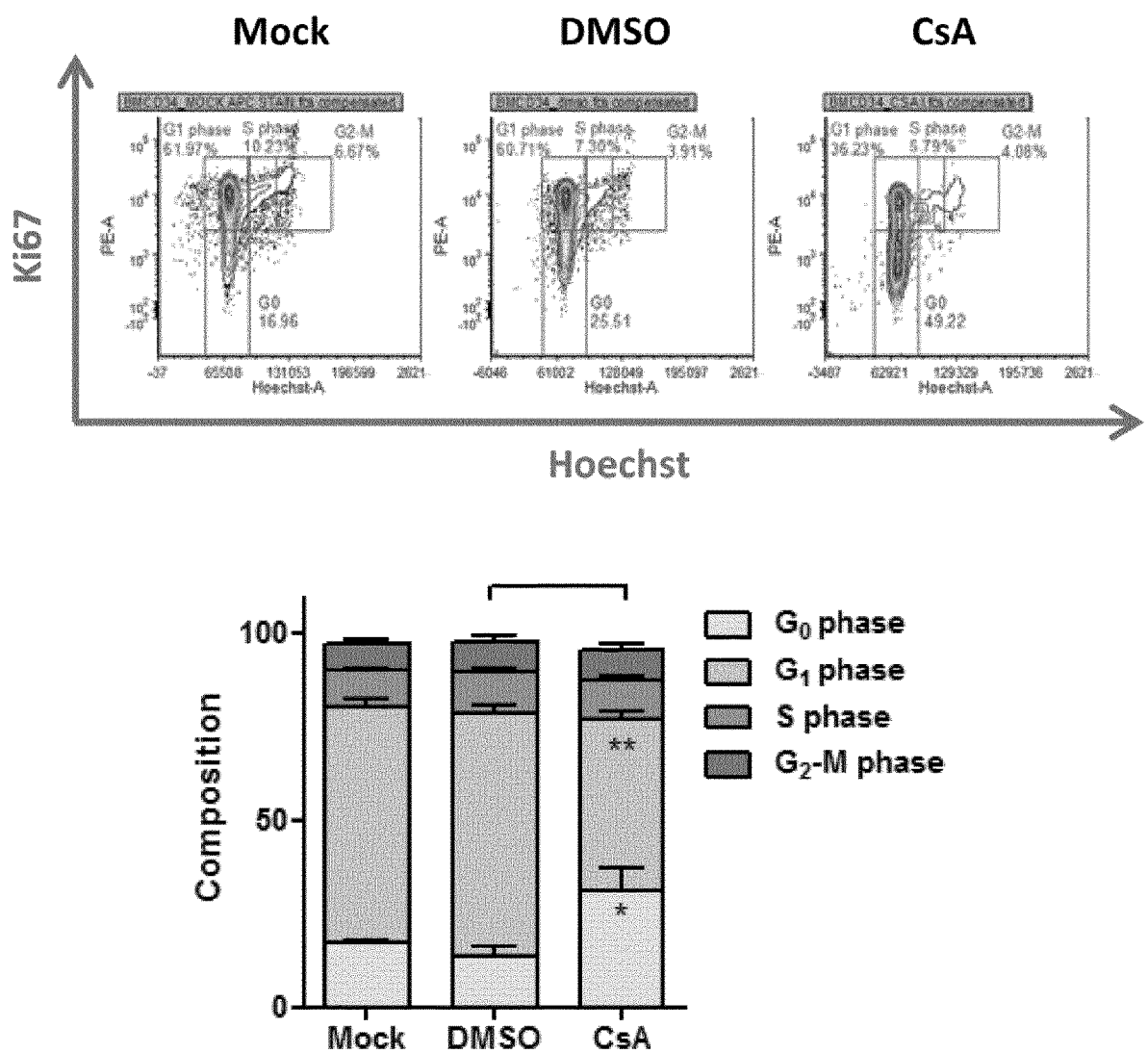
Figure 4:
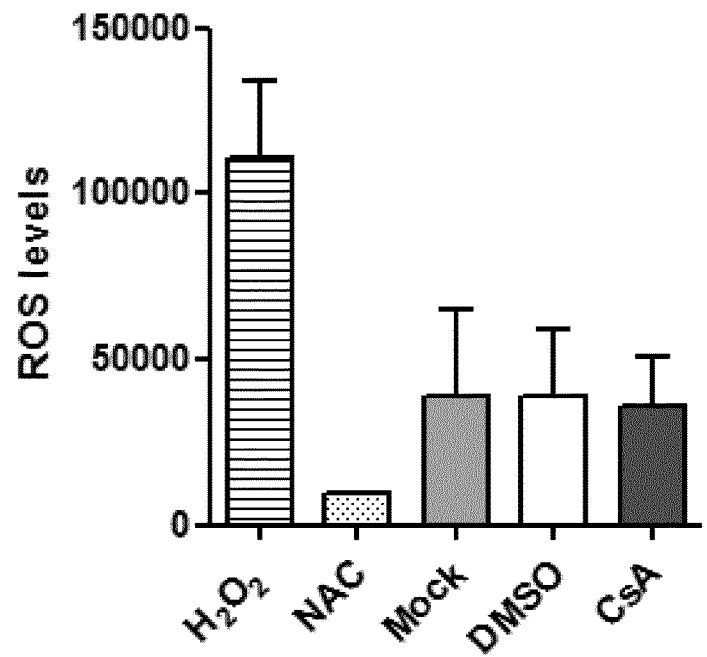

To investigate whether slower proliferation rates could explain the preservation of the more primitive cells in the presence of CsA, human BM-derived CD34+ cells were stained with a red fluorescent dye that can be used to monitor individual cell divisions. Following this staining, cells were transduced with or without CsA and analysed by FACS at different times post-TD to monitor cell proliferation rates (FIG. 4A). CsA significantly reduces cell proliferation in vitro (FIG. 4B). Levels of cell proliferation dye within the different HSPC subpopulations were evaluated by FACS 16 and 72 hours after transduction (FIG. 4C-D). CsA yielded equal reduction of cell proliferation in all HSPC subpopulations ranging from the more committed progenitors to the most primitive cells.

The primitive HSCs are characterised by a more quiescent cell cycle status. We investigated whether the CsA-mediated increase in HSCs is associated with a higher fraction of cells in the $G_0$ phase of the cell cycle. We used a FACS-based combinatorial staining strategy that allows us to distinguish cells in $G_0$, $G_1$, S and $G_2$-M phases of the cell cycle. CsA treatment significantly increased the proportion of cells arrested in the quiescent $G_0$ phase of the cycle (FIG. 4D). As oxidative stress plays a critical role in HSPC biology and CsA has been suggested to impact the redox balance in HSPCs (Mantel, C. R. et al. (2015) Cell 161: 1553-1565), we evaluated also the effects of CsA on ROS levels in human BM-derived HSPCs. In our experimental setting CsA did not lead to any alterations in the ROS levels measured in vitro (FIG. 4E). Taken together, the CsA-mediated decrease in HSPC proliferation and maintenance of quiescence could potentially contribute to preserving their stem cell properties and yield higher engraftment in vivo.

Figure 5:
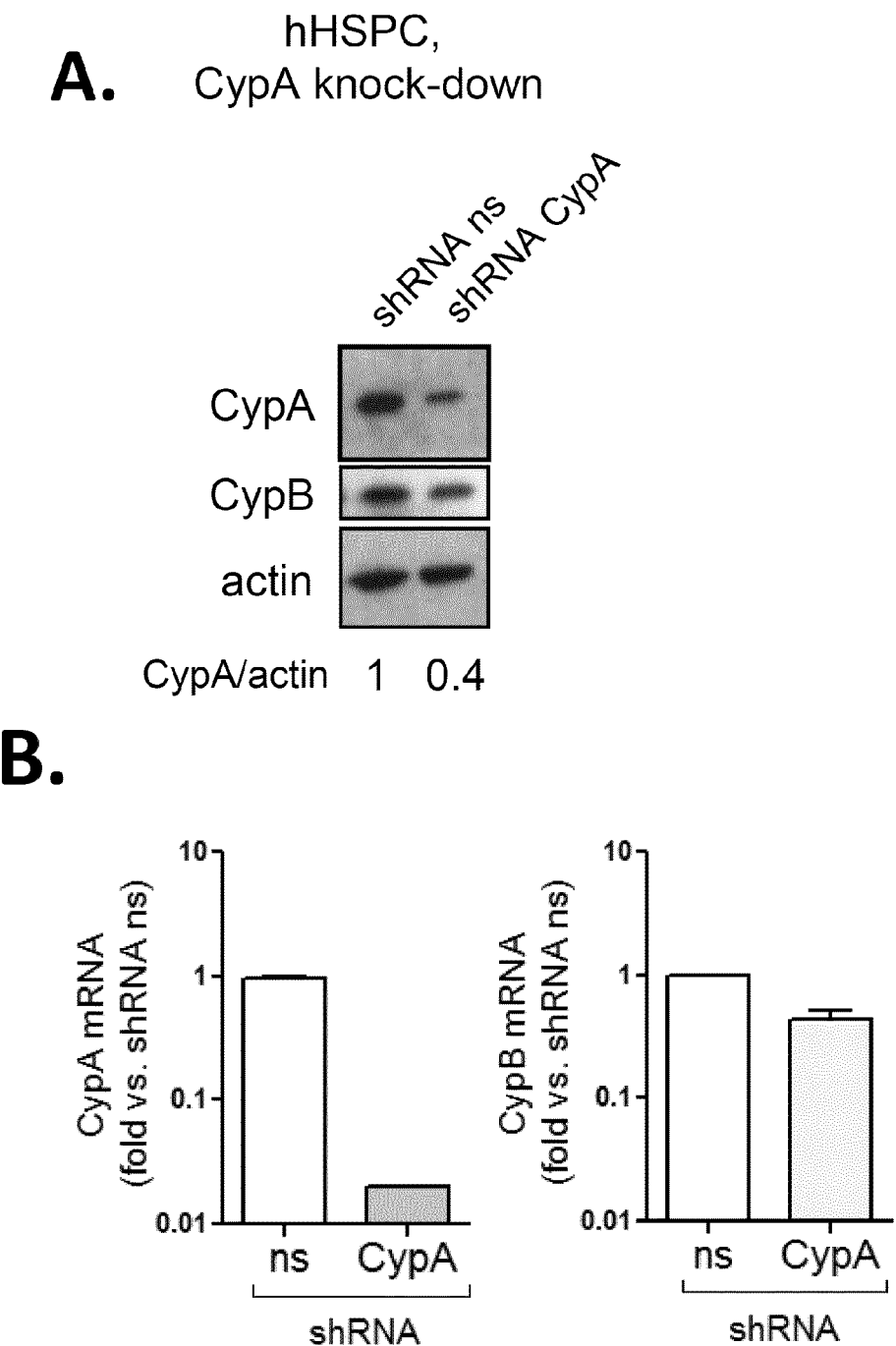
Figure 5:
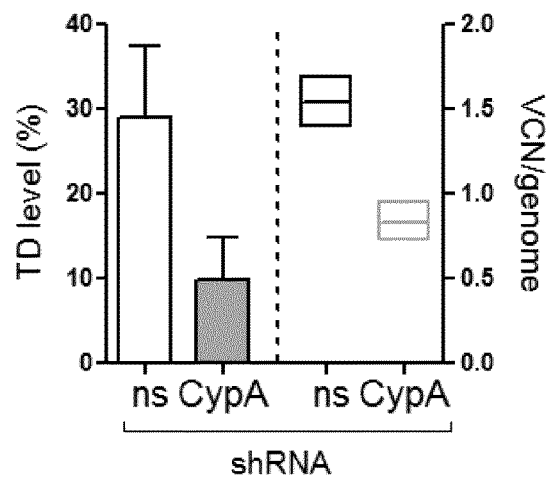
Figure 5:
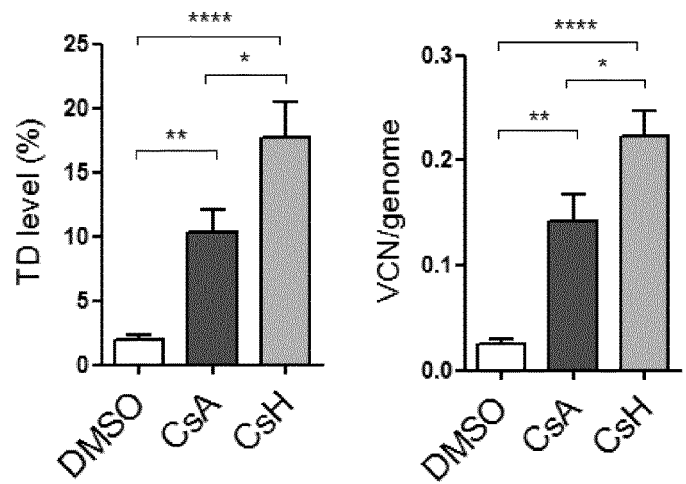
Figure 5:
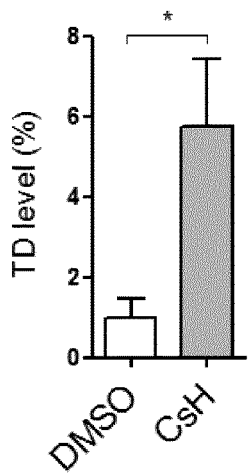
Figure 5:
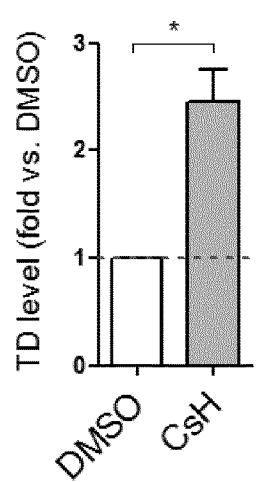
Figure 5:
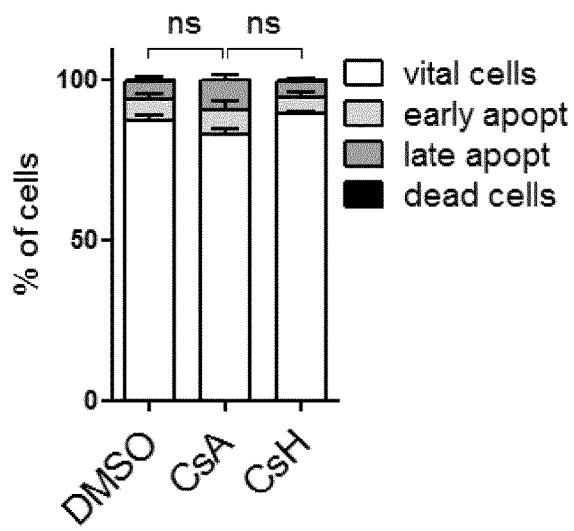
Figure 5:
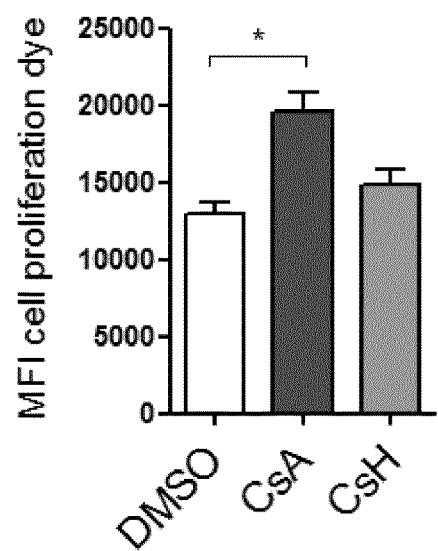
Figure 5:
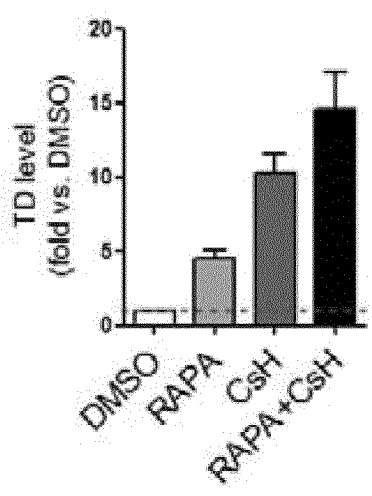
Figure 5:
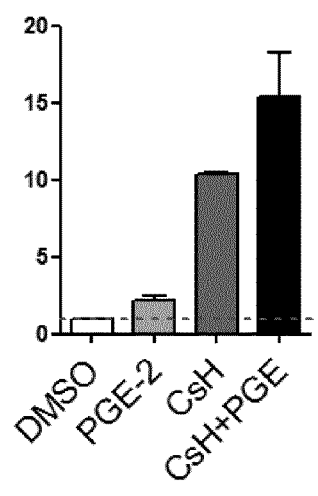
Figure 5:
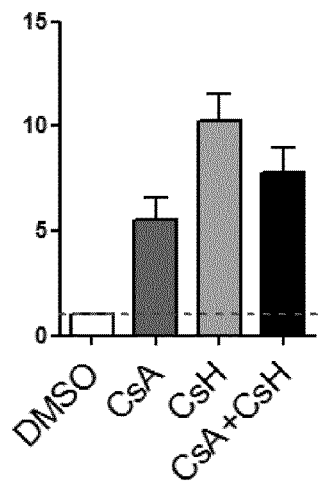
Figure 5:
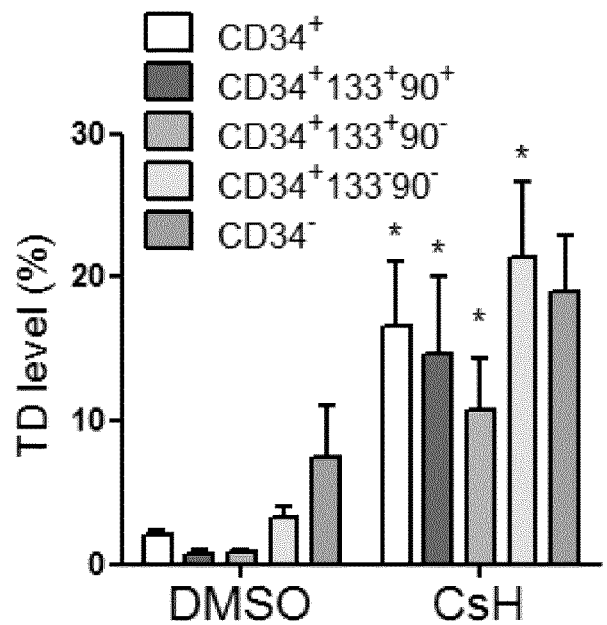
Figure 5:
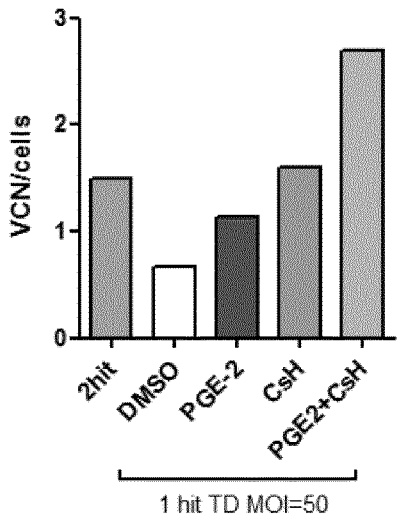
Figure 5:
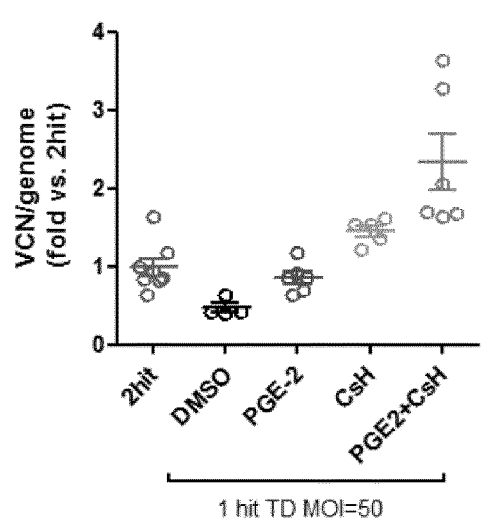
Figure 5:
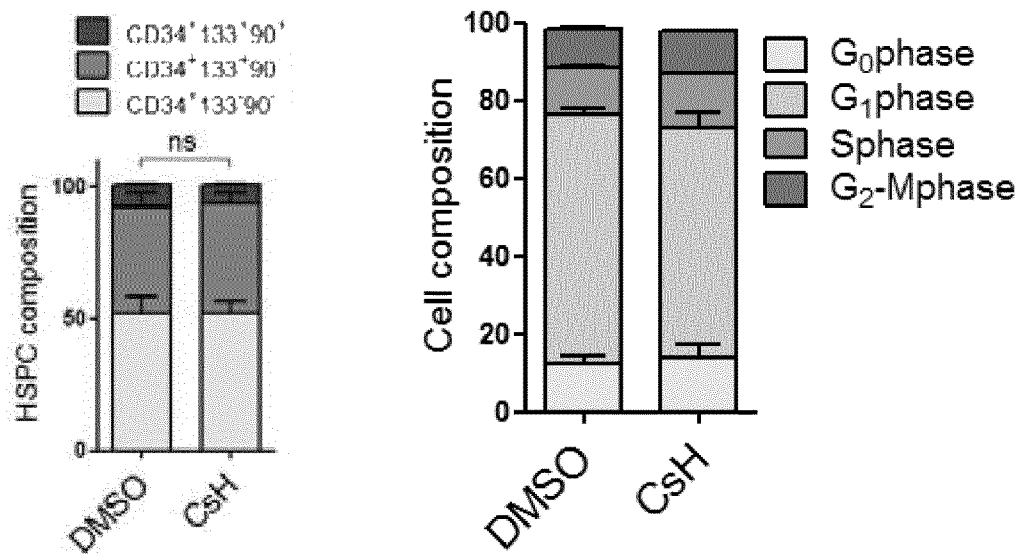
Figure 5:
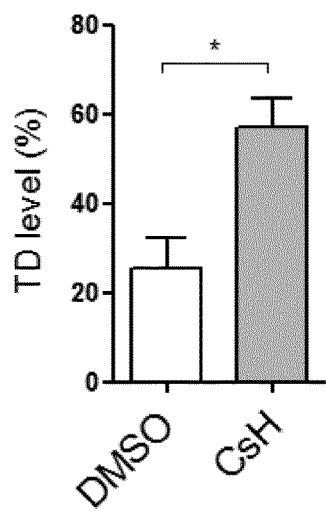

A CypA-Independent Cyclosporin Reveals an Early Block to LV Transduction in HSPCs To directly address the role of CypA during LV transduction and CsA-mediated effects in human HSPCs, we knocked-down (KD) this host co-factor in CB-derived CD34+ cells using shRNA (FIG. 5A-B) and assessed its impact on transduction. In agreement with a positive role of CypA during LV transduction (Towers, G. J. et al. (2014) Cell Host Microbe 16: 10-18), KD of CypA led to lower transduction in human HSPC (FIG. 5C). These results imply that the capacity of CsA to increase LV transduction in HSPCs is likely suboptimal given that it will also interfere with this positive vector interaction with CypA.

Figure 6:
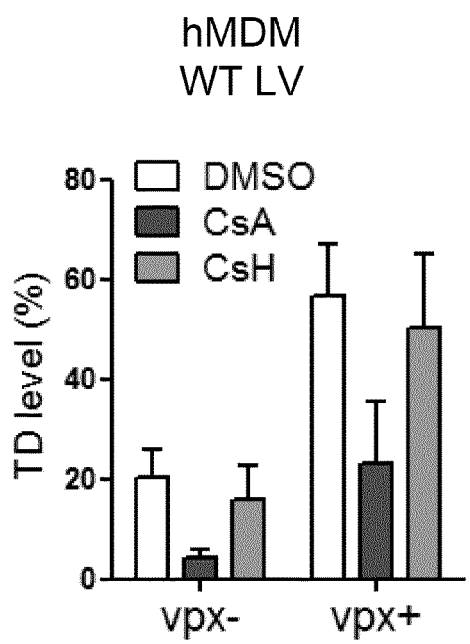
Figure 6:
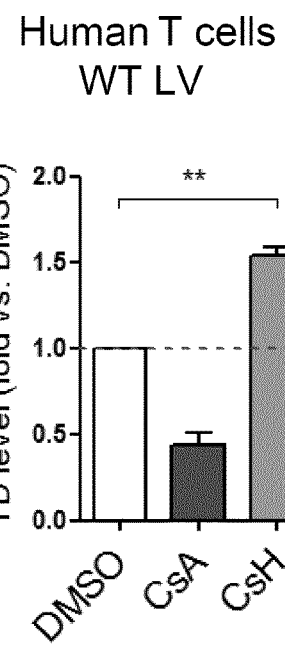
Figure 6:
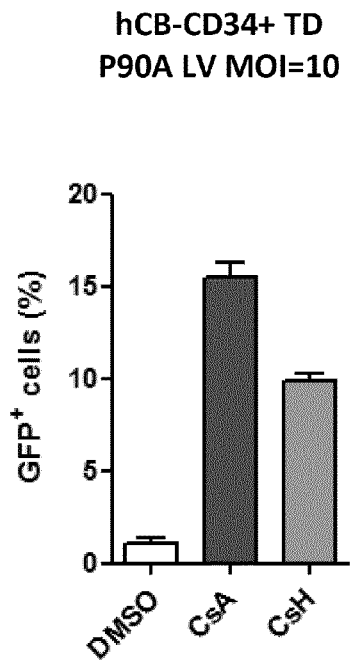
Figure 6:
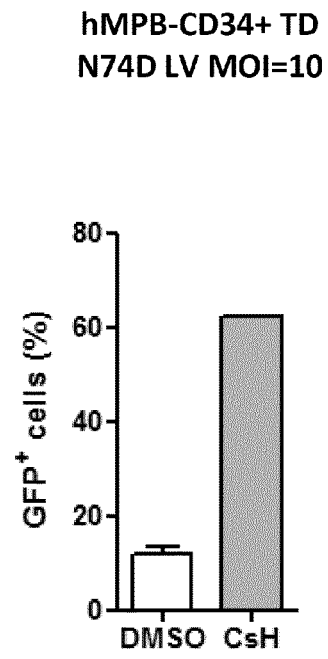
Figure 6:
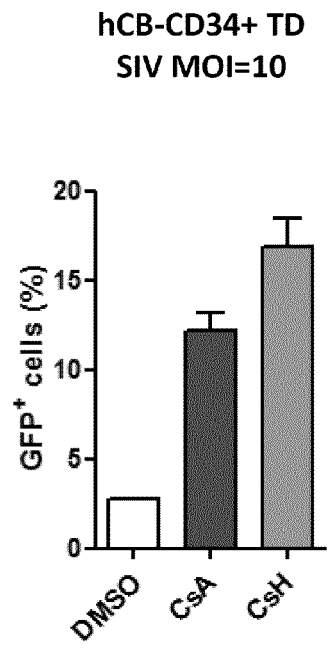
Figure 6:
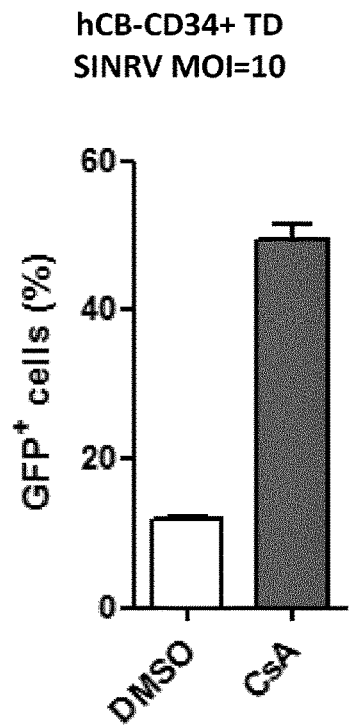
Figure 6:
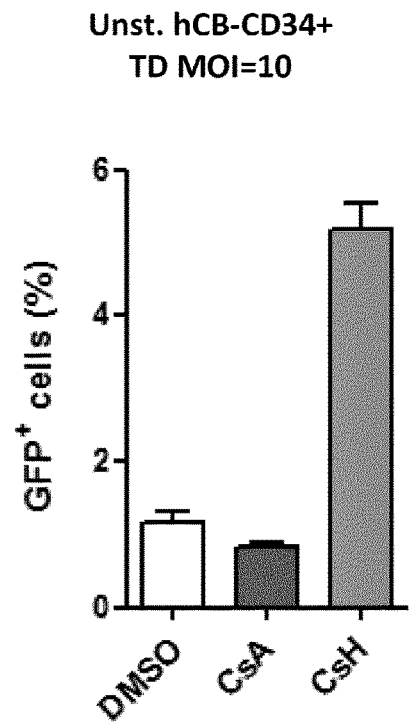
Figure 6:
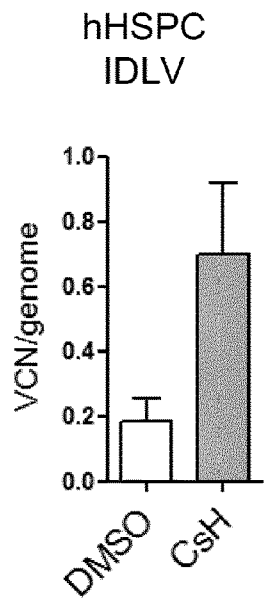
Figure 6:
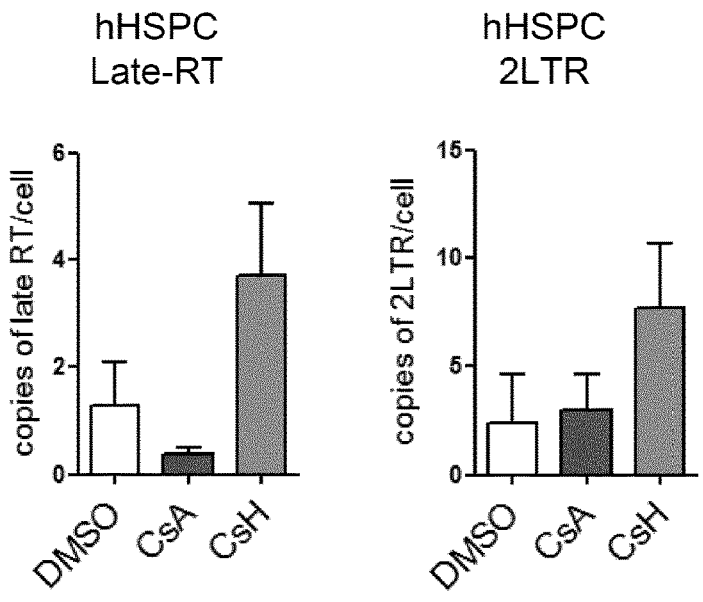
Figure 6:
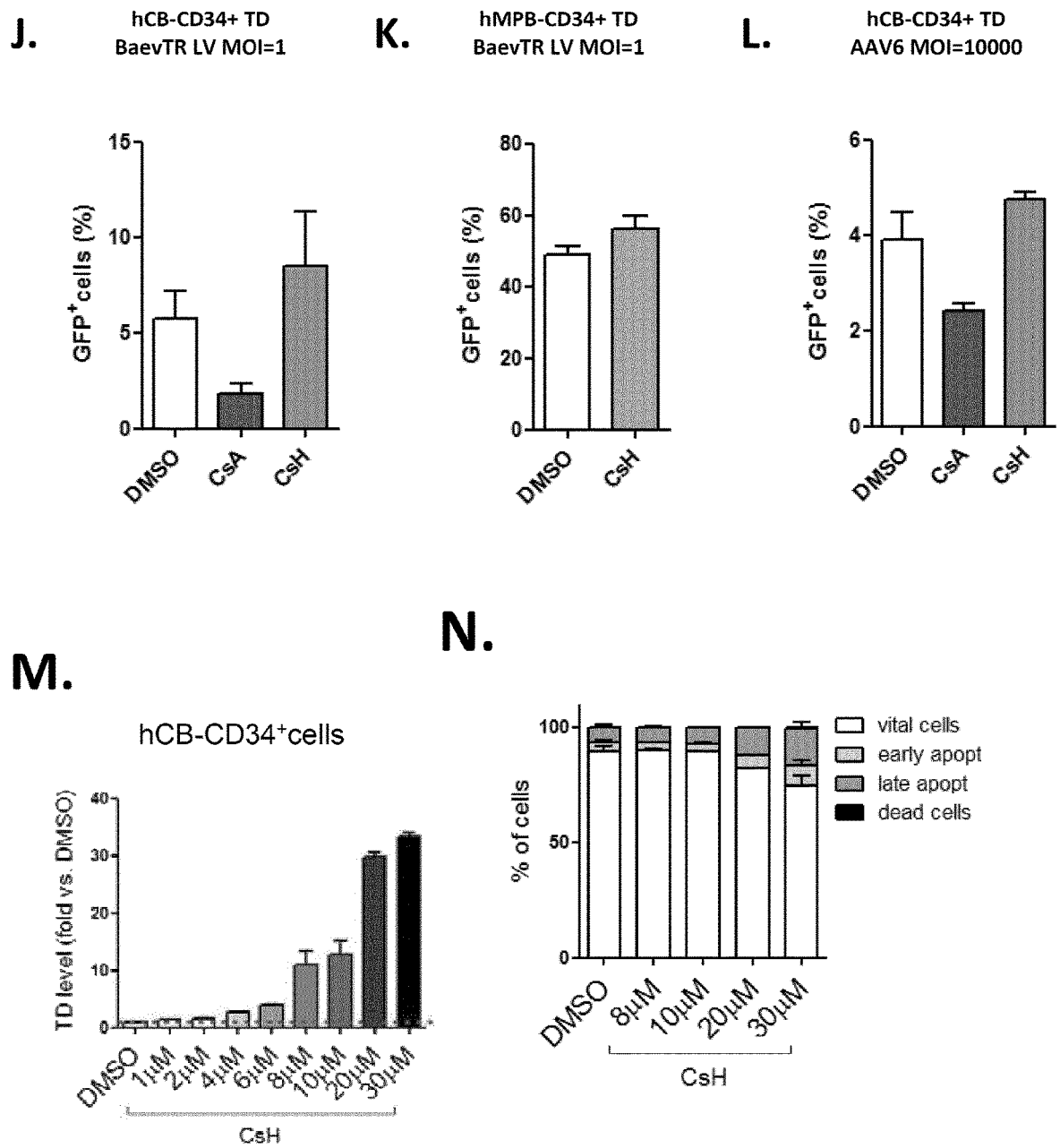

We then tested a naturally occurring isoform of CsA, cyclosporin H (CsH), which does not bind CypA and is not immunosuppressive (Jeffery, J. R. (1991) Clin Biochem 24: 15-21). Remarkably, CsH increased LV transduction in human and murine HSPCs, including in the clinically relevant mPB-derived HSPCs, significantly more efficiently than CsA (FIG. 5D-F; FIG. 6M,N). Importantly, this increase in transduction occurred in absence of any signs of toxicity in vitro (FIG. 5G). As opposed to CsA, and in line with the non-immunosuppressive feature of CsH, no proliferation delay was observed in this case (FIG. 5H). Interestingly, CsH was additive with other two early-acting compounds rapamycin (Rapa) (Petrillo, C. et al. (2015) Mol Ther 23: 352-362; Wang, C. X. et al. (2014). Rapamycin relieves lentiviral vector transduction resistance in human and mouse hematopoietic stem cells. Blood) and prostaglandin E2 (PGE2; Zonari, E. et al. (2017). Efficient Ex Vivo Engineering and Expansion of Highly Purified Human Hematopoietic Stem and Progenitor Cell Populations for Gene Therapy. Stem Cell Reports) but not with CsA (FIG. 5I-J), suggesting that both cyclosporins act on the same lentiviral restriction block that is however different from the early events targeted by Rapa and PGE2, respectively. Importantly, CsH significantly increased transduction efficiencies in all CD34+ subpopulations, including in the more primitive CD34+CD133+CD90+ fraction (FIG. 5K), and in SCID repopulating mPB-derived CD34+ cells transduced with a clinical-grade LV (FIGS. 5L-M, 10 and 11) without altering the subpopulation composition and cell cycle status (FIG. 5N). Noteworthy, CsH efficiently enhanced also gammaretroviral transduction in HSPCs (FIG. 5O), suggesting that it could be useful also for γRV-based gene therapy strategies (Ferrua, F. et al. (2017) Hum Gene Ther 28: 972-981).

We also tested the impact of CsH on LV transduction in other cell types. CsH did not alter transduction in primary human monocyte-derived macrophages (MDM) (FIG. 6A), independently of the SAMHD1-mediated LV restriction that can be relieved by pre-exposure of cells to the SIV accessory protein Vpx (Berger, G. et al. (2011) Nat Protoc 6: 806-816). Conversely, we saw a slight increase in the percentage of GFP+ cells in the context of activated CD4+ T cells (FIG. 6B). These data are in sharp contrast with what we and others have observed for CsA in these cell compartments, further underscoring how the CypA-related effects of CsA likely mask other potential pre-integration benefits it may have on LV transduction. Indeed, the CypA-independent P90A LV capsid mutant benefitted from CsA to similar or even higher extent compared to CsH (FIG. 6C). The transduction levels of the CPSF6-independent N74D capsid mutant LV increased in presence of CsH (FIG. 6D) ruling out this capsid-host interaction from the CsH mechanism of action. Of note, Simian Immunodeficiency Virus (SIV) and γRV-derived vectors, which do not interact with CypA (Fujita, M. et al. (2001) J Virol 75: 10527-10531; Sokolskaja, E. et al. (2006) Curr Opin Microbiol 9: 404-408), benefitted from CsH but also CsA (FIG. 6E), further confirming CypA-independent relief of LV restriction by both cyclosporins. In agreement, and differently from CsA, CsH was able to increase LV transduction also in unstimulated HSPCs (FIG. 6G) as well as using an integrase-defective LV (IDLV) (FIG. 6H), likely due to the maintenance of the beneficial interaction of the vector with CypA in these experimental settings. In line with an earlier pre-integration effect, CsH led to a significant increase in both late-RT and 2LTR circle replication intermediates that were not affected by CsA (FIG. 6I), as we also previously reported (Petrillo, C. et al. (2015) Mol Ther 23: 352-362).

All vectors used in this work thus far have been pseudotyped with the VSV-g envelope glycoprotein, which is the most commonly used in the context of LV gene therapy (Cronin, J. et al. (2005) Curr Gene Ther 5: 387-398). Rapamycin has been shown to facilitate VSV-g mediated pH-dependent endocytosis of LV (Wang, C X. et al. (2014). Rapamycin relieves lentiviral vector transduction resistance in human and mouse hematopoietic stem cells. Blood). To evaluate whether the VSV-g mediated entry of the LV particle could be involved in the CsH-induced increase in transduction, we generated LV pseudotyped with the modified Baboon endogenous retroviral envelope glycoprotein (BaEV-TR) that enters through receptor-mediated fusion directly at the plasma membrane and has been previously described to efficiently transduce several primary human hematopoietic cells, including HSPCs (Girard-Gagnepain, A. et al. (2014) Blood 124: 1221-1231). Interestingly, no clear benefit could be detected for the BaEV-TR pseudotyped LV transduction in CB and mPB-derived HSPC in the presence of CsH, while CsA actually impaired transduction in this setting (FIG. 6J-K). Both cyclosporins failed to improve Adeno-associated vector (AAV) transduction (FIG. 6L) regardless of its endocytosis-mediated entry to target cells (Nonnenmacher, M. et al. (2012) Gene Ther 19: 649-658).

CsH Increases LV Transduction and Gene Editing Efficiency in SCID-Repopulating HSPCs To assess CsH-enhanced transduction in a more clinically relevant setting, we transduced human mPB-CD34$^+$ cells with clinical grade LV expressing the alpha-L-iduronidase (IDUA) transgene (IDUA-LV), designed to treat patients affected by type I mucopolysaccharidoses (MPS-1) (Visigalli, I. et al. (2016) Hum Gene Ther 27: 813-829; Visigalli, I. et al. (2010) Blood 116: 5130-5139). We transplanted the cells transduced in the presence/absence of CsH, PGE-2 or their combination into the xenograft NSG mouse model of human hematopoiesis to follow engraftment and transduction efficiency in vivo (FIG. 10A). For comparison, cells were transduced twice, as dictated by the current standard protocol. No differences in colony-forming capacity could be observed between control and CsH/PGE-2-treated cells (FIG. 10B). Remarkably, one single LV dose in the presence of CsH was enough to yield significantly higher gene marking in vitro (FIG. 11A, B) as well as in long-term repopulating HSC and deriving progeny in vivo (FIG. 10C; FIG. 11C,D). This surpassed the current standard consisting of two rounds of transduction and achieved an almost 10-fold increase in long-term gene marking in vivo compared to the single transduction control group. Although CsH and PGE-2 were additive in vitro also in this setting (FIG. 11A,B) as well as during the early engraftment phase in vivo (FIG. 11C), surprisingly the combinatorial benefit was lost in the long-term repopulating HSC in the bone marrow and progeny in the spleen of the mice (FIG. 10C; FIG. 11D). CsH exposure did not alter the short-term engraftment capacity of HSPC compared to the two-hit protocol, while mice transplanted with single-hit control transduced cells showed higher engraftment of human CD45$^+$ cells compared to the two-hit protocol early at 8 weeks post-transplant (FIG. 10D), in agreement with the notion that shorter ex vivo culture preserves HSPC repopulation capacity (Zonari, E. et al. (2017) Stem Cell Reports 8: 977-990). Lack of such a benefit in the context of CsH treated cells could be related to the enhanced transduction as we have recently shown that lentiviral gene transfer impacts ex vivo HSPC recovery and their short-term in vivo engraftment in a dose-dependent manner due to vector-mediated triggering of the p53 signalling cascade (Piras, F. et al. (2017) EMBO Mol Med 9: 1198-1211). In agreement, exposure of mPB-CD34+ cells to CsH alone did not impact early HSPC engraftment compared to control cells (FIG. 10E). Importantly, higher engraftment associated with shorter ex vivo culture was recovered long-term in the BM and in the spleen of the mice also for cells transduced in presence of CsH (FIG. 10F; FIG. 11E, F).

Suboptimal availability of the donor DNA template may contribute to poor gene editing efficiency by homologous recombination in human HSPCs (Naldini, L. (2011) Nat Rev Genet 12: 301-315). IDLV and AAV are currently the most used vector platforms for donor DNA delivery in gene editing protocols (Naldini, L. (2015) Nature 526: 351-360). As CsH enhanced IDLV transduction in human HSPCs, we tested its effect on the efficiency of IDLV mediated HSPC gene editing (FIG. 10G). Remarkably, delivery of the donor IDLV in the presence of CsH increased gene editing efficiency in human HSPC by two-fold (FIG. 10H) without altering the relative composition of the hematopoietic subpopulations three days after the treatment (FIG. 11G). This increase also occurred in the primitive CD34+CD133+ CD90+ fraction (FIG. 10H), suggesting that CsH favours editing in the long-term repopulating fraction of HSPCs. Indeed, cells edited in the presence of CsH efficiently repopulated NSG mice and the significantly higher targeting efficiency was maintained long-term in peripheral blood as well as in the bone marrow of mice (FIG. 10I-K). Importantly, the increase in gene targeting efficiency was confirmed in all HSPC-derived progeny in the bone marrow (FIG. 11H, 1). Taken together, these results identify CsH as the best performing enhancer of HSPC gene transfer and editing described thus far and strongly support its use in therapeutic HSPC gene engineering.

Figure 7:
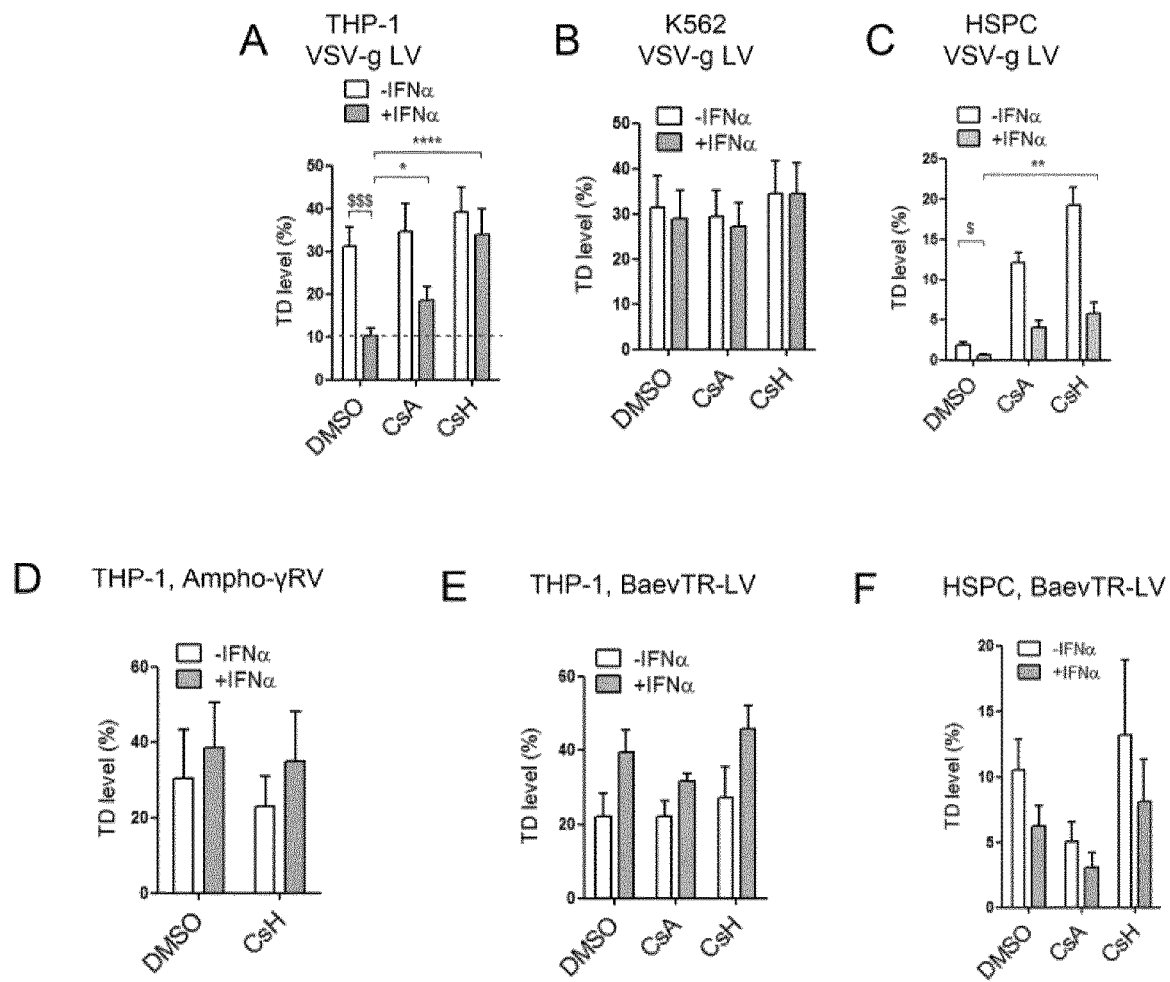
Figure 12:
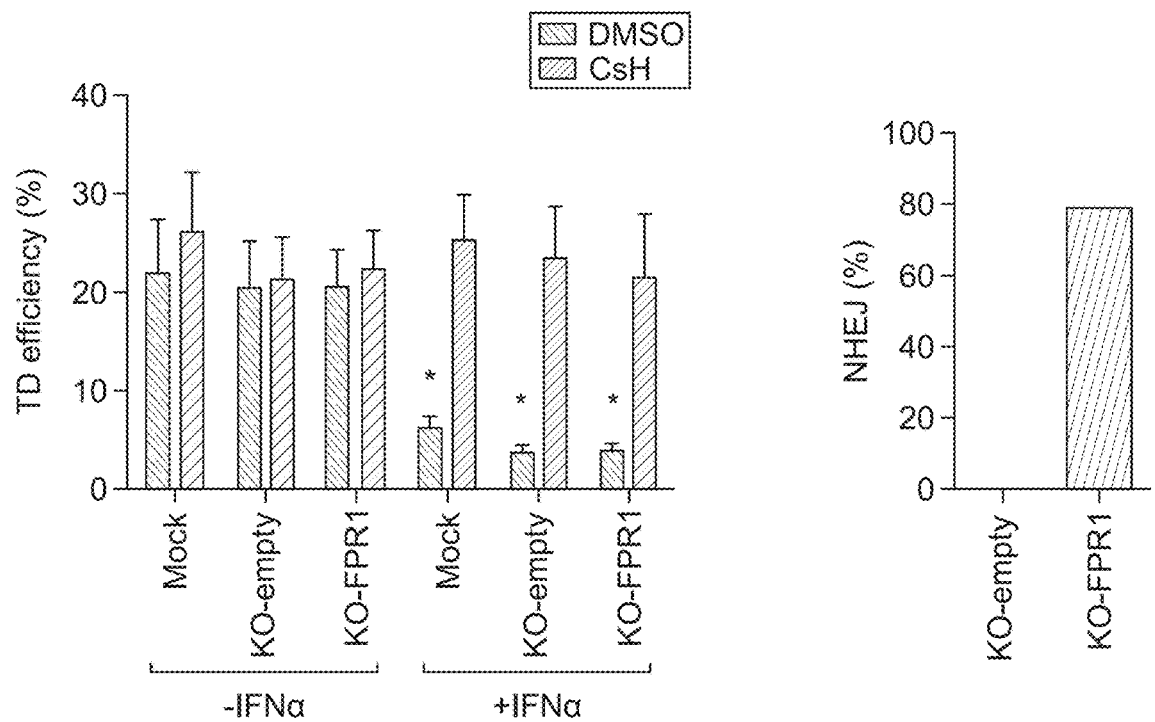
Figure 12:
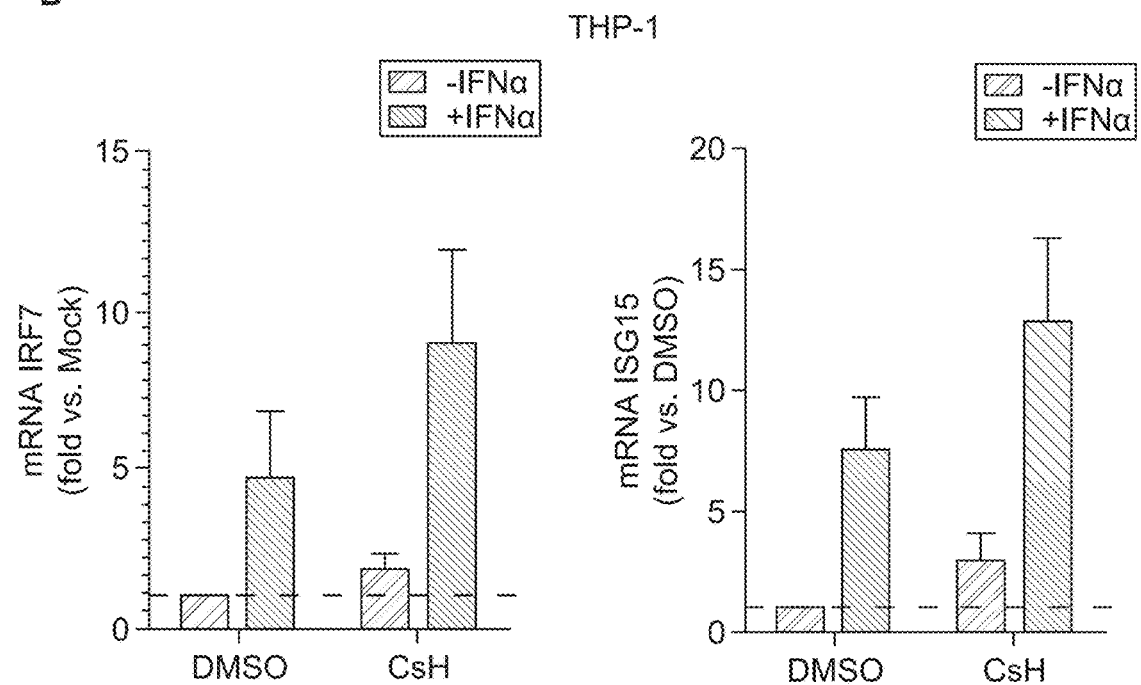
Figure 12:
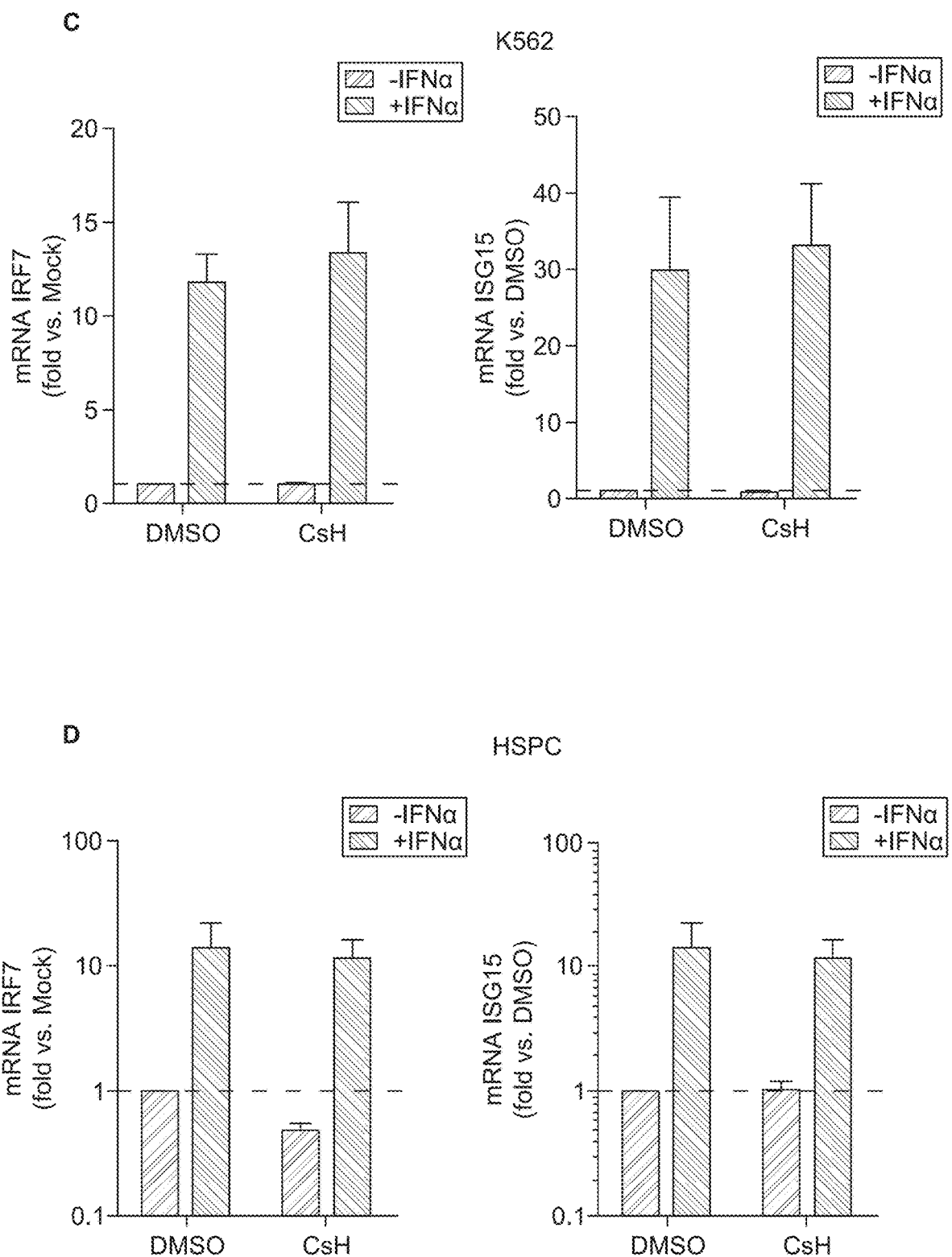

Cyclosporines Counteract an IFN-Inducible Block to VSV-g Dependent Lentiviral Vector Entry In order to gain mechanistic insight regarding how CsH enhances gene transfer and editing in HSPC, we took advantage of the observation that CsA has been reported to improve transduction in human IFNα-stimulated monocytic THP-1 cells (Bulli, L. et al. (2016) J Virol 90: 7469-7480). We first confirmed that CsA partially rescues IFNα-induced inhibition of VSV-g pseudotyped LV transduction in THP-1 cells (FIG. 7A). In comparison, CsH completely rescued IFNα inhibition (FIG. 7A), suggesting that CsH is more potent in relieving the type I IFN-mediated antiviral block. Further, rescue of infection is independent of the immunosuppressive effect of CsA mediated through calcineurin inhibition (Petrillo, C. et al. (2015) Mol Ther 23: 352-362). The best characterised host target of CsH is the formyl peptide receptor 1 (FPR1) involved in neutrophil migration and antimicrobial defenses (de Paulis, A. et al. (1996) J Allergy Clin Immunol 98: 152-164; Prevete, N. et al. (2015) Pharmacol Res 102: 184-191). However, FPR1 is not involved in the IFNα-mediated restriction that is inhibited by cyclosporines, as IFN continued to suppress transduction in THP-1 cells depleted for FPR1 (FIG. 12A). Interestingly, this behaviour was specific to the THP-1 cell line, as neither IFNα or cyclosporine treatment impacted LV transduction in the chronic myelogenous leukemia cell line K562 (FIG. 7B), despite both cells responding to IFNα similarly, evidenced by upregulation of type I IFN-stimulated genes (ISGs) (FIG. 12B, C). This suggests that cell type-specific ISGs and/or co-factors are involved in the cyclosporine-sensitive transduction in THP-1 and HSPC. Both cyclosporines also rescued LV transduction in human HSPC pre-treated with IFNα, with CsH again having a more potent effect compared to CsA (FIG. 7C; FIG. 12D).

Vectors pseudotyped with the MLV-derived amphotropic envelope glycoprotein remained insensitive to type I IFN-mediated inhibition (FIG. 7D), demonstrating that restriction sensitivity is influenced by the viral envelope. In agreement with an envelope-dependent mechanism of action, LV pseudotyped with the modified Baboon endogenous retroviral envelope glycoprotein (BaEV-TR), which enters through receptor-mediated fusion directly at the plasma membrane (Girard-Gagnepain, A. et al. (2014) Blood 124: 1221-1231), remained insensitive to both type I IFN and cyclosporines in THP-1 cells (FIG. 7E). Importantly, transduction by BaEV-TR pseudotyped LV was not enhanced by cyclosporine treatment in HSPC and was less sensitive to IFNα (FIG. 7F). Taken together, these results are consistent with a type I IFN-induced block to VSV-g-mediated LV entry in THP-1 cells that is also active and sensitive to cyclosporines in untreated HSPCs.

Figure 8:
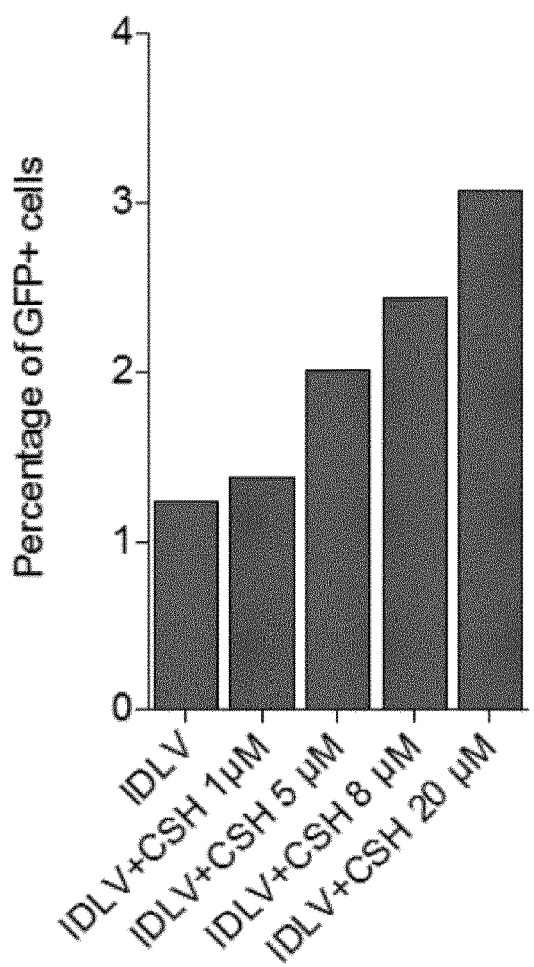
Figure 8:
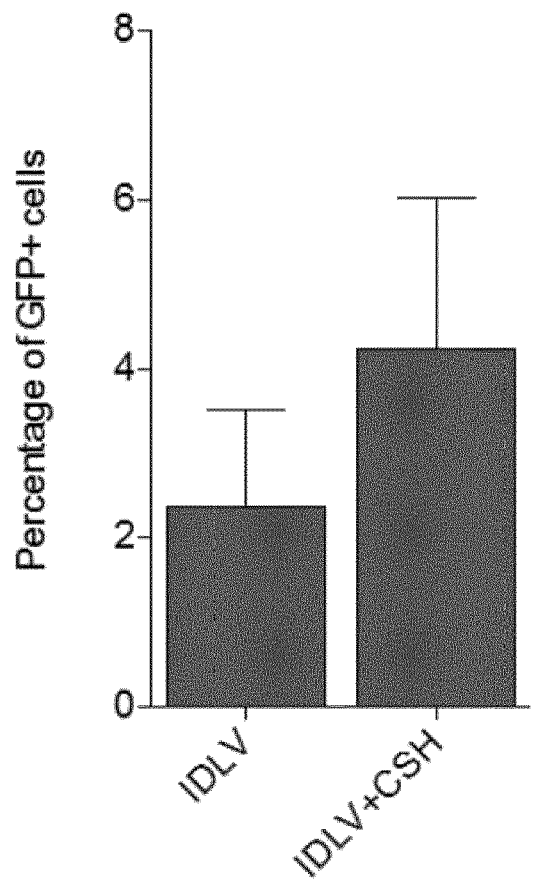
Figure 8:
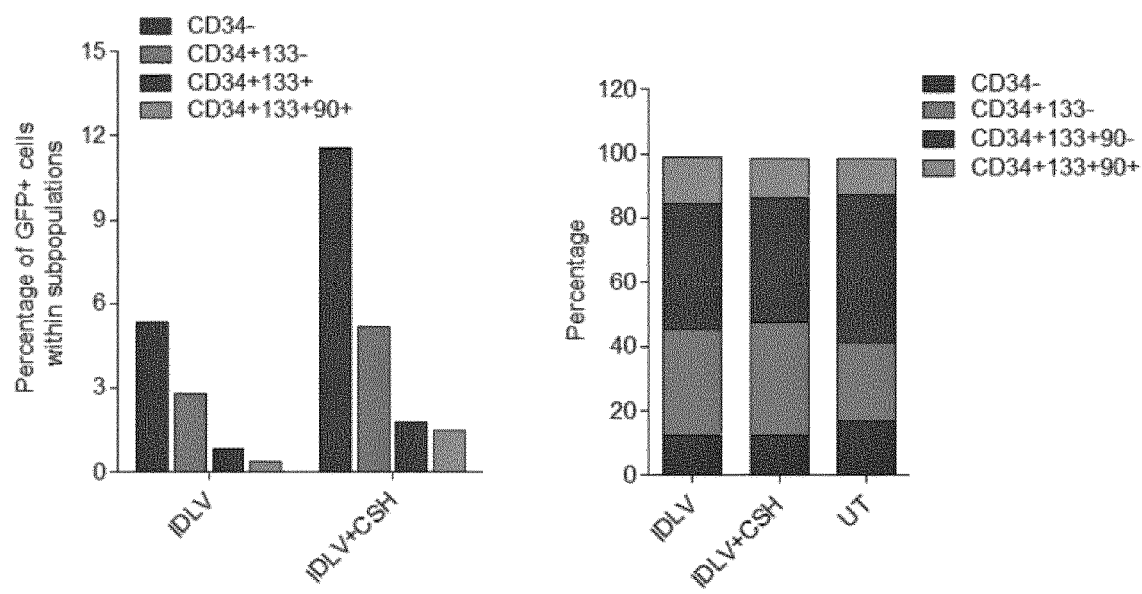

CsH Increases Gene Editing Efficiency in Human and Murine HSPCs as Well as in Primary Human T Cells One of the hurdles to efficient gene editing in human HSPCs may reside in suboptimal availability of the donor DNA template (Naldini, L. (2011) Nat Rev Genet 12: 301-315). IDLV and Adeno-associated vectors (AAV) are currently the most used vector platforms for donor DNA delivery vehicles in gene editing protocols (Naldini, L. (2015) Nature 526: 351-360). Given the capacity of CsH to increase also IDLV transduction efficiency in human and murine HSPCs, we tested its effects in the context of HSPC gene editing approaches. Remarkably, delivery of the donor IDLV in presence of CsH increased gene targeting efficiency by two fold in both murine and human HSPCs (FIG. 8A-B). This increase occurred in all subpopulations, including in the more primitive CD34+CD133+CD90+ fraction, suggesting that CsH could favour editing also in the long-term repopulating fraction of HSPCs, which has been reported to be the most refractory to homologous recombination (HR)-mediated gene targeting (Genovese, P. et al. (2014) Nature 510: 235-240). No significant changes in the relative composition of the haematopoietic subpopulations were observed 3 days after the treatment, suggesting that inclusion of CsH during the gene editing procedure did not adversely affect the survival and growth of the more primitive cells (FIG. 8B, right panel). Furthermore, the use of CsH during HSPC gene editing might enable achievement of levels of gene editing comparable to the current standard protocol with less IDLV. Of note, CsH might improve gene targeting efficiencies in human primary CD3+ T cells, even when the amount of donor IDLV is decreased.

Discussion

Improving HSPC permissiveness to LV transduction remains critical for broad-range implementation of gene therapy as a treatment option for several inherited diseases. Our efforts to improve LV transduction efficiencies in human HSPCs have led to the identification of cyclosporin A (CsA) as a potent enhancer of transduction in this setting (Petrillo, C. et al. (2015) Mol Ther 23: 352-362). Here we have shown its efficacy and safety in clinical culture conditions using bone-marrow (BM)-derived HSPCs and clinical-grade LV and have identified cyclosporin H (CsH) as an even more potent enhancer of LV transduction, based on the molecular characterisation of the mechanism by which these compounds improve LV transduction in human HSPCs.

We show here that CsA not only safely improves LV transduction but also enables better engraftment of human BM-derived HSPC in the NSG xenograft model of human haematopoietic reconstitution. This benefit is likely related to its capacity to decrease HSPC proliferation and better preserve more primitive cells in culture, as both quiescence and shorter ex vivo culture have been shown to improve HSPC engraftment in other settings (Glimm, H. et al. (2000) Blood 96: 4185-4193; Kallinikou, K. et al. (2012) Br J Haematol 158: 778-787; Larochelle, A. et al. (2012) Blood 119: 1848-1855). CsA has also been shown to improve murine Lin- and human CB-derived CD34+ cell engraftment through its capacity to dampen Cyclophilin D-dependent oxidative stress (Mantel, C. R. et al. (2015) Cell 161: 1553-1565). We did not observe similar benefits in our previous studies using CB-derived HSPCs (Petrillo, C. et al. (2015) Mol Ther 23: 352-362), potentially due to the fact that we did not isolate and culture the cells in the strict presence of CsA as performed by Mantel et al. The more quiescent BM-derived CD34+ cells could be less sensitive to environmental oxidative stress, reflecting the benefits of CsA also upon the shorter exposure only during the ex vivo transduction process. Nevertheless, additional mechanisms could also be involved in this shorter exposure setting as we could not detect any clear impact of CsA on the ROS levels in BM-derived HSPCs.

Because of concerns of toxicity related to the immunosuppressive function of CsA, a number of non-immunosuppressive cyclosporin derivatives have been developed and tested for several applications (Peel, M. et al. (2013) Bioorg Med Chem Lett 23: 4485-4492). Nevertheless, most of these still bind also the host factor CypA, that we have demonstrate here to be important for efficient transduction also in HSPCs. In agreement with the notion that a non-immunosuppressive and CypA-independent cyclosporin would be optimal, we identified CsH, a naturally occurring isoform of CsA (Jeffery, J. R. (1991) Clin Biochem 24: 15-21), as an even more potent and less toxic enhancer of LV transduction compared to CsA. CsH is to our knowledge the most efficient enhancer of HSPC gene transfer described thus far, evidenced by our observation that one single round of transduction in the presence of CsH outperforms even the standard double-hit protocol in terms of transduction efficiency without altering engraftment of long-term repopulating HSPC. Further optimization to reduce the vector dose when using CsH should allow high gene marking as well as improved HSPC engraftment. This will be particularly relevant in gene therapy settings in which high levels of gene marking are required but difficult to achieve such as hemoglobinopathies, where the large and complex human β-globin gene expression cassette limits clinical-scale LV production. The characterisation of CsH-mediated effects has provided us much better understanding of the LV restriction blocks occurring in human HSPCs, but potentially also more broadly in other human haematopoietic cells upon triggering of an antiviral response. CsH shared several features with CsA, including capsid independency, but presented also some significant differences. In particular, the integrase-defective LV (IDLV) benefitted from CsH in CD34+ HSPCs, and CsH was able to increase LV transduction also in quiescent HSPCs as well as in primary human T cells, in sharp contrast to what we previously observed for CsA (Petrillo, C. et al. (2015) Mol Ther 23: 352-362). These differences are very likely related to the negative impact CsA has on the vector-CypA interaction that is preserved when using CsH. CypA is a host factor exploited by HIV-1 during the steps of viral uncoating, nuclear import and possibly even integration through interaction with the viral capsid (CA) (Towers, G. J. et al. (2014) Cell Host Microbe 16: 10-18). In the context of HIV-1 research, CsA is well-known to negatively impact lentiviral infection as it disrupts the interaction between CypA and the viral capsid (Sokolskaja, E. et al. (2006) Curr Opin Microbiol 9: 404-408; Towers, G. J. et al. (2014) Cell Host Microbe 16: 10-18). On these premises, the positive effect CsA has on LV transduction in human HSPCs is likely counterbalanced by its negative interference on the CypA-CA axis. In agreement with this hypothesis, CypA-independent LVs did show also an early benefit in presence of CsA in HSPCs (Petrillo, C. et al. (2015) Mol Ther 23: 352-362).

The capacity of CsA to overcome an IFN-induced antiviral state in THP-1 has been recently reported (Bulli, L. et al. (2016) J Virol 90: 7469-7480), but the molecular mechanism has remained elusive. We show here that CsA, and more specifically CsH, overcome the type I IFN induced LV restriction also in the context of human HSPCs. The capacity of cyclosporins to overcome the LV restriction both at steady-state as well as after type I IFN stimulation seems dependent on the type of envelope glycoprotein used to pseudotype the vector. While VSV-g pseudotyped LV benefitted from cyclosporins, pseudotyping the LV with the modified envelope glycoprotein from the Baboon endogenous retrovirus (BaEVTR) rendered the vector insensitive to the beneficial effects of both CsA and CsH. Interestingly, pseudotyping LVs with the BaEVTR envelope glycoprotein has been suggested to significantly improve LV transduction efficiencies in human CD34+ cells compared to VSV-g pseudotyped vectors, including in the unstimulated HSPCs (Girard-Gagnepain, A. et al. (2014) Blood 124: 1221-1231). Based on the results presented here and keeping in mind the positive impact of CsH on LV transduction also in unstimulated HSPCs, this difference could be also explained, at least in part, by the susceptibility of VSV-g pseudotyped LV to a cyclosporin-sensitive restriction block in human HSPCs.

Taken together, our results indicate that cyclosporins act both at an early stage of the LV life cycle as well as at the level of vector integration and that the early effects of CsA are likely masked by its capacity to disrupt the beneficial LV capsid-CypA interaction preserved when using CsH instead. The involvement of the endocytic pathway remains unclear as both cyclosporins are additive with two other early-acting compounds rapamycin and PGE2, both of which have been suggested to act at the level of VSV-g mediated entry ((Wang, C X. et al. (2014). Rapamycin relieves lentiviral vector transduction resistance in human and mouse hematopoietic stem cells. Blood; Zonari, E. et al. (2017). Efficient Ex Vivo Engineering and Expansion of Highly Purified Human Hematopoietic Stem and Progenitor Cell Populations for Gene Therapy. Stem Cell Reports). Furthermore, endocytic entry alone does not allow vectors to benefit from cyclosporins in HSPCs, as AAV6 vector transduction was not improved by these compounds. CsA and CsH were not additive with each other, suggesting that both isoforms act on the same pathway(s) restricting LV transduction in HSPCs. Moreover, the negative impact of CsA on the capsid-CypA interaction seemed to predominate as transduction levels similar to CsA alone were obtained combining the two cyclosporins, further underscoring the importance of this host-vector interaction during LV transduction in HSPC.

The most characterised host target of CsH is the formyl peptide receptor 1 (FPR1) (de Paulis, A. et al. (1996) J Allergy Clin Immunol 98: 152-164). FPR1 belongs to the N-formyl peptide receptor (FPR) family of pattern recognition receptors (PRR) that regulate innate immune responses (Prevete, N. et al. (2015) Pharmacol Res 102: 184-191). FPR expression was initially described in immune cells and subsequently in non-haematopoietic cells and certain tissues, and they have recently been shown to be involved in neural stem cell differentiation (Zhang, L. et al. (2017) Sci Rep 7: 206). Although there are no reports regarding the involvement of FPR1 in HSPC biology thus far, some of the signalling cascades that it can trigger, such as PI3K-AKT signalling, do play critical roles in HSPCs (Lechman, E. R. et al. (2012) Cell Stem Cell 11: 799-811). However, FPR1 is not involved in the cyclosporin-mediated relief of LV restriction in HSPCs.

In line with its broader cell range and capacity to increase also IDLV transduction efficiencies, CsH will likely allow improved gene targeting in HSPCs and primary human CD4+ T cells as well as the down-scaling of the IDLV dose without compromising efficiencies. These results render the IDLV-based editing platforms a competitive alternative to other methods based on AAV or oligonucleotide-mediated donor DNA delivery (Schiroli, G. et al. (2017) Sci Transl Med 9: 411). In particular, there are concerns regarding immunogenicity of AAV-exposed HSPC due to patients frequently harboring pre-existing adaptive immunity against this gene therapy vector. CsH combined with IDLV-based editing platforms could provide a solution for this fraction of identifiable patients and significantly benefit a broad range of cutting edge therapeutic approaches, including immunotherapies and gene correction of monogenic hematopoietic diseases (Naldini, L. (2015) Nature 526: 351-360). Interestingly, CsH seemed to increase targeting efficiencies in particular in the more primitive HSCs, previously shown to be more sensitive than committed progenitors to the cytotoxicity of the gene targeting procedure and less proficient at performing HDR, probably because of their quiescence or slow cycling (Genovese, P. et al. (2014) Nature 510: 235-240). The increased permissiveness to gene delivery allows the use of much lower donor vector doses, lowering thereby also the growth arrest and apoptosis in response to the gene targeting procedure. Our improved CsH-based gene editing protocol would allow increasing the potentially limiting amount of targeted HSPCs to enable effective and safe correction of specific gene defects in humans. Furthermore, as improved procedures for ex vivo HSC expansion become available, combinatorial approaches including also enhancement of donor delivery might increase the overall yield of gene-targeted cells. Indeed, PGE2 has already been used in HSPC gene editing settings to preserve HSPCs ex vivo (Genovese, P. et al. (2014) Nature 510: 235-240). Addition of CsH has the potential to further improve the overall yield of gene edited cells. Furthermore, combining CsH with PGE2 also in the context of more canonical gene therapy protocols has the potential to significantly improve the clinical outcomes in settings in which the therapeutic vector is particularly inefficient or high copy numbers are required for therapeutic efficacy.

Overall, we have identified a novel cyclosporin able to more efficiently and safely counteract both basal as well as type I IFN-inducible LV restriction in primary human HSPCs and T cells. Uncovering the mechanism by which cyclosporins improve LV transduction and donor delivery will have major implications for gene therapy and editing applications. Furthermore, our finding that cyclosporins seem to counteract also type I IFN-induced antiviral effects in a broader range of cell types may contribute to a better understanding of the innate immune mechanisms able to curtail HIV-1 infection.

All publications mentioned in the above specification are herein incorporated by reference. Various modifications and variations of the disclosed uses, methods, cells and compositions of the invention will be apparent to the skilled person without departing from the scope and spirit of the invention. Although the invention has been disclosed in connection with specific preferred embodiments, it should be understood that the invention as claimed should not be unduly limited to such specific embodiments. Indeed, various modifications of the disclosed modes for carrying out the invention, which are obvious to the skilled person are intended to be within the scope of the following claims.

---

The invention claimed is:

1. A method of transducing a population of cells comprising the steps of:
    (a) contacting the population of cells with cyclosporin H (CsH); and
    (b) transducing the population of cells with a viral vector, wherein the viral vector is a lentiviral or gammaretroviral vector and wherein the viral vector is pseudotyped to enter cells via an endocytosis-dependent mechanism,
wherein the population of cells comprises: (i) CD34+ HSPCs; (ii) CD14+ monocytes; (iii) CD4+ or CD3+ T cells; (iv) CD34+ bone marrow cells; or (v) CD34+ peripheral blood cells.

2. The method of claim 1, wherein steps (a) and (b) are carried out in vitro or ex vivo.

3. The method of claim 1, wherein the percentage of cells transduced by the vector is increased and/or the vector copy number per cell is increased.

4. The method of claim 1, wherein the CsH is at a concentration of about 1-50 μM.

5. The method of claim 1, wherein the population of cells is contacted with CsH in combination with rapamycin.

6. The method of claim 1, wherein the population of cells is contacted with CsH in combination with prostaglandin E2.

7. The method of claim 1, comprising a further step of enriching the population for CD34+/CD38− cells.

8. The method of claim 1, wherein efficiency of transduction of the population of cells by the viral vector is increased and/or efficiency of gene editing of the population of cells when transduced by the viral vector is increased.

9. The method of claim 1, wherein the method further comprises a wash step before or after transducing the population of cells with the viral vector, wherein the wash step substantially removes the CsH.

10. The method of claim 1, wherein the T cells are $CD4^+$ and/or $CD3^+$ T cells.

11. The method of claim 1, wherein the viral vector is a lentiviral vector.

12. The method of claim 6, wherein the prostaglandin E2 is 16-16 dimethyl prostaglandin E2.

13. The method of claim 1, wherein the viral vector is an integration-defective lentiviral vector (IDLV).

14. The method of claim 1, wherein the cells are stimulated cells.

15. The method of claim 1, wherein the population of cells is contacted with CsH in combination with another agent capable of increasing the efficiency of transduction.

16. The method of claim 1, wherein the viral vector comprises a nucleotide of interest, and wherein
    the nucleotide of interest encodes a chimeric antigen receptor (CAR).

17. The method of claim 1, wherein the viral vector is a VSV-g pseudotyped vector.

* * * * *

SEQUENCE LISTING

```
<160> NUMBER OF SEQ ID NOS: 16

<210> SEQ ID NO 1
<211> LENGTH: 98
<212> TYPE: DNA
<213> ORGANISM: Artificial Sequence
<220> FEATURE:
<223> OTHER INFORMATION: Fusion-LTR primer
<220> FEATURE:
<221> NAME/KEY: misc_feature
<222> LOCATION: (59)..(70)
<223> OTHER INFORMATION: random 12 nucleotide sequence to increase
      cluster separation
<220> FEATURE:
<221> NAME/KEY: misc_feature
<222> LOCATION: (71)..(78)
<223> OTHER INFORMATION: eight nucleotide tag

<400> SEQUENCE: 1
aatgatacgg cgaccaccga gatctacact ctttccctac acgacgctct tccgatctnn    60
nnnnnnnnnn nnnnnnnnac cctttagtc agtgtgga                             98

<210> SEQ ID NO 2
<211> LENGTH: 99
<212> TYPE: DNA
<213> ORGANISM: Artificial Sequence
<220> FEATURE:
<223> OTHER INFORMATION: Fusion-LC primer
<220> FEATURE:
<221> NAME/KEY: misc_feature
<222> LOCATION: (59)..(70)
<223> OTHER INFORMATION: random 12 nucleotide sequence to increase
      cluster separation
<220> FEATURE:
<221> NAME/KEY: misc_feature
<222> LOCATION: (71)..(78)
<223> OTHER INFORMATION: eight nucleotide tag

<400> SEQUENCE: 2
caagcagaag acggcatacg agatgtgact ggagttcaga cgtgtgctct tccgatctnn    60
nnnnnnnnnn nnnnnnnnga tctgaattca gtggcacag                           99

<210> SEQ ID NO 3
<211> LENGTH: 23
<212> TYPE: DNA
<213> ORGANISM: Artificial Sequence
<220> FEATURE:
<223> OTHER INFORMATION: recognized genomic sequence

<400> SEQUENCE: 3
ttccacagag tgggttaaag cgg                                            23

<210> SEQ ID NO 4
<211> LENGTH: 22
<212> TYPE: DNA
<213> ORGANISM: Artificial Sequence
```

```
<220> FEATURE:
<223> OTHER INFORMATION: genomic sequence recognized by gRNA (AAVS1
      locus)

<400> SEQUENCE: 4
tcaccaatcc tgtccctagt gg                                            22

<210> SEQ ID NO 5
<211> LENGTH: 23
<212> TYPE: DNA
<213> ORGANISM: Artificial Sequence
<220> FEATURE:
<223> OTHER INFORMATION: genomic sequence recognized by gRNA (intron
      IL2RG)

<400> SEQUENCE: 5
actggccatt acaatcatgt ggg                                           23

<210> SEQ ID NO 6
<211> LENGTH: 23
<212> TYPE: DNA
<213> ORGANISM: Artificial Sequence
<220> FEATURE:
<223> OTHER INFORMATION: primer to detect late-RT product, LATE RT fw
      (DU3 sense)

<400> SEQUENCE: 6
tcactcccaa cgaagacaag atc                                           23

<210> SEQ ID NO 7
<211> LENGTH: 19
<212> TYPE: DNA
<213> ORGANISM: Artificial Sequence
<220> FEATURE:
<223> OTHER INFORMATION: primer to detect late-RT product, LATE RT rv
      (5NC2 rev)

<400> SEQUENCE: 7
gagtcctgcg tcgagagag                                                19

<210> SEQ ID NO 8
<211> LENGTH: 25
<212> TYPE: DNA
<213> ORGANISM: Artificial Sequence
<220> FEATURE:
<223> OTHER INFORMATION: primer to detect 2LTR product, 2LTR fw (2junct)

<400> SEQUENCE: 8
cagtgtggaa aatctctagc agtac                                         25

<210> SEQ ID NO 9
<211> LENGTH: 21
<212> TYPE: DNA
<213> ORGANISM: Artificial Sequence
<220> FEATURE:
<223> OTHER INFORMATION: primer to detect 2LTR product, 2LTR rv (J2 rev)

<400> SEQUENCE: 9
gccgtgcgcg cttcagcaag c                                             21

<210> SEQ ID NO 10
<211> LENGTH: 18
<212> TYPE: DNA
<213> ORGANISM: Artificial Sequence
<220> FEATURE:
<223> OTHER INFORMATION: primer to detect TELO, hTelo fw
```

```
<400> SEQUENCE: 10
ggcacacgtg gcttttcg                                                   18

<210> SEQ ID NO 11
<211> LENGTH: 24
<212> TYPE: DNA
<213> ORGANISM: Artificial Sequence
<220> FEATURE:
<223> OTHER INFORMATION: primer to detect TELO, hTelo rev

<400> SEQUENCE: 11
ggtgaacctc gtaagtttat gcaa                                            24

<210> SEQ ID NO 12
<211> LENGTH: 18
<212> TYPE: DNA
<213> ORGANISM: Artificial Sequence
<220> FEATURE:
<223> OTHER INFORMATION: primer HIV sense

<400> SEQUENCE: 12
tactgacgct ctcgcacc                                                   18

<210> SEQ ID NO 13
<211> LENGTH: 17
<212> TYPE: DNA
<213> ORGANISM: Artificial Sequence
<220> FEATURE:
<223> OTHER INFORMATION: primer HIV antisense

<400> SEQUENCE: 13
tctcgacgca ggactcg                                                    17

<210> SEQ ID NO 14
<211> LENGTH: 20
<212> TYPE: DNA
<213> ORGANISM: Artificial Sequence
<220> FEATURE:
<223> OTHER INFORMATION: probe FAM

<400> SEQUENCE: 14
atctctctcc ttctagcctc                                                 20

<210> SEQ ID NO 15
<211> LENGTH: 22
<212> TYPE: DNA
<213> ORGANISM: Artificial Sequence
<220> FEATURE:
<223> OTHER INFORMATION: primer deltaU3 sense

<400> SEQUENCE: 15
cgagctcaat aaaagagccc ac                                              22

<210> SEQ ID NO 16
<211> LENGTH: 20
<212> TYPE: DNA
<213> ORGANISM: Artificial Sequence
<220> FEATURE:
<223> OTHER INFORMATION: primer PBS antisense

<400> SEQUENCE: 16
gagtcctgcg tcggagagag                                                 20
```